US007572456B2

(12) United States Patent
Johnson et al.

(10) Patent No.: US 7,572,456 B2
(45) Date of Patent: Aug. 11, 2009

(54) HUMANIZED ANTIBODIES AGAINST WEST NILE VIRUS AND THERAPEUTIC AND PROPHYLACTIC USES THEREOF

(75) Inventors: Leslie S. Johnson, Darnestown, MD (US); Ling Huang, Bethesda, MD (US)

(73) Assignee: MacroGenics, Inc., Rockville, MD (US)

( * ) Notice: Subject to any disclaimer, the term of this patent is extended or adjusted under 35 U.S.C. 154(b) by 0 days.

(21) Appl. No.: 11/226,886

(22) Filed: Sep. 13, 2005

(65) Prior Publication Data

US 2006/0057149 A1 Mar. 16, 2006

Related U.S. Application Data

(60) Provisional application No. 60/609,766, filed on Sep. 13, 2004.

(51) Int. Cl.
*A61K 39/00* (2006.01)
*A61K 39/12* (2006.01)
*A61Q 5/00* (2006.01)
*C12P 7/24* (2006.01)
*C12P 7/52* (2006.01)
*C12N 5/16* (2006.01)
*C12N 11/10* (2006.01)

(52) U.S. Cl. ............. 424/218.1; 424/70.2; 424/133.1; 424/139.1; 435/141; 435/147; 435/178; 435/345

(58) Field of Classification Search ............... None
See application file for complete search history.

(56) References Cited

U.S. PATENT DOCUMENTS

| 2003/0148261 A1* | 8/2003 | Fikrig et al. ............ 435/5 |
| 2006/0067940 A1 | 3/2006 | Diamond et al. |
| 2006/0115837 A1 | 6/2006 | Fremont et al. |

OTHER PUBLICATIONS

Oliphant et al., Development of a humanized monoclonal antibody with therapeutic potential against West Nile virus, Nature Medicine, May 2005, vol. 11, No. 5, pp. 522-530.*
Nybakken et al., Structural basis of West Nile virus neutralization by a therapeutic antibody, Nature, Sep. 2005, vol. 437, No. 29, pp. 764-768.*
Roehrig et al., Antibody prophylaxis and therapy for flavivirus encephalitis infections, Annals of the New York Academy of Sciences, Dec. 2001, vol. 951, pp. 286-297.*
Beasley et al., Identification of Neutralizing Epitopes within Structural Domain III of the West Nile Virus Envelope Protein, Journal of Virology, Dec. 2002, vol. 76, No. 24, pp. 13097-13100.*
U.S. Appl. No. 60/581,819, filed Feb. 21, 2004, Diamond et al.
U.S. Appl. No. 60/609,766, filed Sep. 13, 2004, Johnson et al.
Agrawal et al., 2003, "Human immunoglobulin as a treatment for West Nile virus infection," J. Infect. Dis. 188(1):1-4.
Allison et al., 1999, "Mapping of functional elements in the stem-anchor region of tick-borne encephalitis virus envelope protein E," J. Virol. 73(7):5605-12.

Anderson et al., 2002, "Efficacy of interferon alpha-2b and ribavirin against West Nile virus in vitro," Emerg. Infect. Dis. 8(1):107-8.
Asnis et al., 2000, "The West Nile Virus outbreak of 1999 in New York: the Flushing Hospital experience," Clin. Infect. Dis. 30(3):413-8.
Beasley et al., 2001, "Epitopes on the dengue 1 virus envelope protein recognized by neutralizing IgM monoclonal antibodies," Virology 279(2):447-58.
Beasley et al., 2002, "Identification of neutralizing epitopes within structural domain III of the West Nile virus envelope protein," J. Virol. 76(24):13097-100.
Ben-Nathan et al., 1996, "West Nile virus neuroinvasion and encephalitis induced by macrophage depletion in mice," Arch. Virol. 141(3-4):459-69.
Ben-Nathan et al., 2003, "Prophylactic and therapeutic efficacy of human intravenous immunoglobulin in treating West Nile virus infection in mice," J. Infect. Dis. 188(1):5-12.
Brandriss et al., 1986, "Lethal 17D yellow fever encephalitis in mice. I. Passive protection by monoclonal antibodies to the envelope proteins of 17D yellow fever and dengue 2 viruses," J. Gen. Virol. 67 ( Pt 2):229-34.
Broom et al., 2000, "Immunisation with gamma globulin to Murray Valley encephalitis virus and with an inactivated Japanese encephalitis virus vaccine as prophylaxis against Australian encephalitis: Evaluation in a mouse model," J. Med. Virol. 61:259-265.
Camenga et al., 1974, "Cyclophosphamide-potentiated West Nile viral encephalitis: relative influence of cellular and humoral factors," J. Infect. Dis. 130(6):634-41.
Cardosa et al., 1986, "Interaction of West Nile virus with primary murine macrophages: role of cell activation and receptors for antibody and complement," J. Virol. 57(3):952-9.
Cecilia et al., 1991, "Nucleotide changes responsible for loss of neuroinvasiveness in Japanese encephalitis virus neutralization-resistant mutants," Virology 181(1):70-7.
Chambers et al., 1990, "Flavivirus genome organization, expression, and replication," Annu. Rev. Microbiol. 44:649-88.

(Continued)

*Primary Examiner*—Bruce Campell
*Assistant Examiner*—Sharon Hurt
(74) *Attorney, Agent, or Firm*—Drinker Biddle & Reath LLP

(57) ABSTRACT

The present invention relates to compositions comprising humanized antibodies or fragments thereof that immunospecifically bind to one or more antigens of a flavivirus, particularly of West Nile Virus (WNV) and methods for preventing, treating or ameliorating symptoms associated with a flavivirus, particularly of West Nile Virus (WNV) infection utilizing said compositions. In particular, the present invention relates to methods for preventing, treating or ameliorating symptoms associated with WNV infection, said methods comprising administering to a human subject an effective amount of one or more humanized antibodies or fragments thereof that immunospecifically bind to a WNV antigen. The present invention also relates to detectable or diagnostic compositions comprising humanized antibodies or fragments thereof that immunospecifically bind to a WNV antigen and methods for detecting or diagnosing WNV infection utilizing said compositions.

19 Claims, 12 Drawing Sheets

OTHER PUBLICATIONS

Figure 2B:
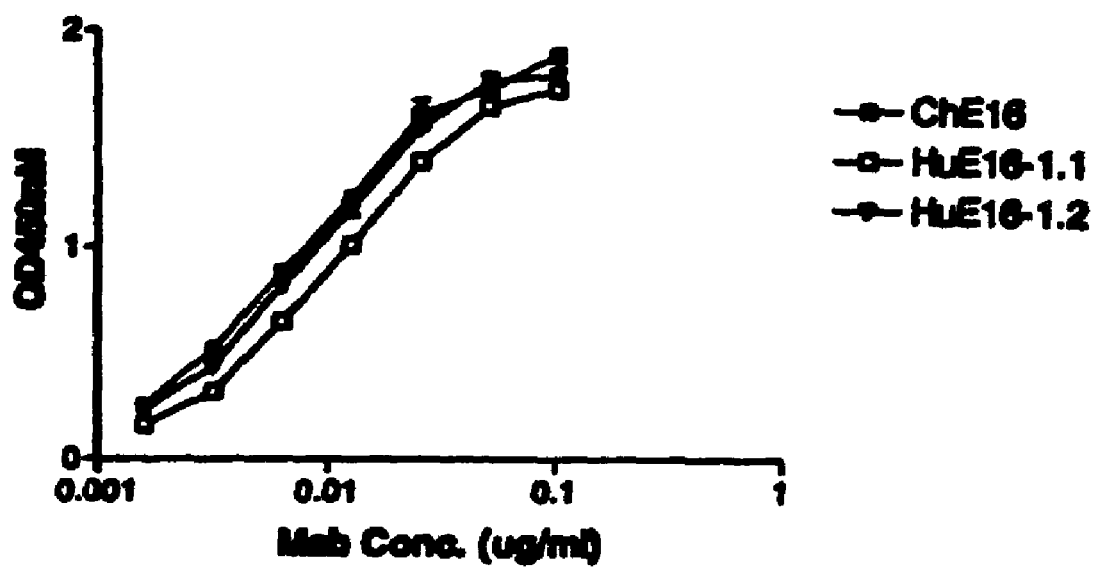

Chiba et al., 1999, "Protection against tick-borne encephalitis virus isolated in Japan by active and passive immunization," Vaccine 17(11-12):1532-9.

Chu et al., 2005, "Inhibition of West Nile virus entry by using a recombinant domain III from the envelope glycoprotein," J. Gen. Virol. 86(Pt 2):405-12.

Crill et al., 2001, "Monoclonal antibodies that bind to domain III of dengue virus E glycoprotein are the most efficient blockers of virus adsorption to Vero cells," J. Virol. 75(16):7769-73.

Diamond et al., 2000, "Infection of Human Cells by Dengue Virus Is Modulated by Different Cell Types and Viral Strains," J. Virol 74:7814-7823.

Diamond et al., 2003, "A critical role for induced IgM in the protection against West Nile virus infection," J. Exp. Med. 198(12):1853-62.

Diamond et al., 2003, "B Cells and Antibody Play Critical Roles in the Immediate Defense of Disseminated Infection by West Nile Encephalitis Virus," J. Virol. 77:2578-2586.

Diamond et al., 2003, "Innate and Adaptive Immune Responses Determine Protection against Disseminated Infection by West Nile Encephalitis Virus," Viral Immunol. 16(3):259-278.

Eisenstein, 2005, "Antibody neutralizes West Nile virus," Lab. Anim. (NY) 34(6):10.

Engle et al., 2003, "Antibody prophylaxis and therapy against West Nile virus infection in wild-type and immunodeficient mice," J. Virol. 77(24):12941-9.

Falconar et al., 1999, "Identification of an epitope on the dengue virus membrane (M) protein defined by cross-protective monoclonal antibodies: design of an improved epitope sequence based on common determinants present in both envelope (E and M) proteins," Arch. Virol. 144(12):2313-30.

Goncalvez et al., 2004, "Chimpanzee Fab fragments and a derived humanized immunoglobulin G1 antibody that efficiently cross-neutralize dengue type 1 and type 2 viruses," J. Virol. 78(23):12910-8.

Halevy et al., 1994, "Loss of active neuroinvasiveness in attenuated strains of West Nile virus: pathogenicity in immunocompetent and SCID mice," Arch. Virol. 137(3-4):355-70.

Haley et al., 2003, "The role for intravenous immunoglobulin in the treatment of West Nile virus encephalitis," Clin. Infect. Dis. 37(6):e88-90.

Halstead et al., 1980, "Enhancement of dengue virus infection in monocytes by flavivirus antisera," Am. J. Trop. Med. Hyg. 29(4):638-42.

Halstead et al., 1989, "Antibody, macrophages, dengue virus infection, shock, and hemorrhage: a pathogenetic cascade," Rev. Infect. Dis. Suppl 4:S830-9.

Hamdan et al., 2002, "Possible benefit of intravenous immunoglobulin therapy in a lung transplant recipient with West Nile virus encephalitis," Transpl. Infect. Dis. 4(3):160-2.

Henchal et al., 1988, "Synergistic interactions of anti-NS1 monoclonal antibodies protect passively immunized mice from lethal challenge with dengue 2 virus," J. Gen. Virol. 69 ( Pt. 8):2101-7.

Holgate et al., 2001, "Efficacy of omalizumab, an anti-immunoglobulin E antibody, in patients with allergic asthma at high risk of serious asthma-related morbidity and mortality," Curr. Med. Res. Opin. 17(4):233-40.

Julander et al., 2005, "Treatment of West Nile virus-infected mice with reactive immunoglobulin reduces fetal titers and increases dam survival," Antiviral Res. 65(2):79-85.

Kimura-Kuroda et al., 1988, "Protection of mice against Japanese encephalitis virus by passive administration with monoclonal antibodies," J. Immunol. 141(10):3606-10.

Kishore et al., 2000, "C1q: structure, function, and receptors," Immunopharmacology 49(1-2):159-70.

Li et al., 2005, "Differential expression of domain III neutralizing epitopes on the envelope proteins of West Nile virus strains," Virology 335(1):99-105.

Lin et al., 1994, "Localization of a neutralizing epitope on the envelope protein of dengue virus type 2," Virology 202(2):885-90.

Mathews et al., 1984, "Elucidation of the topography and determination of the protective epitopes on the E glycoprotein of Saint Louis encephalitis virus by passive transfer with monoclonal antibodies," J. Immunol. 132:1533-1537.

Mehlop et al., 2005, "Complement activation is required for induction of a protective antibody response against West Nile virus infection," J. Virol. 79(12):7466-77.

Miwa et al., 2002, "Crry, but not CD59 and DAF, is indispensable for murine erythrocyte protection in vivo from spontaneous complement attack," Blood 99(10):3707-16.

Oliphant et al., 2005, "Development of a humanized monoclonal antibody with therapeutic potential against West Nile virus," Nat. Med. 11(5):522-30.

Peiris et al., 1982, "Monoclonal antibodies against the flavivirus West Nile," J. Gen. Virol. 58(Pt 2):283-9.

Rager-Zisman et al., 2003, "Efficacy of prophylactic and therapeutic human immunoglobulin on West Nile virus infection," Isr. Med. Assoc. J. 5(10):691.

Razumov et al., 2005, "Neutralizing monoclonal antibodies against Russian strain of the West Nile virus," Viral Immunol. 18(3):558-68.

Roehrig et al., 1983, "Identification of epitopes on the E glycoprotien of Saint Louis encephalitis virus using monoclonal antibodies," Virology 128(1):118-26.

Roehrig et al., 2001, "Antibody prophylaxis and therapy for flavivirus encephalitis infections," Ann. N. Y. Acad. Sci. 951:286-97.

Sanchez et al., 2005, "Characterization of neutralizing antibodies to West Nile virus," Virology 336(1):70-82.

Sawyer, 2000, "Antibodies for the prevention and treatment of viral diseases," Antiviral Res. 47(2):57-77.

Schlesinger et al., 1993, "The Fc portion of antibody to yellow fever virus NS1 is a determinant of protection against YF encephalitis in mice," Virology 192(1):132-41.

Schlesinger et al., 1996, "Replication of yellow fever virus in the mouse central nervous system: comparison of neuroadapted and non-neuroadapted virus and partial sequence analysis of the neuroadapted strain," J. Gen. Virol. 77 ( Pt 6):1277-85.

Secko, 2005, "Immunotherapy for West Nile virus infection," CMAJ 173(6):591.

Seif et al., 1995, "Finer mapping of neutralizing epitope(s) on the C-terminal of Japanese encephalitis virus E-protein expressed in recombinant *Escherichia coli* system," Vaccine 13(16):1515-21.

Shimoni et al., 2001, "Treatment of West Nile virus encephalitis with intravenous immunoglobulin," Emerg. Infect. Dis. 7(4):759.

Shrestha et al., 2004, "Role of CD8+ T cells in control of West Nile virus infection," J. Virol. 78(15):8312-21.

Stanley et al., 1986, "Monoclonal antibody cure and prophylaxis of lethal Sindbis virus encephalitis in mice," J. Virol. 58(1):107-15.

Volk et al., 2004, "Solution structure and antibody binding studies of the envelope protein domain III from the New York strain of West Nile virus," J. Biol. Chem. 279(37):38755-61.

Wu et al., 1997, "Japanese encephalitis virus antigenic variants with characteristic differences in neutralization resistance and mouse virulence," Virus Res. 51:173-181.

Yang et al., 2001, "Induction of potent Th1-type immune responses from a novel DNA vaccine for West Nile virus New York isolate (WNV-NY 1999).," J. Infect. Dis. 184(7):809-16.

Muyldermans, "Single domain camel antibodies: current status," *J. Biotechnol*. 74(4): 277-302.

Riechmann et al., "Single domain antibodies: comparison of camel VH and camelised human VH domains," *J. Immunol. Methods* 231: 25-38 (1999).

* cited by examiner

```
MuE16VH    QVQLQQSGSELMKPGASVQISCKATGYTFS DYWIE WVKQRPGHGLEWIG
HuE16VH-1  ----V---A-VK----S-KV----S----T ----- --R-A--Q----M-
(VH1-18)                  FR1                   CDR1        FR2

MuE16VH    DILCGTGRTRYNEKLKA MATFTADTSSNTAFMQLSSLTSEDSAVYYCAR
HuE16VH-1  ----------------- RV-M-T---TS--Y-E-R--R-D-T-------
(VH1-18)         CDR2                       FR3

MuE16VH    SASYGDYADY WGHGTTLTVSS
HuE16VH-1  ---------- -GQ---V----  HuJH6
(VH1-18)      CDR3       FR4
```

FIG. 1A

```
MuE16VL    DIVMTQSHKFMSTSVGDRVSITC KASQDVSTAVA WYQQKPGQSPKLLIS
HuE16VL-1  -------PDSLAV-L-E-AT-N- ----------- --------P-----Y
(VK-B3)            FR1                CDR1            FR2

MuE16VL    WASTRHT GVPDRFTGSGSGTDYTLTISSVQAEDLALYYC
HuE16VL-1  ------- ------S-------P-------L----V-V---
(VK-B3)     CDR2             FR3

MuE16VL    QQHYTTPLT FGAGTKLELK
HuE16VL-1  --------- --Q------- HuJK2
(VK-B3)      CDR3       FR4
```

FIG. 1B

**Anti WNV Ab Binding ELISA
(Direct antigen down)**

→ ChE16
→ HuE16 1.1
→ ChE16LC/HuE16Hc
→ HuE16LC/ChE16Hc

FIG. 2A

E9 Captured Anti WNV Ab Binding ELISA

- ChE16
- HuE16 1.1
- ChE16LC/HuE16Hc
- HuE16LC/ChE16Hc

** P < 0.05. N = 20-30 mice per arm

FIG. 8

** P < 0.05. N = 10 mice per arm, Experiment still in progress

** P < 0.05. N = 6 to 10 mice per arm. Repeat pending

Prevention of Death from WNV

- 0.03mg/kg
- 0.1mg/kg
- 0.3mg/kg
- 1.0mg/kg
- 3.0mg/kg
- PBS

FIG. 10

HUMANIZED ANTIBODIES AGAINST WEST NILE VIRUS AND THERAPEUTIC AND PROPHYLACTIC USES THEREOF

This application claims priority to U.S. Provisional Application No. 60/609,766, filed on Sep. 13, 2004, which is incorporated herein by reference in its entirety.

1. FIELD OF THE INVENTION

The present invention relates to humanized antibodies, fragments, and variants thereof, that immunospecifically bind to one or more antigens of a *flavivirus*, particularly of West Nile Virus (WNV). The invention also relates to pharmaceutical compositions comprising the humanized antibodies of the invention and methods of use for preventing, treating or ameliorating symptoms associated with a flaviviral, particularly a WNV, infection. The invention also encompasses diagnostic compositions comprising humanized WNV antibodies and methods for diagnosing a WNV infection using the humanized antibodies of the invention.

2. BACKGROUND OF THE INVENTION

WNV cycles between mosquitoes and birds but also infects humans, horses, and other vertebrate species. It is endemic in parts of Africa, Europe, the Middle East, and Asia, and outbreaks throughout the United States during the past four years indicate that it has established its presence in the Western Hemisphere. Humans develop a febrile illness that can progress rapidly to a meningitis or encephalitis syndrome (Hubalek et al., 1999, Emerg Inf Dis 5:643-650), and no specific therapy or vaccine has been approved for use in humans.

2.1 Virology

A member of the *Flavivirus* genus of the Flaviviridae family, WNV is a neurotropic enveloped virus with a single-stranded, positive-polarity 11-kilobase RNA genome. It is translated in the cytoplasm as a polyprotein, and cleaved into structural (C, M, and E) and non-structural (NS1, NS2A, NS2B, NS3, NS4A, NS4B, and NS5) proteins by virus- and host-encoded proteases. The structural proteins include a capsid protein (C), a transmembrane protein (M) that regulates fusion of the virus with the host membrane, and an envelope protein (E) that functions in receptor binding, membrane fusion, and viral assembly. The role of nonstructural proteins is not fully delineated but these proteins form the viral protease (NS2B, NS3), NTPase (NS3), RNA helicase (NS3), and RNA-dependent RNA polymerase (NS5) (Chambers et al. 1990, Annu. Rev. Microbiol. 44: 649-88). After the E protein of WNV binds to an uncharacterized cell surface receptor, viral uptake is believed to occur through receptor-mediated endocytosis (Chambers et al., 1990, Annu Rev Microbiol 44:649-88). In the endosome, an acid-catalyzed conformational change in E (Gollins et al., 1986, J. Gen. Virol. 67:1941-1950; Kimura et al., 1986, J Gen Virol 67:2423-33) releases the nucleocapsid into the cytoplasm. At the endoplasmic reticulum (ER) membrane, the structural proteins and NS1 undergo co-translational translocation, glycosylation, and membrane-associated cleavage, while the other nonstructural proteins are translated in the cytoplasm (Falgout et al., 1995, J Virol 69:7232-43; Markoff et al., 1994, Virology 204:526-40). Assembly occurs at the ER, and viral particles are exocytosed.

2.2 WNV Immunology

Host factors including immune status influence the expression of WNV disease in humans (Camenga et al., 1974, J Infect Dis 130:634-41). Infants, the elderly, and patients with impaired immune systems are at greatest risk for severe neurological disease (Asnis et al., 2000, Clin Infect Dis 30:413-8; Hubalek et al., 1999, Emerg Inf Dis 5:643-650; Tsai et al., 1998, Lancet 352:767-71). Investigations are beginning to elucidate the molecular basis of WNV infection and the protective immune system response. Maturation of the immune system correlates with resistance to WNV infection (Eldadah et al., 1967, Am J Epidemiol 86:776-90; Eldadah et al., 1967, Am J Epidemiol 86:765-75; Weiner et al., 1970, J Hyg (Lond) 68:435-46). Depletion of macrophages increases the neuroinvasiveness and virulence of an attenuated strain (Ben-Nathan et al., 1996, Arch Virol 141:459-69). Lymphocytes are critical for protection against WNV infection as SCID and RAG1 mice uniformly succumb to infection with WNV (Diamond et al., 2003, J Virol 77:2578-2586; Halevy et al., 1994, Arch Virol 137:355-70). Recent studies demonstrate that components of humoral immunity (IgM, IgG, and complement) have essential functions early in the course of infection and prevent dissemination to the central nervous system (CNS) (Diamond et al., 2003, J Virol 77:2578-2586; Diamond et al., 2003, Viral Immunology 16:259-278). The cellular basis of immunity against WNV is beginning to be delineated. Several studies suggest a protective role for cytotoxic and helper T cells. In vitro, T cells kill targets, proliferate, and release inflammatory cytokines after exposure to WNV-infected cells (Douglas et al., 1994, Immunology 82:561-70; Kesson et al., 1987, J Gen Virol 68:2001-6; Kulkarni et al., 1991, Viral Immunol 4:73-82; Liu et al., 1989, J Gen Virol 70:565-73). In vivo, antigen-specific helper and cytotoxic T cell responses are generated in mice after administration of a candidate vaccine strain of WNV (Yang et al., 2001, J Infect Dis 184:809-16). Although the precise contribution of T cell-mediated immunity in vivo to viral clearance and long-term immunity has yet to be established, recent studies demonstrate an essential role for T cells in the control of WNV infection. Mice that lack CD8$^+$ T cells or classical class I MHC molecules show increased mortality and viral loads, and long-term viral persistence in the CNS after WNV infection (Shrestha et al., 2004, J. Virol. 78:8312-21), and an absence of γδ T cells results in increased mortality after WNV infection (Wang et al., 2003, J Immunol 171:2524-2531).

2.3 Antivirals

At present, treatment for all *flavivirus* infections, including WNV, is supportive. Ribavirin has been suggested as a candidate agent because it inhibits WNV infection in cells (Jordan et al., 2000, J Infect Dis 182:1214-7); however, its activity was modest at concentrations that are achievable in the CNS (Anderson et al., 2002, Emerg Infect Dis 8:107-8; Jordan et al., 2000, J Infect Dis 182:1214-7). The limited in vivo experience with ribavirin against *flaviviruses* has not been promising, as it failed to attenuate infection of the closely related Dengue (DEN) virus in mice (Koff et al., 1983, Antimicrob Agents Chemother 24:134-6) and monkeys (Malinoski et al., 1990, Antiviral Res 13:139-49). Based on preliminary cell culture studies (Anderson et al., 2002, Emerg Infect Dis 8:107-8), interferon (IFN) $\alpha_{2b}$ was recently proposed as a possible therapy for WNV. Although in vivo studies have not been performed with WNV, based on experiments with related *flaviviruses*, IFNs may inhibit WNV dissemination (Harinasuta et al., 1985, Southeast Asian J Trop Med Public Health 16:332-6). Mice that are deficient in IFN α, β, and γ receptors succumb to dengue (DEN) virus infection (Johnson et al., 1999, J Virol 73:783-6) or Murray Valley encephalitis (Lobigs et al., 2003, J Gen Virol 84:567-72) virus infection and mice deficient in IFN γ produced higher viral loads after yellow fever virus infection (Liu et al., 2001, J Virol 75:2107-

18). IFN α was effective as prophylaxis and therapy against Saint Louis encephalitis virus in mice (Brooks et al., 1999, Antiviral Res 41:57-64) although clinical benefit was achieved only when therapy was initiated within 24 hours of infection. Indeed, clinical trials on patients with serologically confirmed Japanese encephalitis virus demonstrated no benefit of IFN therapy (Solomon et al., 2003, Lancet 361:821-6). Thus, the window of opportunity for IFN α therapy against WNV infection may be too narrow to be clinically relevant.

The present invention is aimed at addressing the concerns and shortcomings of currents prophylactic and therapeutic methods against flaviviral, particularly WNV, infections.

3. SUMMARY OF THE INVENTION

The instant invention provides humanized antibodies, or fragments thereof, that immunospecifically bind a WNV antigen, e.g., the E protein. In a specific embodiment, the humanized antibodies of the invention bind to the ectodomain of the WNV E protein, e.g., domain III of the WNV E protein comprising amino acids 290 to 415. In most preferred embodiments, the present invention relates to humanized versions of E16, E24, or E34 mouse monoclonal antibodies or fragments thereof, preferably antigen binding fragments thereof. Hybridomas producing antibodies E16, E24, or E34 have been deposited with the American Type Culture Collection (10801 University Blvd., Manassas, Va. 20110-2209) on Jun. 4, 2004 under the provisions of the Budapest Treaty on the International Recognition of the Deposit of Microorganisms for the Purposes of Patent Procedures, and assigned accession numbers PTA-6050, PTA-6051, and PTA-6052, respectively, and are incorporated herein by reference. Representative plasmids encoding humanized antibodies of the invention, e.g., pMGX623-humanized E16 light chain version 1, the vector is pCINeo (Invitrogen), the insert consists of human germline sequence VKB2 and JK2 as framework, human kappa as constant region and mouse E16 CDRs; pMGX624—humanized E16 light chain version 2, same description as pMGX623 except a Y49S mutation in the variable region; pMGX625—humanized E16 heavy chain version 1, the vector is pCINeo (Invitrogen), the insert consists of human germline sequence VH1-18 and JH6 as framework, human IgG1 as constant region, and mouse E16 CDRs; pMGX626—humanized E16 heavy chain version 2, same description as pMGX625 except V67A, M69F, and T71A mutations in the variable region; and pMGX627—humanized E16 heavy chain version 3, same description as pMGX625 except a T71A mutation in the variable region; having ATCC Accession numbers PTA-6199, PTA-6200, PTA-6201, PTA-6202, and PTA-6203, respectively, were deposited under the provisions of the Budapest Treaty with the American Type Culture Collection (10801 University Blvd., Manassas, Va. 20110-2209) on Sep. 10, 2004, and are incorporated herein by reference.

The humanized antibodies of the invention may comprise one or more CDRs of E16, E24, or E34, i.e., have a heavy chain variable region (VH) comprising the amino acid sequence of CDR1 (SEQ ID NO: 1 or SEQ ID NO: 27) and/or CDR2 (SEQ ID NO: 2, SEQ ID NO: 28 or SEQ ID NO: 39) and/or CDR3 (SEQ ID NO: 3, SEQ ID NO: 29 or SEQ ID NO: 40) of E16, E24 or E34 and/or a light chain variable region (VL) comprising the amino acid sequence of CDR1 (SEQ ID NO: 11) and/or a CDR2 (SEQ ID NO: 12) and/or CDR3 (SEQ ID NO: 13 or SEQ ID NO: 34) of E16, E24 or E34. The sequences of the CDRs for E16, E24, and E34 heavy and light chain variable regions are provided in Table 1.

In yet other preferred embodiments, the humanized antibodies of the invention comprise a heavy chain variable region comprising an amino acid sequence of SEQ ID NO: 21, SEQ ID NO: 22, or SEQ ID NO: 23, and/or a light chain variable region comprising the amino acid sequence of SEQ ID NO: 25 or SEQ ID NO: 26, and/or amino acid sequence variants thereof.

In particular, the invention provides a humanized antibody that immunospecifically binds to a WNV antigen, preferably a WNV E antigen, said humanized antibody comprising (or alternatively, consisting of) a VH CDR1 and a VL CDR1; a VH CDR1 and a VL CDR2; a VH CDR1 and a VL CDR3; a VH CDR2 and a VL CDR1; VH CDR2 and VL CDR2; a VH CDR2 and a VL CDR3; a VH CDR3 and a VH CDR1; a VH CDR3 and a VL CDR2; a VH CDR3 and a VL CDR3; a VH1 CDR1, a VH CDR2 and a VL CDR1; a VH CDR1, a VH CDR2 and a VL CDR2; a VH CDR1, a VH CDR2 and a VL CDR3; a VH CDR2, a VH CDR3 and a VL CDR1, a VH CDR2, a VH CDR3 and a VL CDR2; a VH CDR2, a VH CDR3 and a VL CDR3; a VH CDR1, a VL CDR1 and a VL CDR2; a VH CDR1, a VL CDR1 and a VL CDR3; a VH CDR2, a VL CDR1 and a VL CDR2; a VH CDR2, a VL CDR1 and a VL CDR3; a VH CDR3, a VL CDR1 and a VL CDR2; a VH CDR3, a VL CDR1 and a VL CDR3; a VH CDR1, a VH CDR2, a VH CDR3 and a VL CDR1; a VH CDR1, a VH CDR2, a VH CDR3 and a VL CDR2; a VH CDR1, a VH CDR2, a VH CDR3 and a VL CDR3; a VH CDR1, a VH CDR2, a VL CDR1 and a VL CDR2; a VH CDR1, a VH CDR2, a VL CDR1 and a VL CDR3; a VH CDR1, a VH CDR2, a VL CDR2 and a VL CDR3; a VH CDR1, a VH CDR3, a VL CDR1 and a VL CDR2; a VH CDR1, a VH CDR3, a VL CDR1 and a VL CDR3; a VH CDR1, a VH CDR3, a VL CDR2 and a VL CDR3; a VH CDR2, a VH CDR3, a VL CDR1 and a VL CDR2; a VH CDR2, a VH CDR3, a VL CDR1 and a VL CDR3; a VH CDR2, a VH CDR3, a VL CDR2 and a VL CDR3; a VH CDR1, a VH CDR2, a VH CDR3, a VL CDR1 and a VL CDR2; a VH CDR1, a VH CDR2, a VH CDR3, a VL CDR1 and a VL CDR3; a VH CDR1, a VH CDR2, a VL CDR1, a VL CDR2, and a VL CDR3; a VH CDR1, a VH CDR3, a VL CDR1, a VL CDR2, and a VL CDR3; a VH CDR2, a VH CDR3, a VL CDR1, a VL CDR2, and a VL CDR3; or any combination thereof of the VH CDRs and VL CDRs disclosed herein.

In one specific embodiment, the invention provides a humanized E16 antibody, wherein the VH region consists of the framework region (FR) segments from the human germline VH segment VH1-18 and JH6, as depicted in FIG. 1a, and the CDR regions of the E16 VH. In another specific embodiment, the humanized E16 antibody further comprises a VL region, which consists of the FR segments of the human germline VL segment VKB-3, as depicted in FIG. 1b, and the CDR regions of E16 VL.

In certain embodiments, the heavy chain comprises one or more substitutions at Kabat numbers 5, 6, 9, 11, 12, 19, 20, 25, 30, 38, 40, 43, 48, 66, 67, 69, 71, 75, 76, 79, 81, 82A, 83, 85, 87, 105, 109. In certain embodiments, the light chain comprises one or more substitutions at Kabat numbers 8, 9, 10, 11, 12, 13, 15, 17, 19, 20, 22, 43, 49, 63, 71, 78, 83, 85, or 100. In another embodiment, the heavy chain FR3 may consist of the amino acid sequence of SEQ ID NO: 7, SEQ ID NO: 8, or SEQ ID NO: 9. In another embodiment, the light chain FR2 may consist of the amino acid sequence of SEQ ID NO: 16 or SEQ ID NO: 17. Humanized E16 antibodies comprising a VH FR3 sequence of SEQ ID NO: 7, SEQ ID NO: 8, or SEQ ID NO: 9 and a VH FR2 sequence of SEQ ID NO: 16 or SEQ ID NO: 17 are provided in Table 2 as HuE16-1.1, HuE16-1.2, HuE16-2.1, HuE16-2.2, HuE16-3.1, and HuE16-3.2.

The present invention provides humanized antibody molecules specific for WNV in which one or more regions of one or more CDRs of the heavy and/or light chain variable regions of a human antibody (the recipient antibody) have been substituted by analogous parts of one or more CDRs of a donor monoclonal antibody which specifically binds a WNV antigen, e.g., a monoclonal antibody produced by clones E16, E24, or E34. In a most preferred embodiment, the humanized antibody can specifically bind to the same epitope as the donor murine antibody. It will be appreciated by one skilled in the art that the invention encompasses CDR grafting of antibodies in general. Thus, the donor and acceptor antibodies may be derived from animals of the same species and even the same antibody class or sub-class. More usually, however, the donor and acceptor antibodies are derived from animals of different species. Typically the donor antibody is a non-human antibody, such as a rodent MAb, and the acceptor antibody is a human antibody.

In some embodiments, at least one CDR from the donor antibody is grafted onto the human antibody. In other embodiments, at least two and preferably all three CDRs of each of the heavy and/or light chain variable regions are grafted onto the human antibody. The CDRs may comprise the Kabat CDRs, the structural loop CDRs or a combination thereof. In some embodiments, the invention encompasses a humanized WNV antibody comprising at least one CDR grafted heavy chain and at least one CDR-grafted light chain.

In a preferred embodiment, the CDR regions of the humanized WNV specific antibody are derived from a murine antibody against WNV. In some embodiments, the humanized antibodies described herein comprise alterations, including, but not limited to, amino acid deletions, insertions, and modifications, of the acceptor antibody, i.e., human, heavy and/or light chain variable domain framework regions that are necessary for retaining binding specificity of the donor monoclonal antibody. In some embodiments, the framework regions of the humanized antibodies described herein do not necessarily consist of the precise amino acid sequence of the framework region of a natural occurring human antibody variable region, but contain various alterations, including, but not limited to, amino acid deletions, insertions, modifications that alter the property of the humanized antibody, for example, improve the binding properties of a humanized antibody region that is specific for the same target as the murine WNV specific antibody. In most preferred embodiments, a minimal number of alterations are made to the framework region in order to avoid large-scale introductions of non-human framework residues and to ensure minimal immunogenicity of the humanized antibody in humans. In some embodiments, the framework residues are derived from the human germline VH segment VH1-18 and JH6 and/or the human germline VL segment VK-B3. In another embodiment, the heavy chain FR3 may consist of the amino acid sequence of SEQ ID NO: 7, SEQ ID NO: 8, or SEQ ID NO: 9. In another embodiment, the light chain FR2 may consist of the amino acid sequence of SEQ ID NO: 16 or SEQ ID NO: 17. In some embodiments of the invention, there are no alterations made to the framework regions. The donor monoclonal antibody is preferably a monoclonal antibody produced by clones E16, E24, or E34, which bind WNV E antigen.

The humanized antibodies of the present invention include complete antibody molecules having full length heavy and light chains, or any fragment thereof, such as the Fab or (Fab')$_2$ fragments, a heavy chain and light chain dimer, or any minimal fragment thereof such as an Fv, an SCA (single chain antibody), and the like, specific for a WNV antigen.

The invention encompasses the production of humanized anti-WNV specific antibodies. The invention encompasses any method known in the art useful for the production of polypeptides, e.g., in vitro synthesis, recombinant DNA production, and the like. Preferably, the humanized antibodies are produced by recombinant DNA technology. The humanized WNV specific antibodies of the invention may be produced using recombinant immunoglobulin expression technology. Exemplary methods for the production of recombinant humanized antibodies of the invention may comprise the following: a) constructing, by conventional molecular biology methods, an expression vector comprising an operon that encodes an antibody heavy chain in which the CDRs and a minimal portion of the variable region framework that are required to retain donor antibody binding specificity are derived from a non-human immunoglobulin, such as the murine WNV E antigen specific monoclonal antibody, e.g., monoclonal antibody produced by clones E16, E24, or E34, which bind WNV E antigen, and the remainder of the antibody is derived from a human immunoglobulin, thereby producing a vector for the expression of a humanized antibody heavy chain; b) constructing, by conventional molecular biology methods, an expression vector comprising an operon that encodes an antibody light chain in which the CDRs and a minimal portion of the variable region framework that are required to retain donor antibody binding specificity are derived from a non-human immunoglobulin, such as the murine WNV E antigen specific monoclonal antibody, e.g., monoclonal antibody produced by clones E16, E24, or E34, which binds WNV E antigen, and the remainder of the antibody is derived from a human immunoglobulin, thereby producing a vector for the expression of humanized antibody light chain; c) transferring the expression vectors to a host cell by conventional molecular biology methods to produce a transfected host cell for the expression of humanized anti-WNV antibodies; and d) culturing the transfected cell by conventional cell culture techniques so as to produce humanized anti-WNV antibodies. Host cells may be cotransfected with two expression vectors of the invention, the first vector containing an operon encoding a heavy chain derived polypeptide and the second containing an operon encoding a light chain derived polypeptide. The two vectors may contain different selectable markers but, with the exception of the heavy and light chain coding sequences, are preferably identical. This procedure provides for equal expression of heavy and light chain polypeptides. Alternatively, a single vector may be used which encodes both heavy and light chain polypeptides. The coding sequences for the heavy and light chains may comprise cDNA or genomic DNA or both. The host cell used to express the recombinant humanized antibodies of the invention may be either a bacterial cell such as *Escherichia coli*, or, preferably, a eukaryotic cell. Preferably, a mammalian cell such as a chinese hamster ovary cell or HEK-293 may be used. The choice of expression vector is dependent upon the choice of host cell, and may be selected so as to have the desired expression and regulatory characteristics in the selected host cell. The general methods for construction of the vector of the invention, transfection of cells to produce the host cell of the invention, culture of cells to produce the humanized antibodies of the invention are all conventional molecular biology methods. Likewise, once produced, the recombinant humanized antibodies of the invention may be purified by standard procedures of the art, including cross-flow filtration, ammonium sulphate precipitation, affinity column chromatography, gel electrophoresis and the like.

In some embodiments, cell fusion methods for making monoclonal antibodies may be used in the methods of the invention such as those disclosed in U.S. Pat. No. 5,916,771, incorporated herein by reference in its entirety. Briefly, according to this method, DNA encoding the desired heavy chain (or a fragment of the heavy chain) is introduced into a first mammalian host cell, while DNA encoding the desired light chain (or a fragment of the light chain) is introduced into a second mammalian host cell. The first transformed host cell and the second transformed host cell are then combined by cell fusion to form a third cell. Prior to fusion of the first and second cells, the transformed cells may be selected for specifically desired characteristics, e.g., high levels of expression. After fusion, the resulting hybrid cell contains and expresses both the DNA encoding the desired heavy chain and the DNA encoding the desired light chain, resulting in production of the multimeric antibody.

The invention encompasses using the humanized antibodies of the present invention in conjunction with, or attached to, other antibodies or fragments thereof such as human or humanized antibodies. These other antibodies may be reactive with other markers (epitopes) characteristic for the disease against which the humanized antibodies of the invention are directed or may have different specificities chosen, for example, to recruit molecules or cells of the human immune system to the diseased cells. The humanized antibodies of the invention (or parts thereof) may be administered with such antibodies (or parts thereof) as separately administered compositions or as a single composition with the two agents linked by conventional chemical or by molecular biological methods. Additionally, the diagnostic and therapeutic value of the humanized antibodies of the invention may be augmented by labelling the humanized antibodies with labels that produce a detectable signal (either in vitro or in vivo) or with a label having a therapeutic property. Some labels, e.g., radionucleotides, may produce a detectable signal and have a therapeutic property. Examples of radionuclide labels include $^{125}I$, $^{131}I$, and $^{14}C$. Examples of other detectable labels include a fluorescent chromophore such as fluorescein, phycobiliprotein or tetraethyl rhodamine for fluorescence microscopy; an enzyme which produces a fluorescent or colored product for detection by fluorescence, absorbance, visible color or agglutination, or which produces an electron dense product for demonstration by electron microscopy; or an electron dense molecule such as ferritin, peroxidase or gold beads for direct or indirect electron microscopic visualization. Labels having therapeutic properties include drugs for the treatment of cancer, such as methotrexate and the like.

The methods of the invention also encompass polynucleotides that encode the humanized antibodies of the invention. In one embodiment, the invention provides an isolated nucleic acid sequence encoding a heavy chain or a light chain of a humanized antibody or a fragment thereof that specifically binds a WNV virus antigen, preferably a WNV E antigen. The invention also relates to a vector comprising said nucleic acid. The invention further provides a vector comprising a first nucleic acid molecule encoding a heavy chain and a second nucleic acid molecule encoding a light chain, said heavy chain and light chain being of a humanized antibody or a fragment thereof that specifically binds a WNV virus antigen. In one specific embodiment, said vector is an expression vector. The invention further provides host cells containing the vectors or polynucleotides encoding the humanized antibodies of the invention. Preferably, the invention encompasses polynucleotides encoding heavy and light chains of the humanized antibodies of the invention.

The present invention provides methods of preventing, treating and ameliorating one or more symptoms associated with flaviviral infection, particularly WNV infection, in a subject comprising administering to said subject one or more humanized antibodies or fragments thereof which immunospecifically bind to one or more flaviviral antigens, particularly WNV antigens, with high affinity and/or high avidity. The humanized antibodies of the invention are useful for prevention or treatment of a flaviviral infection, for example, as a single agent therapy. Alternatively, the humanized antibodies of the inventon may be used in a combination therapy for the treatment or prevention of a flaviviral infection with new drugs as they become available. The invention also provides a method of treating a WNV infection in a patient in need thereof, said method further comprising administering to said patient a therapeutically effective amount of one or more anti-viral agents.

In most preferred embodiments, the invention encompasses humanized antibodies (e.g., anti-E antibodies) or fragments thereof that have potent neutralizing activity as measured for example using standard methods known in the art, e.g., in vitro plaque reduction neutralization titer (PRNT) assay. Although not intending to be bound by a particular mechanism of action, the humanized antibodies of the invention may directly neutralize virus, block entry of the virus into the cell, or block fusion and uncoating of the virus inside the cell, thus treating or preventing viral infections. In some embodiments, the invention encompasses humanized antibodies which immunospecifically bind WNV-E protein such that the $PRNT_{50}$ values are at least 1/500, preferably at least 1/10,000 at a concentration of 1 mg/mL.

In yet other preferred embodiments, humanized antibodies of the invention have enhanced antibody-dependent complement mediated neutralization of WNV infected virions and trigger lysis of WNV-infected cells more effectively, as determined using standard methods known in the art and exemplified herein. Humanized antibodies are added to virus particles in the presence of complement. Subsequently, inhibition of virus activity is determined by plaque reduction assay. For complement-dependent cell lysis, humanized antibodies are added to infected cells in the presence of complement. Subsequently, cell lysis is evaluated by standard methods (e.g., propidium iodide staining and flow cytometry). Although not intending to be bound by a particular mechanism of action the humanized antibodies of the invention have enhanced clinical efficacy, therapeutically and prophylactically, as they have enhanced effector functions, neutralize virus attachment, trigger complement mediated lysis, promote clearance from the circulatory systems and prevent emergence of viral resistance. The humanized antibodies of the invention preferably have a potent in vivo inhibitory activity, i.e., protect against WNV infection by at least 50%, at least 60%, at least 70%, at least 80%, at least 90%, at least 99%. In vivo inhibitory activity as used herein refers to the activity of the humanized antibodies of the invention to neutralize virus activity, for example, by inhibiting a step in the viral life cycle, e.g., virus attachment. In vivo inhibitory activity may also refer to the ability of the antibody to reduce morbidity and mortality in an animal model of infection.

The present invention provides humanized antibodies or fragments thereof which immunospecifically bind to one or more flaviviral antigens, particularly WNV antigens, and have an apparent dissociation constant of less than 100 ng/mL as determined by a sandwich ELISA. The present invention provides humanized antibodies or fragments thereof which immuospecifically bind to one or more flaviviral antigens, particularly WNV antigens, and have an apparent dissociation constant of about 1-10 nM as measured by surface plasmon resonance (SPR) using a BIAcore sensor. The present invention provides humanized antibodies or fragments thereof which immuospecifically bind to one or more flaviviral antigens, particularly WNV antigens, and have an on rate of about $1\times10^4$, about $5\times10^4$, about $1\times10^5$, about $5\times10^5$, about $1\times10^6$, or about $5\times10^6$ and an off rate of about $1\times10^{-3}$, about $5\times10^{-4}$, about $1\times10^{-4}$, about $5\times10^{-5}$, about $1\times10^{-5}$, about $5\times10e^{-6}$, about $1\times10^{-6}$, as measured by surface plasmon resonance (SPR) using a BIAcore sensor.

The present invention provides humanized antibodies or fragments thereof which immunospecifically bind to one or more flaviviral antigens particularly WNV antigens and have a median effective concentration ($EC_{50}$) of less than 100 ng/mL, in an in vitro microneutralization assay. In particular, the present invention provides compositions for use in the prevention, treatment, or amelioration of one or more symptoms associated with a flaviviral infection, said compositions comprising one or more humanized antibodies or fragments thereof which immunospecifically bind to one or more one or more flaviviral antigens, particularly WNV antigens, and have an $EC_{50}$ of less than 0.01 nM, less than 0.025 nM, less than 0.05 nM, less than 0.1 nM, less than 0.25 nM, less than 0.5 nM, less than 0.75 nM, less than 1 nM, less than 1.25 nM, less than 1.5 nM, less than 1.75 nM, or less than 2 nM, in an in vitro microneutralization assay.

In some embodiments, the invention encompasses humanized antibodies comprising variant Fc regions that bind FcRn with an enhanced affinity, resulting in an increased antibody half life, e.g., a half-life of greater than 15 days, preferably greater than 20 days, greater than 25 days, greater than 30 days, greater than 35 days, greater than 40 days, greater than 45 days, greater than 2 months, greater than 3 months, greater than 4 months, or greater than 5 months. Although not intending to be bound by a particular mechansim of action the neonatal Fc receptor (FcRn) plays an important role in regulating the serum half-lives of IgG antibodies. A correlation has been established between the pH-dependent binding affinity of IgG antibodies to FcRn and their serum half-lives in mice. The increased half-lives of the humanized antibodies of the present invention or fragments thereof in a mammal, preferably a human, results in a higher serum titer of said humanized antibodies or antibody fragments in the mammal, and thus, reduces the frequency of the administration of said humanized antibodies or antibody fragments and/or reduces the concentration of said humanized antibodies or antibody fragments to be administered. For example, humanized antibodies or fragments thereof with increased in vivo half-lives can be generated by modifying (e.g., substituting, deleting or adding) amino acid residues identified as involved in the interaction between the Fc domain and the FcRn receptor. For example, the invention encompasses humanized antibodies comprising variant Fc regions which have at least one or more modification that enhances the affinity to FcRn, e.g., a modification of one or more amino acid residues 251-256, 285-290, 308-314, 385-389, and 428-436, or a modification at positions 250 and 428, see, e.g., Hinton et al., 2004, *J. Biol. Chem.* 279(8): 6213-6; PCT Publication No. WO 97/34631; and WO 02/060919, all of which are incorporated herein by reference in its entirety.

The invention encompasses the use of the humanized antibodies of the invention to detect the presence of one or more flaviviral antigens specifically in a biological sample. In one embodiment, the invention provides a method of diagnosis of a WNV infection in a subject comprising: (i) contacting a biological sample from said subject with an effective amount of a humanized antibody of the invention; and (ii) detecting binding of said humanized antibody or a fragment thereof, wherein detection of said detectable marker above a background or standard level indicates that said subject has a WNV infection.

The invention further provides a pharmaceutical composition comprising (i) a therapeutically or prophylactically effective amount of the humanized antibody or a fragment thereof that specifically binds one or more flaviviral antigens, e.g., WNV antigen; and (ii) a pharmaceutically acceptable carrier.

3.1 Definitions

As used herein, the term "analog" refers to a polypeptide that possesses a similar or identical function as a flaviviral, including WNV, polypeptide, a fragment of a flaviviral, including WNV polypeptide, an antibody, or antibody fragment but does not necessarily comprise a similar or identical amino acid sequence of a flaviviral, including WNV polypeptide, a fragment of a flaviviral, including WNV polypeptide, an antibody, or antibody fragment, or possess a similar or identical structure of a flaviviral, including WNV polypeptide, a fragment of a flaviviral, including WNV polypeptide, an antibody, or antibody fragment. A polypeptide that has a similar amino acid sequence refers to a polypeptide that satisfies at least one of the following: (a) a polypeptide having an amino acid sequence that is at least 30%, at least 35%, at least 40%, at least 45%, at least 50%, at least 55%, at least 60%, at least 65%, at least 70%, at least 75%, at least 80%, at least 85%, at least 90%, at least 95% or at least 99% identical to the amino acid sequence of a flaviviral, including WNV polypeptide, a fragment of a flaviviral, including WNV polypeptide, an antibody, or antibody fragment described herein; (b) a polypeptide encoded by a nucleotide sequence that hybridizes under stringent conditions to a nucleotide sequence encoding a flaviviral, including WNV, polypeptide, a fragment of a flaviviral, including WNV, polypeptide, an antibody, or antibody fragment described herein of at least 5 amino acid residues, at least 10 amino acid residues, at least 15 amino acid residues, at least 20 amino acid residues, at least 25 amino acid residues, at least 30 amino acid residues at least 40 amino acid residues, at least 50 amino acid residues, at least 60 amino acid residues, at least 70 amino acid residues, at least 80 amino acid residues, at least 90 amino acid residues, at least 100 amino acid residues, at least 125 amino acid residues, or at least 150 amino acid residues; and (c) a polypeptide encoded by a nucleotide sequence that is at least 30%, at least 35%, at least 40%, at least 45%, at least 50%, at least 55%, at least 60%, at least 65%, at least 70%, at least 75%, at least 80%, at least 85%, at least 90%, at least 95% or at least 99% identical to the nucleotide sequence encoding a flaviviral, including WNV, polypeptide, a fragment of a flaviviral, including WNV, polypeptide, an antibody, or antibody fragment described herein. A polypeptide with similar structure to a flaviviral, including WNV, polypeptide, a fragment of a flaviviral, including WNV, polypeptide, an antibody, or antibody fragment described herein refers to a polypeptide that has a similar secondary, tertiary or quaternary structure of a WNV polypeptide, a fragment of a flaviviral, including WNV, an antibody, or antibody fragment described herein. The structure of a polypeptide can determined by methods known to those skilled in the art, including but not limited to, X-ray crystallography, nuclear magnetic resonance, and crystallographic electron microscopy.

To determine the percent identity of two amino acid sequences or of two nucleic acid sequences, the sequences are aligned for optimal comparison purposes (e.g., gaps can be introduced in the sequence of a first amino acid or nucleic acid sequence for optimal alignment with a second amino acid or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=number of identical overlapping positions/ total number of positions×100%). In one embodiment, the two sequences are the same length. The determination of percent identity between two sequences can also be accomplished using a mathematical algorithm. A preferred, non-limiting example of a mathematical algorithm utilized for the comparison of two sequences is the algorithm of Karlin and Altschul, 1990, Proc. Natl. Acad. Sci. U.S.A. 87:2264-2268, modified as in Karlin and Altschul, 1993, Proc. Natl. Acad. Sci. U.S.A. 90:5873-5877. Such an algorithm is incorporated into the NBLAST and XBLAST programs of Altschul et al., 1990, J. Mol. Biol. 215:403. BLAST nucleotide searches can be performed with the NBLAST nucleotide program parameters set, e.g., for score=100, wordlength=12 to obtain nucleotide sequences homologous to a nucleic acid molecules of the present invention. BLAST protein searches can be performed with the XBLAST program parameters set, e.g., to score-50, wordlength=3 to obtain amino acid sequences homologous to a protein molecule of the present invention. To obtain gapped alignments for comparison purposes, Gapped BLAST can be utilized as described in Altschul et al., 1997, Nucleic Acids Res. 25:3389-3402. Alternatively, PSI-BLAST can be used to perform an iterated search which detects distant relationships between molecules (Id.). When utilizing BLAST, Gapped BLAST, and PSI-Blast programs, the default parameters of the respective programs (e.g., of XBLAST and NBLAST) can be used. Another preferred, non-limiting example of a mathematical algorithm utilized for the comparison of sequences is the algorithm of Myers and Miller, 1988, CABIOS 4:11-17. Such an algorithm is incorporated in the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used. The percent identity between two sequences can be determined using techniques similar to those described above, with or without allowing gaps. In calculating percent identity, typically only exact matches are counted.

As used herein, the terms "antibody" and "antibodies" refer to monoclonal antibodies, multispecific antibodies, human antibodies, humanized antibodies, synthetic antibodies, chimeric antibodies, camelized antibodies, single-chain Fvs (scFv), single chain antibodies, Fab fragments, F(ab') fragments, disulfide-linked Fvs (sdFv), intrabodies, and anti-idiotypic (anti-Id) antibodies (including, e.g., anti-Id and anti-anti-Id antibodies to antibodies of the invention), bispecific, and epitope-binding fragments of any of the above. In particular, antibodies include immunoglobulin molecules and immunologically active fragments of immunoglobulin molecules, i.e., molecules that contain an antigen binding site. Immunoglobulin molecules can be of any type (e.g., IgG, IgE, IgM, IgD, IgA and IgY), class (e.g., $IgG_1$, $IgG_2$, $IgG_3$, $IgG_4$, $IgA_1$ and $IgA_2$) or subclass.

As used herein, the term "antibodies or fragments that immunospecifically bind to a flaviviral antigen" refers to antibodies or fragments thereof that specifically bind to a flaviviral polypeptide or a fragment of a flaviviral polypeptide and do not non-specifically bind to other polypeptides. Antibodies or fragments that immunospecifically bind to a flaviviral polypeptide or fragment thereof may have cross-reactivity with other antigens. Preferably, antibodies or fragments that immunospecifically bind to a flaviviral polypeptide or fragment thereof do not cross-react with other antigens. Antibodies or fragments that immunospecifically bind to a flaviviral polypeptide can be identified, for example, by immunoassays or other techniques known to those of skill in the art.

As used herein, the term "derivative" as used herein refers to a polypeptide that comprises an amino acid sequence of a flaviviral polypeptide, including WNV polypeptide, a fragment of a flaviviral polypeptide, including WNV polypeptide, an antibody that immunospecifically binds to a flaviviral polypeptide, including WNV polypeptide, or an antibody fragment that immunospecifically binds to a flaviviral polypeptide, including WNV polypeptide, which has been altered by the introduction of amino acid residue substitutions, deletions or additions. The term "derivative" as used herein also refers to a flaviviral polypeptide, including WNV polypeptide, a fragment of a flaviviral polypeptide, including WNV polypeptide, an antibody that immunospecifically binds to a flaviviral polypeptide, including WNV polypeptide, or an antibody fragment that immunospecifically binds to a flaviviral polypeptide, including WNV polypeptide, which has been modified, i.e, by the covalent attachment of any type of molecule to the polypeptide. For example, but not by way of limitation, a flaviviral polypeptide, including WNV polypeptide, a fragment of a flaviviral polypeptide, including WNV polypeptide, an antibody, or antibody fragment may be modified, e.g., by glycosylation, acetylation, pegylation, phosphorylation, amidation, derivatization by known protecting/blocking groups, proteolytic cleavage, linkage to a cellular ligand or other protein, etc. A derivative of a flaviviral polypeptide, including WNV polypeptide, a fragment of a flaviviral polypeptide, including WNV polypeptide, an antibody, or antibody fragment may be modified by chemical modifications using techniques known to those of skill in the art, including, but not limited to, specific chemical cleavage, acetylation, formylation, metabolic synthesis of tunicamycin, etc. Further, a derivative of a flaviviral polypeptide, including WNV polypeptide, a fragment of a flaviviral polypeptide, including WNV polypeptide, an antibody, or antibody fragment may contain one or more non-classical amino acids. A polypeptide derivative possesses a similar or identical function as a flaviviral polypeptide, including WNV polypeptide, a fragment of a flaviviral polypeptide, including WNV polypeptide, an antibody, or antibody fragment described herein.

As used herein, the terms "disorder" and "disease" are used interchangeably to refer to a condition in a subject.

As used herein, the term "effective neutralizing titer" as used herein refers to the amount of antibody which corresponds to the amount present in the serum of animals that has been shown to be either clinically efficacious (in humans) or to reduce virus by 50%, 80%, 90% or 99% in, for example, mice. The 99% reduction is defined by a specific challenge of, e.g. $10^3$ pfu, $10^4$ pfu, $10^5$ pfu, $10^6$ pfu, $10^7$ pfu, $10^8$ pfu, or $10^9$ pfu of a *flavivirus*, e.g., a WNV, or by the relative amount of virus present in the blood of an animal before and after therapeutic intervention. The terms "effective neutralizing titer" or "neutralizing titer" also refers to the titer of antibody that results in a given (e.g., 90%) reduction in the number of cells producing infectious virus using the plaque reduction assay, which is an in vitro assay and evaluates the ability of a given concentration of antibody to inhibit 50 (PRNT50) or 90 (PRNT90) % of infection in BHK21 or Vero cells.

As used herein, the term "epitopes" refers to portions of a *flavivirus*, including WNV polypeptide having antigenic or immunogenic activity in an animal, preferably a mammal, and most preferably in a human. An epitope having immunogenic activity is a portion of a *flavivirus*, including WNV, polypeptide that elicits an antibody response in an animal. An epitope having antigenic activity is a portion of a *flavivirus*, including WNV, polypeptide to which an antibody immunospecifically binds as determined by any method well known in the art, for example, by the immunoassays described herein. Antigenic epitopes need not necessarily be immunogenic.

As used herein, the term "flaviviral antigen" refers to a flaviviral polypeptide or fragment thereof to which an antibody or antibody fragment immunospecifically binds. A flaviviral antigen also refers to an analog or derivative of a flaviviral polypeptide or fragment thereof to which an antibody or antibody fragment immunospecifically binds. In a preferred embodiment, a flaviviral antigen is a WNV E, a fragment, an analog or a derivative thereof to which an antibody or antibody fragment immunospecifically binds.

As used herein, the term "fragment" refers to a peptide or polypeptide comprising an amino acid sequence of at least 5 contiguous amino acid residues, at least 10 contiguous amino acid residues, at least 15 contiguous amino acid residues, at least 20 contiguous amino acid residues, at least 25 contiguous amino acid residues, at least 30 contiguous amino acid residues, at least 35 contiguous amino acid residues, at least 40 contiguous amino acid residues, at least 50 contiguous amino acid residues, at least 60 contiguous amino acid residues, at least 70 contiguous amino acid residues, at least contiguous 80 amino acid residues, at least contiguous 90 amino acid residues, at least contiguous 100 amino acid residues, at least contiguous 125 amino acid residues, at least 150 contiguous amino acid residues, at least contiguous 175 amino acid residues, at least contiguous 200 amino acid residues, or at least contiguous 250 amino acid residues of the amino acid sequence of a *flavivirus*, including WNV, polypeptide or an antibody that immunospecifically binds to a *flavivirus*, including WNV, polypeptide. In certain embodiments, a fragment refers to a peptide or polypeptide comprising an amino acid sequence of at least 5 contiguous amino acid residues, at least 10 contiguous amino acid residues, at least 15 contiguous amino acid residues, at least 20 contiguous amino acid residues, at least 25 contiguous amino acid residues, at least 40 contiguous amino acid residues, or at least 50 contiguous amino acid residues of a WNV structural or non-structural protein. In other embodiments, a fragment refers to a peptide or polypeptide comprising an amino acid of at least 5 contiguous amino acid residues, at least 10 contiguous amino acid residues, at least 15 contiguous amino acid residues, at least 20 contiguous amino acid residues, at least 25 contiguous amino acid residues, at least 30 contiguous amino acid residues, at least 35 contiguous amino acid residues, at least 40 contiguous amino acid residues, or at least 50 contiguous amino acid residues of a VH and/or VL domain of an antibody that immunospecifically binds to a *flavivirus*, including WNV, polypeptide. Preferably, a fragment of a *flavivirus*, including WNV, polypeptide or a fragment of an antibody that immunospecifically binds to a *flavivirus*, including WNV, polypeptide retains at least one function of said *flavivirus*, including WNV, polypeptide or antibody.

As used herein, the term "fusion protein" refers to a peptide, polypeptide or protein that comprises an amino acid sequence of an antibody or fragment thereof that immunospecifically binds to a *flavivirus*, including WNV, antigen and an amino acid sequence of a heterologous peptide, polypeptide or protein. In certain embodiments, a fusion protein retains the ability to immunospecifically bind to a *flavivirus*, including WNV, antigen. In other embodiments, a fusion protein does not retain the ability to immunospecifically bind to a *flavivirus*, including WNV, antigen.

As used herein, the term "host" as used herein refers to a mammal, preferably a human.

As used herein, the term "host cell" refers to the particular subject cell transfected with a nucleic acid molecule and the progeny or potential progeny of such a cell. Progeny of such a cell may not be identical to the parent cell transfected with the nucleic acid molecule due to mutations or environmental influences that may occur in succeeding generations or integration of the nucleic acid molecule into the host cell genome.

As used herein, the term "humanized antibody" refers to an immunoglobulin comprising a human framework region and one or more CDR's from a non-human (usually a mouse or rat) immunoglobulin. The non-human immunoglobulin providing the CDR's is called the "donor" and the human immunoglobulin providing the framework is called the "acceptor". Constant regions need not be present, but if they are, they must be substantially identical to human immunoglobulin constant regions, i.e., at least about 85-90%, preferably about 95% or more identical. Hence, all parts of a humanized immunoglobulin, except possibly the CDR's, are substantially identical to corresponding parts of natural human immunoglobulin sequences. A "humanized antibody" is an antibody comprising a humanized light chain and a humanized heavy chain immunoglobulin. For example, a humanized antibody would not encompass a typical chimeric antibody, because, e.g., the entire variable region of a chimeric antibody is non-human. The purpose of humanization is to construct an antibody that has the binding characteristics of a previously generated antibody that binds to a desired target but is immunologically recognized as a self antigen by the immune system of the human patient to whom it is administered. For the most part, humanized antibodies are human immunoglobulins (recipient or acceptor antibody) in which hypervariable region residues of the recipient are replaced by hypervariable region residues from a non-human species (donor antibody) such as mouse, rat, rabbit or a non-human primate having the desired specificity, affinity, and capacity. In some instances, Framework Region (FR) residues of the human immunoglobulin are replaced by corresponding non-human residues. Furthermore, humanized antibodies may comprise residues which are not found in the recipient antibody or in the donor antibody. These modifications are made to further refine antibody performance. In general, the humanized antibody will comprise substantially all of at least one, and typically two, variable domains, in which all or substantially all of the hypervariable regions correspond to those of a non-human immunoglobulin and all or substantially all of the FRs are those of a human immunoglobulin sequence. The humanized antibody optionally also will comprise at least a portion of an immunoglobulin constant region (Fc), typically that of a human immunoglobulin, that immunospecifically binds to one or more flaviviral antigens, that has been altered by the introduction of amino acid residue substitutions, deletions or additions (i.e., mutations). In some embodiments, a humanized antibody is a derivative. Such a humanized antibody comprises amino acid residue substitutions, deletions or additions in one or more non-human CDRs. The humanized antibody derivative may have substantially the same binding, better binding, or worse binding when compared to a non-derivative humanized antibody. In specific embodiments, one, two, three, four, or five amino acid residues of the CDR have been substituted, deleted or added (i.e., mutated). For further details in humanizing antibodies, see European Patent Nos. EP 239,400, EP 592,106, and EP 519,596; International Publication Nos. WO 91/09967 and WO 93/17105; U.S. Pat. Nos. 5,225,539, 5,530,101, 5,565,332, 5,585,089, 5,766,886, and 6,407,213; and Padlan, 1991, *Molecular Immunology*

28(4/5):489-498; Studnicka et al., 1994, *Protein Engineering* 7(6):805-814; Roguska et al., 1994, *Proc Natl Acad Sci USA* 91:969-973; Tan et al., 2002, *J. Immunol.* 169:1119-25; Caldas et al., 2000, *Protein Eng.* 13:353-60; Morea et al., 2000, *Methods* 20:267-79; Baca et al., 1997, *J. Biol. Chem.* 272: 10678-84; Roguska et al., 1996, *Protein Eng.* 9:895-904; Couto et al., 1995, *Cancer Res.* 55 (23 Supp):5973s-5977s; Couto et al., 1995, *Cancer Res.* 55:1717-22; Sandhu, 1994, *Gene* 150:409-10; Pedersen et al., 1994, *J. Mol. Biol.* 235: 959-73; Jones et al., 1986, *Nature* 321:522-525; Reichmann et al., 1988, *Nature* 332:323-329; and Presta, 1992, *Curr. Op. Struct. Biol.* 2:593-596.

As used herein, the term "hypervariable region" refers to the amino acid residues of an antibody which are responsible for antigen binding. The hypervariable region comprises amino acid residues from a "Complementarity Determining Region" or "CDR" (i.e., residues 24-34 (L1), 50-56 (L2) and 89-97 (L3) in the light chain variable domain and 31-35 (H1), 50-65 (H2) and 95-102 (H3) in the heavy chain variable domain (Kabat et al., *Sequences of Proteins of Immunological Interest*, 5th Ed. Public Health Service, National Institutes of Health, Bethesda, Md. (1991)) and/or those residues from a "hypervariable loop" (i.e., residues 26-32 (L1), 50-52 (L2) and 91-96 (L3) in the light chain variable domain and 26-32 (H1), 53-55 (H2) and 96-101 (H3) in the heavy chain variable domain (Chothia and Lesk, 1987, *J. Mol. Biol.* 196:901-917). "Framework Region" or "FR" residues are those variable domain residues other than the hypervariable region residues as herein defined.

As used herein, the term "in combination" refers to the use of more than one prophylactic and/or therapeutic agents. The use of the term "in combination" does not restrict the order in which prophylactic and/or therapeutic agents are administered to a subject with a disorder. A first prophylactic or therapeutic agent can be administered prior to (e.g., 1 minute, 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 1 minute, 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second prophylactic or therapeutic agent to a subject which had, has, or is susceptible to a disorder. The prophylactic or therapeutic agents are administered to a subject in a sequence and within a time interval such that the agent of the invention can act together with the other agent to provide an increased benefit than if they were administered otherwise. Any additional prophylactic or therapeutic agent can be administered in any order with the other additional prophylactic or therapeutic agents.

An "isolated" or "purified" antibody or fragment thereof is substantially free of cellular material or other contaminating proteins from the cell or tissue source from which the protein is derived, or substantially free of chemical precursors or other chemicals when chemically synthesized. The language "substantially free of cellular material" includes preparations of an antibody or antibody fragment in which the antibody or antibody fragment is separated from cellular components of the cells from which it is isolated or recombinantly produced. Thus, an antibody or antibody fragment that is substantially free of cellular material includes preparations of antibody or antibody fragment having less than about 30%, 20%, 10%, or 5% (by dry weight) of heterologous protein (also referred to herein as a "contaminating protein"). When the antibody or antibody fragment is recombinantly produced, it is also preferably substantially free of culture medium, i.e., culture medium represents less than about 20%, 10%, or 5% of the volume of the protein preparation. When the antibody or antibody fragment is produced by chemical synthesis, it is preferably substantially free of chemical precursors or other chemicals, i.e., it is separated from chemical precursors or other chemicals which are involved in the synthesis of the protein. Accordingly such preparations of the antibody or antibody fragment have less than about 30%, 20%, 10%, 5% (by dry weight) of chemical precursors or compounds other than the antibody or antibody fragment of interest. In a preferred embodiment, humanized antibodies of the invention or fragments thereof are isolated or purified.

An "isolated" nucleic acid molecule is one which is separated from other nucleic acid molecules which are present in the natural source of the nucleic acid molecule. Moreover, an "isolated" nucleic acid molecule, such as a cDNA molecule, can be substantially free of other cellular material, or culture medium when produced by recombinant techniques, or substantially free of chemical precursors or other chemicals when chemically synthesized. In a preferred embodiment, nucleic acid molecules encoding humanized antibodies of the invention or fragments thereof are isolated or purified.

As used herein, the terms "manage," "managing" and "management" refer to the beneficial effects that a subject derives from administration of a prophylactic or therapeutic agent, which does not result in a cure of the disease. In certain embodiments, a subject is administered one or more prophylactic or therapeutic agents to "manage" a disease so as to prevent the progression or worsening of the disease.

As used herein, the terms "nucleic acids" and "nucleotide sequences" include DNA molecules (e.g., cDNA or genomic DNA), RNA molecules (e.g., mRNA), combinations of DNA and RNA molecules or hybrid DNA/RNA molecules, and analogs of DNA or RNA molecules. Such analogs can be generated using, for example, nucleotide analogs, which include, but are not limited to, inosine or tritylated bases. Such analogs can also comprise DNA or RNA molecules comprising modified backbones that lend beneficial attributes to the molecules such as, for example, nuclease resistance or an increased ability to cross cellular membranes. The nucleic acids or nucleotide sequences can be single-stranded, double-stranded, may contain both single-stranded and double-stranded portions, and may contain triple-stranded portions, but preferably is double-stranded DNA.

As used herein, the phrases "a peptide, polypeptide or protein comprising a variable or hypervariable region of an antibody of the invention", "a peptide, polypeptide or protein comprising a VH or VL domain of an antibody of the invention", "a peptide, polypeptide or protein comprising one or more CDRs having an amino acid sequence of one or more of the CDRs listed in SEQ ID NOS: 1, 2, 3, 11, 12, 13, 27, 28, 29, 34, 39, and 40, and analogous phrases, refer to fusion proteins.

As used herein, the terms "prevent", "preventing" and "prevention" refer to the prevention of the occurrence and/or recurrence or onset of one or more symptoms of a disorder in a subject resulting from the administration of a prophylactic or therapeutic agent.

As used herein, the terms "prophylactic agent" and "prophylactic agents" refer to any agent(s) which can be used in the prevention of a disorder, or prevention of recurrence or spread of a disorder. A prophylactically effective amount may also refer to the amount of the prophylactic agent that provides a prophylactic benefit in the prevention of disease. Further, a prophylactically effective amount with respect to a prophylactic agent of the invention means that amount of prophylactic agent alone, or in combination with other agents, that provides a prophylactic benefit in the prevention of disease. Used in connection with an amount of an antibody of the invention, the term can encompass an amount that improves overall prophylaxis or enhances the prophylactic efficacy of or synergizes with another prophylactic agent, such as, but not limited to, a therapeutic antibody.

In certain embodiments of the invention, a "prophylactically effective serum titer" is the serum titer in a mammal, preferably a human, that reduces the incidence of a flaviviral infection in said mammal. Preferably, the prophylactically effective serum titer reduces the incidence of flaviviral infections in humans with the greatest probability of complications resulting from flaviviral infection (e.g., a human infant, or an elderly human or a human with an impaired immune system). In certain other embodiments of the invention, a "prophylactically effective serum titer" is the serum titer in a mouse model that results in a flaviviral titer 3 days after challenge with $10^3$ pfu that is 99% lower than the flaviviral titer 3 days after challenge with $10^3$ pfu of flaviviral in the same strain of mouse not administered an antibody or antibody fragment that immunospecifically binds to a flaviviral antigen.

As used herein, the phrase "side effects" encompasses unwanted and adverse effects of a prophylactic or therapeutic agent. Adverse effects are always unwanted, but unwanted effects are not necessarily adverse. An adverse effect from a prophylactic or therapeutic agent might be harmful or uncomfortable or risky. Side effects from chemotherapy include, but are not limited to, gastrointestinal toxicity such as, but not limited to, early and late-forming diarrhea and flatulence, nausea, vomiting, anorexia, leukopenia, anemia, neutropenia, asthenia, abdominal cramping, fever, pain, loss of body weight, dehydration, alopecia, dyspnea, insomnia, dizziness, mucositis, xerostomia, and kidney failure, as well as constipation, nerve and muscle effects, temporary or permanent damage to kidneys and bladder, flu-like symptoms, fluid retention, and temporary or permanent infertility. Side effects from radiation therapy include, but are not limited to, fatigue, dry mouth, and loss of appetite. Side effects from biological therapies/immunotherapies include, but are not limited, to rashes or swellings at the site of administration, flu-like symptoms such as fever, chills and fatigue, digestive tract problems and allergic reactions. Side effects from hormonal therapies include, but are not limited to, nausea, fertility problems, depression, loss of appetite, eye problems, headache, and weight fluctuation. Additional undesired effects typically experienced by patients are numerous and known in the art, see, e.g., the *Physicians' Desk Reference* (56th ed., 2002), which is incorporated herein by reference in its entirety.

As used herein, the terms "single-chain Fv" or "scFv" refer to antibody fragments that comprise the VH and VL domains of the antibody, wherein these domains are present in a single polypeptide chain. Generally, the Fv polypeptide further comprises a polypeptide linker between the VH and VL domains which enables the scFv to form the desired structure for antigen binding. For a review of scFv, see Pluckthun in *The Pharmacology of Monoclonal Antibodies*, vol. 113, Rosenburg and Moore eds. Springer-Verlag, New York, pp. 269-315 (1994). In specific embodiments, scFvs include bi-specific scFvs and humanized scFvs.

As used herein, the term "specifically binds to a flaviviral antigen" and analogous terms refer to antibodies or fragments thereof that specifically bind to a flaviviral antigen or fragment thereof and do not specifically bind to other viral antigens. Examples of flaviviral antigens include, but are not limited to, structural proteins, e.g., C, M, and E, and non-structural proteins, e.g., NS1, NS2A, NS2B, NS3, NS4A, NS4B and NS5. An antibody that specifically binds to a flaviviral antigen or fragment thereof may bind to other peptides or polypeptides with lower affinity as determined by, e.g., immunoassays, BIAcore, or other assays known in the art. Preferably, antibodies or fragments that specifically bind to to a flaviviral antigen or fragment thereof do not cross-react with other antigens. Antibodies or fragments that specifically bind to a flaviviral antigen or fragment thereof can be identified, for example, by immunoassays, BIAcore, or other techniques known to those of skill in the art. An antibody or a fragment thereof binds specifically to a flaviviral antigen or fragment thereof with higher affinity than to any cross-reactive antigen as determined using experimental techniques, such as western blots, radioimmunoassays (RIA) and enzyme-linked immunosorbent assays (ELISAs). See, e.g., Paul, ed., 1989, *Fundamental Immunology Second Edition*, Raven Press, New York at pages 332-336 for a discussion regarding antibody specificity.

As used herein, the terms "subject" and "patient" are used interchangeably. As used herein, a subject is preferably a mammal such as a non-primate (e.g., cows, pigs, horses, cats, dogs, rats etc.) and a primate (e.g., monkey and human), most preferably a human.

As used herein, a "therapeutically effective amount" refers to that amount of the therapeutic agent sufficient to treat or manage flaviviral infection or to enhance the therapeutic efficacy of another therapy, e.g., therapeutic antibody, vaccine therapy, etc. A therapeutically effective amount may refer to the amount of therapeutic agent sufficient to delay or minimize the onset of disease. A therapeutically effective amount may also refer to the amount of the therapeutic agent that provides a therapeutic benefit in the treatment or management of a disease. Further, a therapeutically effective amount with respect to a therapeutic agent of the invention means that amount of therapeutic agent alone, or in combination with other therapies, that provides a therapeutic benefit in the treatment or management of a disease, e.g., sufficient to enhance the therapeutic efficacy of a therapeutic antibody sufficient to treat or manage a disease. Used in connection with an amount of an antibody of the invention, the term can encompass an amount that improves overall therapy, reduces or avoids unwanted side effects, or enhances the therapeutic efficacy of or synergizes with another therapeutic agent.

In certain embodiments of the invention, a "therapeutically effective serum titer" is the serum titer in a mammal, preferably a human, that reduces the severity, the duration and/or the symptoms associated with a flaviviral infection in said mammal. Preferably, the therapeutically effective serum titer reduces the severity, the duration and/or the number of symptoms associated with flaviviral infections in humans with the greatest probability of complications resulting from a flaviviral infection (e.g., a human infant, an elderly human or a human with an impaired immune system). In certain other embodiments of the invention, a "therapeutically effective serum titer" is the serum titer in a mouse model that results in a flaviviral titer 3 days after challenge with $10^2$, $10^3$ or $10^4$ pfu that is 99% lower than the flaviviral titer 3 days after challenge with $10^2$, $10^3$ or $10^4$ pfu of flaviviral in the same strain of mouse not administered an antibody or antibody fragment that immunospecifically binds to a flaviviral antigen.

As used herein, the terms "treat," "treating" and "treatment" refer to the eradication, reduction or amelioration of symptoms of a disease or disorder related to a flaviviral infection, e.g., a WNV infection.

4. BRIEF DESCRIPTION OF THE DRAWINGS

FIGS. 1A and B AMINO ACID ALIGNMENTS OF E16 HEAVY AND LIGHT CHAINS

A. The comparison of the murine WNV E16 VH (muE16VH) and the humanized WNV E16 VH (huE16VH- 1). Framework regions from the human VH1-18 segment used in the humanization scheme are indicated.

B. The comparison of the murine WNV E16 VL (muE16VL) and the humanized WNV E16 VL (huE16VL-1). Framework regions from the human VK-B3 segment used in the humanization scheme are indicated.

FIGS. 2A AND B BINDING OF CHIMERIC, HUMANIZED OR HYBRID ANTI-WNV MAB E16 TO ANTIGEN

A. Antibody binding in direct antigen ELISA. Chimeric, humanized, chE16LC/huE16HC or huE16LC/chE16HC E16 antibody was obtained from conditioned media of transfected HEK-293 cultures. Conditioned media was serially diluted into wells of a 96 well plate previously coated with 100 ng/well of WNV E-protein Domain III. Binding was detected by HRP conjugated F(ab')$_2$ goat anti human IgG F(ab')$_2$ specific secondary antibody, and the OD$_{450}$ nm was read by SOFTmax program.

B. Antibody binding in antigen capture ELISA. Chimeric, humanized, chE16LC/huE16HC or huE16LC/chE16HC E16 antibody was obtained from conditioned media of transfected HEK-293 cultures. A 96 well plate was prepared by coating each well with murine anti-WNV E protein antibody E9 followed by incubation with 2.5 ng/well of WNV E-protein Domain III. Conditioned media was serially diluted into the prepared wells and binding detected by HRP conjugated F(ab')$_2$ goat anti human IgG F(ab')$_2$ specific secondary antibody. The OD$_{450}$ nm was read by SOFTmax program.

FIGS. 3A AND B BINDING OF HUMANIZED ANTI-WNV MAB E16 LIGHT CHAIN VARIANTS TO ANTIGEN

A. Antibody binding in direct antigen ELISA. Chimeric and light-chain variants of humanized E16 antibody, huE16HC/huE16LC (huE16-1.1) or huE16HC/huE16LC-2 Y49S (huE16-1.2), were obtained from conditioned media of transfected HEK-293 cultures. Conditioned media was serially diluted into wells of a 96 well plate previously coated with 100 ng/well of WNV E-protein Domain III. Binding was detected by HRP conjugated F(ab')$_2$ goat anti human IgG F(ab')$_2$ specific secondary antibody, and the OD$_{450}$ nm was read by SOFTmax program.

B. Antibody binding in antigen capture ELISA. Chimeric and light-chain variants of humanized E16 antibody, huE16HC/huE16LC (huE16-1.1) or huE16HC/huE16LC-2 Y49S (huE16-1.2), were obtained from conditioned media of transfected HEK-293 cultures. A 96 well plate was prepared by coating each well with murine anti-WNV E protein antibody E9 followed by incubation with 2.5 ng/well of WNV E-protein Domain III. Conditioned media was serially diluted into the prepared wells and binding detected by HRP conjugated F(ab')$_2$ goat anti human IgG F(ab')$_2$ specific secondary antibody. The OD$_{450}$ nm was read by SOFTmax program.

Figure 4:
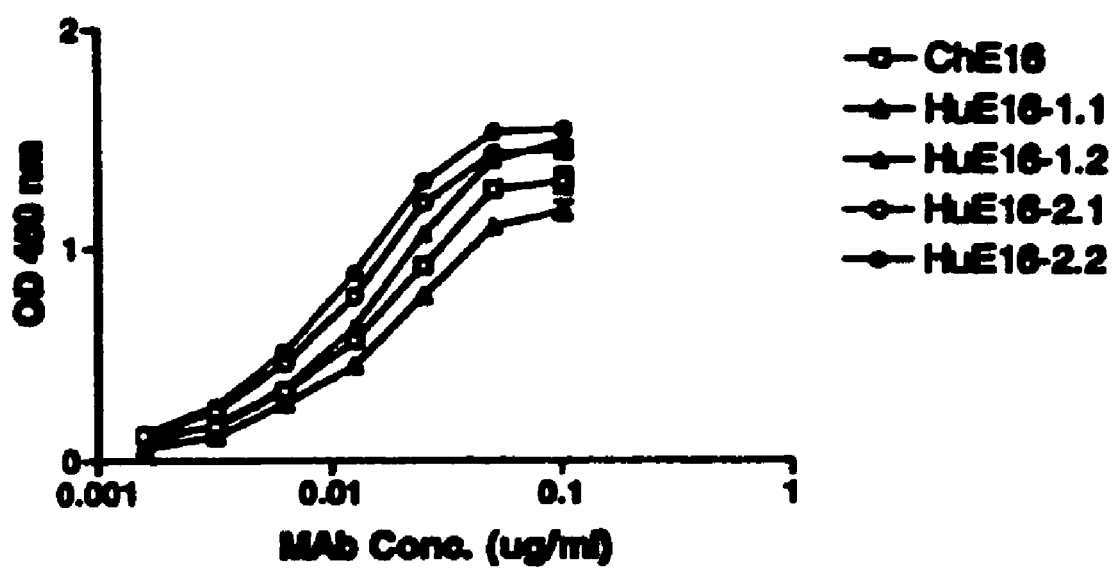
Figure 5:
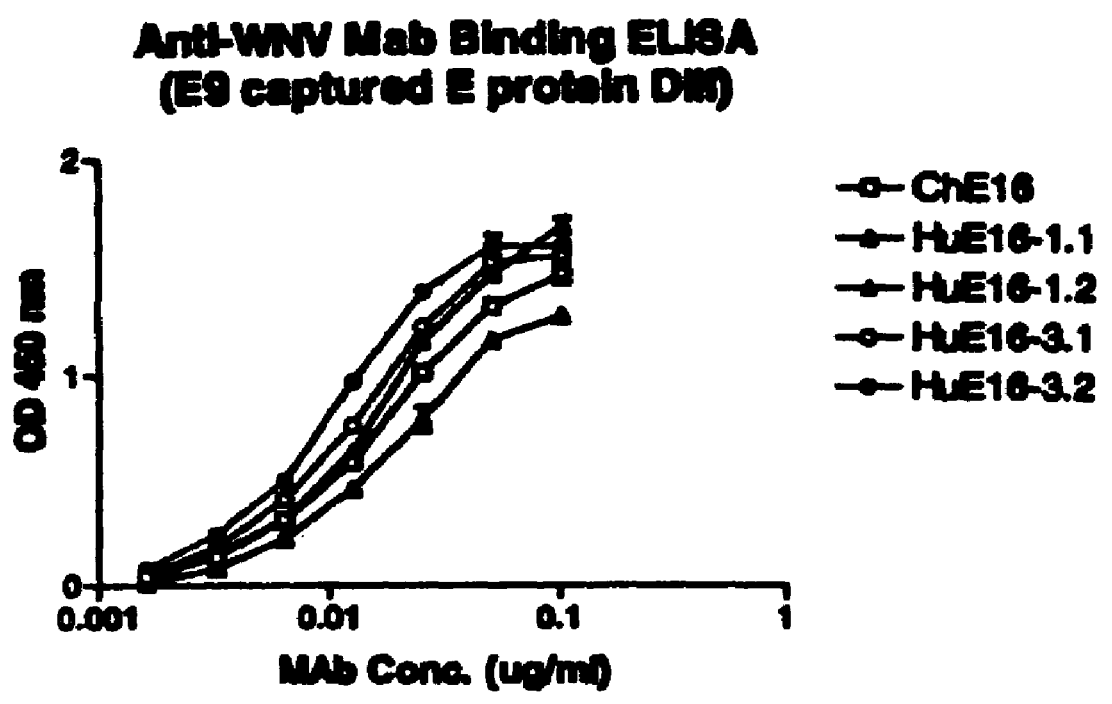

FIGS. 4 AND 5 BINDING OF HUMANIZED ANTI-WNV MAB E16 HEAVY CHAIN VARIANTS TO ANTIGEN

Figure 3B:
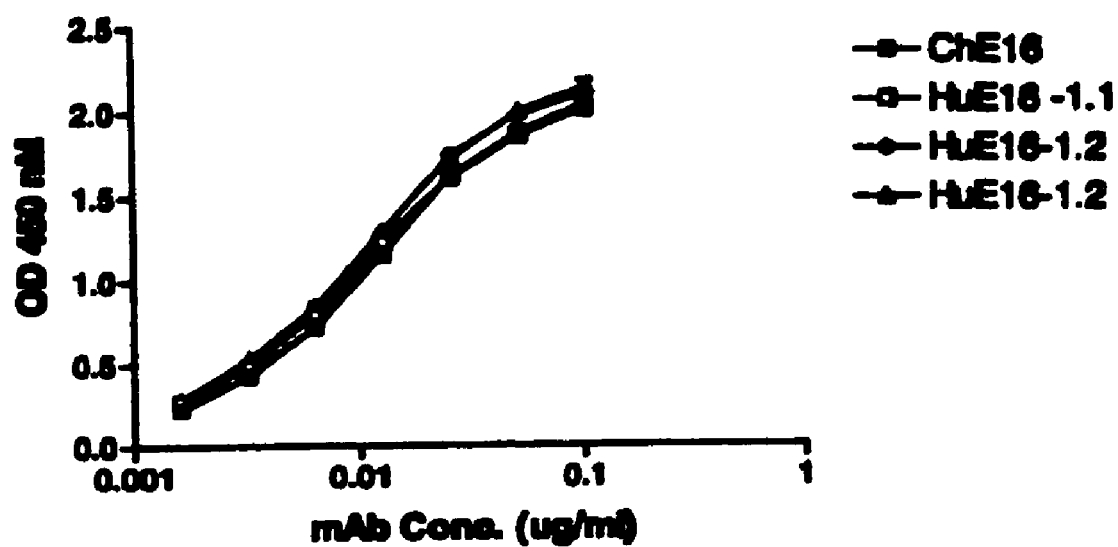

Antibody binding in antigen capture ELISA. A 96 well plate was prepared by coating each well with murine anti-WNV E protein antibody E9 followed by incubation with 2.5 ng/well of WNV E-protein Domain III. Conditioned media was serially diluted into the prepared wells and binding detected by HRP conjugated F(ab')$_2$ goat anti human IgG F(ab')$_2$ specific secondary antibody. The OD$_{450}$ nm was read by SOFTmax program. Results from FIG. 3B are included for purposes of comparison.

4. Chimeric and heavy-chain variants of humanized E16 antibody; huE16HC-2 V67A, M69F, T71A/huE16LC (huE16-2.1) or huE16HC-2 V67A, M69F, T71A/huE16LC2 Y49S (huE16-2.2); obtained from conditioned media of transfected HEK-293 cultures. Results from FIG. 3B are included for purposes of comparison.

5. Chimeric and heavy-chain variants of humanized E16 antibody, huE16HC-2 T71A/huE16LC (huE16-3.1) or huE16HC-2 T71A/huE16LC2 Y49S (huE16-3.2), obtained from conditioned media of transfected HEK-293 cultures. Results from FIG. 3B are included for purposes of comparison.

FIGS. 6, 7, 8, 9, AND 10 PROPHYLAXIS AND THERAPEUTIC STUDIES OF ANTI-WNV ANTIBODIES IN A MURINE MODEL OF WNV

To establish the WNV disease model, 5-week old mice were inoculated with $10^2$ PFU WNV via footpad injection.

6. Prophylaxis of immune human γ-globulin. Treatment with a single IP 15 mg dose of purified immune human γ-globulin against WNV immediately prior to inoculation (day 0) or at days 1, 2, 3, 4, 5 (D0, D1, D2, D3, D4, D5, respectively) post-infection.

7A. Prophylaxis of murine E16, E24 and E34. Treatment at day 2 post-infection with a single IP 0.5 mg dose of murine anti-WNV mAb E16, E24 or E34. A single IP 0.5 mg dose of irrelevant humanized IgG, anti-SARSORF7a, served as control.

7B. Dose response of murine anti-WNV mAb E16 prophylaxis. Treatment at day 4 post-infection with a single 0.8, 4, 20, 100 or 500 μg IP dose of murine anti-WNV mAb E16.

8. Prophylaxis of murine E16, E24 and E34. Treatment at day 5 post-infection with a single IP 5 mg dose of murine anti-WNV mAb E16 or E24.

9A. Dose response of humanized anti-WNV mAb E16H-173 (huE16-1.2) therapy. Treatment at day 2 post-infection with a single 4, 20 or 100 μg IP dose of humanized anti-WNV mAb E16H-173.

9B. Dose response of humanized anti-WNV mAb E16H-167 (huE16-1.1) therapy. Treatment at day 2 post-infection with a single 4, 20 or 100 μg IP dose of humanized anti-WNV mAb E16H-167.

10. Dose response of humanized anti-WNV mAB hE16-3.2 prophylaxis. Prophylaxis at one day pre-infection with a 0.03, 0.1, 0.3, 1.0 or 3.0 mg/kg IP dose of humanized anti-WNV mAB hE16-3.2.

5. DETAILED DESCRIPTION OF THE INVENTION

The present invention provides humanized antibodies, or antigen binding fragments thereof that immunospecifically bind to one or more flaviviral antigens, preferably WNV antigens. Preferably, the humanized antibodies of the invention or fragments thereof immunospecifically bind to one or more flaviviral antigens, preferably WNV antigens, regardless of the strain of the virus. In some embodiments, the humanized antibodies of the invention bind with similar affinities and/or avidities to all WNV strains including lineage I and II strains such as North American West Nile strains including those related to the New York 1999 strain.

The present invention provides numerous humanized antibodies specific for WNV based on the discovery that the CDR regions of the murine monoclonal antibody could be spliced into a human acceptor framework so as to produce a humanized recombinant antibody specific for the WNV. Preferred humanized WNV specific antibodies contain one or more additional changes in the framework region (or in other regions) to increasing binding for WNV. Particularly preferred embodiments of the invention are the exemplified humanized antibody molecules that have superior binding properties for WNV.

In most preferred embodiments, the present invention provides humanized antibodies that immunospecifically bind a structural protein of WNV, e.g., E protein, for prevention and/or treatment of WNV infections in mammals. In a specific embodiment, the humanized antibodies of the invention bind to the ectodomain of WNV E protein, as determined by standard methods known to one skilled in the art and exemplified herein, e.g., yeast two hybrid system, ELISA, immunoprecipitation, immunoblotting. In another specific embodiment, the humanized antibodies of the invention bind to domain III of the WNV E protein, comprising amino acids 290 to 415. In other specific embodiments, the humanized antibodies of the invention bind to the viral fusion peptide in domain II, comprising amino acids 98-109, or to other regions in domain I (e.g., amino acids 1-52, 132-193, and 280-290), or domain II (e.g., amino acids 52-132 and 193-280).

In some embodiments, the humanized antibodies of the invention bind to one or more epitopes of a structural protein and/or one or more epitopes of a non-structural protein of a WNV. In other embodiments, the present invention also provides humanized antibodies or fragments thereof that differentially or preferentially bind to flaviviral antigens from one strain of the *flavivirus* versus another strain.

In most preferred embodiments, the invention encompasses humanized antibodies or fragments thereof that have potent neutralizing activity as measured for example using standard methods known in the art, e.g., in vitro plaque reduction neutralization titer (PRNT) assay. Although not intending to be bound by a particular mechanims of action the humanized antibodies of the invention may directly neutralize virus or block entry of the virus into the cell, thus treating or preventing viral infections. In some embodiments, the invention encompasses humanized antibodies which immunospecifically bind WNV-E protein such that the $PRNT_{50}$ values are at least 1/500, preferably at least 1/10,000 at a concentration of 1 mg/mL. PRNT assays may be done using any method known to one skilled in the art, such as those described in Diamond et al., 2003, J. Virol. 77: 2578-2586, which is incorporated herein by reference in its entirety.

In yet other preferred embodiments, humanized antibodies of the invention have enhanced antibody-dependent complement mediated neutralization of WNV virions and trigger lysis of WNV-infected cells more effectively, as determined using standard methods known in the art and exemplified herein, such as complement fixation and cell viability assays. Although not intending to be bound by a particular mechanism of action the humanized antibodies of the invention have enhanced clinical efficacy, therapeutically and prophylactically as they have enhanced effector functions, neutralize virus attachment, trigger complement mediated lysis, promote clearance from the circulatory systems and prevent emergence of viral resistance. The humanized antibodies of the invention preferably have a potent in vivo inhibitory activity, i.e., protect against WNV infection by at least 50%, at least 60%, at least 70%, at least 80%, at least 90%, at least 99%.

The present invention provides humanized antibodies or fragments thereof which immunospecifically bind to one or more flaviviral antigens particularly WNV antigens and have an apparent dissociation constant of about 1-10 nM, as determined by a sandwich ELISA. The present invention provides humanized antibodies or fragments thereof which immuospecifically bind to one or more flaviviral antigens particularly WNV antigens and have an $K_{on}$ rate of about $1\times10^4$, about $5\times10^4$, about $1\times10^5$, about $5\times10^5$, about $1\times10^6$, or about $5\times10^6$ and a $K_{off}$ rate of about $1\times10^{-3}$, about $5\times10^{-4}$, about $1\times10^{-4}$, about $5\times10^{-5}$, about $1\times10^{-5}$, about $5\times10^{-6}$, or about $1\times10^{-6}$ as measured by surface plasmon resonance (SPR) using a BIAcore sensor.

The present invention provides humanized antibodies or fragments thereof which immunospecifically bind to one or more flaviviral antigens particularly WNV antigens and have a median effective concentration ($EC_{50}$) of less than 1 μg/ml, in an in vitro microneutralization assay. In particular, the present invention provides compositions for use in the prevention, treatment or amelioration of one or more symptoms associated with a flaviviral infection, said compositions comprising one or more humanized antibodies or fragments thereof which immunospecifically bind to one or more one or more flaviviral antigens particularly WNV antigens and have an $EC_{50}$ of less than 0.01 nM, less than 0.025 nM, less than 0.05 nM, less than 0.1 nM, less than 0.25 nM, less than 0.5 nM, less than 0.75 nM, less than 1 nM, less than 1.25 nM, less than 1.5 nM, less than 1.75 nM, or less than 2 nM, in an in vitro microneutralization assay.

The present invention also provides humanized antibodies which immunospecifically bind to one or more flaviviral antigens, particularly WNV antigens, and have increased in vivo half-lives (by for example 30 days) relative to known antibodies. In particular, the present invention encompasses humanized antibodies which immunospecifically bind to one or more flaviviral antigens, particularly WNV antigens, and have increased in vivo half-lives relative to known antibodies, said increased half-lives resulting from one or more modifications (e.g., substitutions, deletions, or insertions) in amino acid residues identified to be involved in the interaction of the Fc domain of said antibodies and the FcRn receptor. The present invention also encompasses pegylated humanized antibodies and fragments thereof which immunospecifically bind to one or more flaviviral antigens, particularly WNV antigens, and have increased in vivo half-lives relative to known antibodies. The increased in vivo half-lives of humanized antibodies or fragments thereof which immunospecifically bind to one or more flaviviral antigens particularly WNV antigens reduce the dosage and/or frequency of administration of said humanized antibodies or fragments thereof to a subject.

In one specific preferred embodiment, the humanized antibodies of the invention bind to the WNV E protein. In another specific embodiment, the humanized antibodies of the invention specifically or selectively recognize one or more epitopes of WNV E protein. Another embodiment of the invention encompasses the use of phage display technology, DNA shuffling, or any other similar method known to one skilled in the art, to increase the affinity of the humanized antibodies of the invention for WNV E protein. Any screening method known in the art can be used to identify mutant antibodies with increased avidity for WNV E protein (e.g., ELISA). In another specific embodiment, humanized antibodies of the invention are screened using antibody screening assays well known in the art (e.g., BIACORE assays) to identify antibodies with $K_{off}$ rate of about $1\times10^{-3}$, about $5\times10^{-4}$, about $1\times10^{-4}$, about $5\times10^{-5}$, about $1\times10^{-5}$, about $5\times10^{-6}$, or about $1\times10^{-6}$.

The present invention provides humanized antibodies or fragments thereof which immunospecifically bind to one or more flaviviral antigens particularly WNV antigens and have an association rate constant or $k_{on}$ rate (antibody (Ab)+antigen (Ag)$^{k_{on}}$→Ab-Ag) of at least $1 \times 10^4$, about $5 \times 10^4$, about $1 \times 10^5$, about $5 \times 10^5$, about $1 \times 10^6$, or about $5 \times 10^6$. In particular, the present invention provides compositions for use in the prevention, treatment or amelioration of one or more symptoms associated with a flaviviral infection, said compositions comprising one or more humanized antibodies or fragments thereof which immunospecifically bind to one or more one or more flaviviral antigens particularly WNV antigens and have an a $k_{on}$ rate of at least $1 \times 10^4$, about $5 \times 10^4$, about $1 \times 10^5$, about $5 \times 10^5$, about $1 \times 10^6$, or about $5 \times 10^6$.

The present invention provides methods for treating, preventing, or ameliorating a flaviviral infection by administration of one or more humanized antibodies of the invention. The present invention also provides methods of preventing, treating and ameliorating one or more symptoms associated with flaviviral infection, particularly WNV infection, in a subject comprising administering to said subject one or more humanized antibodies or fragments thereof which immunospecifically bind to one or more flaviviral antigens particularly WNV antigens with high affinity and/or high avidity. The humanized antibodies of the invention are useful for prevention or treatment of a flaviviral infection for example, in one embodiment, as a single agent therapy. These methods can be used for achieving or inducing a prophylactically and/or therapeutically effective response against flaviviral infections including, but not limited to, Japanese Encephalitis (JE, e.g., JE SA14-14-2), Dengue (DEN, e.g., any of the Dengue serotypes 1-4); Murray Valley encephalitis, St Louis Encephalitis, West Nile, Tick borne encephalitis, Hepatitis C viruses, Kunjin virus, Powassan virus, Kyasanur Forest Disease virus, yellow fever virus, and Omsk Hemorrhagic Fever Virus. The methods of the instant invention are more effective prophylactically and therapeutically compared to conventional modes of treatment or prophylaxis of flaviviral infections, particularly WNV infections, including, but not limited to, passive administration of immune serum or purified polyclonal antibody, administration of γ-globulin, interferon alpha therapy and IVIG therapies. The methods and compositions of the present invention are particularly effective for prophylaxis against flaviviral infections in a human population which is at an increased risk of flaviviral infections. In specific preferred embodiments, the methods and compositions of the present invention are particularly useful to a human population which is at an increased risk for WNV infection including, but not limited to, human infants, elderly humans, and human patients with an impaired immune system.

Although not intending to be bound by a particular mechanism of action, humanized antibodies of the invention are more effective than current treatments against flaviviral infections such as, for example, treatment using IVIG for WNV infections from donors with high neutralizing titres. Because IVIG is made from human blood plasma, it has an inherent risk of transmitting an infectious agent. Although the source plasma donors are screened and the plasma is solvent/detergent treated to inactivate viruses such as HIV, virus removal and inactivation must be validated to remove a wide variety of agents as a precaution; and the list of agents that can be transmitted by blood grows with every emerging infection. Even with all these precautions, there is never 100% assurance of elimination of infectious agents. Finally, most preparations have excipients such as human albumin, another blood product, and sucrose, which can increase the risk of adverse events. Another limitation of IVIG can be the large volumes needed, especially in patients with cardiac or renal co-morbidities. In using a specific immune globulin from vaccinated donors, while enriched for antibodies to the target agent, most of the preparation contains unrelated antibodies. The present invention cures the deficiency of current IVIG regimens. Humanized antibodies of the instant invention offer an inherently safer and potentially more efficacious alternative to IVIG for the prevention and treatment of flaviviral infections such as those caused by WNV. Additional benefits of the humanized antibodies of the invention include, but are not limited to, their ability to be grown in tissue culture under defined conditions with chemically defined medium without the addition of animal or human-derived proteins; unlike polyclonal serum, they can be selected for desired properties including epitope specificity, affinity and neutralizing capacity, allowing lower doses; and they can be formulated at high concentration to reduce the volume of administration.

In a specific embodiment, the invention encompasses methods for treating, preventing, or ameliorating a WNV infection comprising administering a first antibody that immunospecifically binds a structural protein of WNV, e.g., E protein, and a second antibody that binds a non-structural protein of WNV, e.g., NS1 protein. In other specific embodiments, the invention encompasses methods for treating, preventing, or ameliorating a WNV infection comprising administering a first antibody that immunospecifically binds an epitope of a structural protein of WNV, e.g., E protein, and a second antibody that binds the same structural protein of WNV but binds at a distinct site.

The invention also encompasses polynucleotides that encode the humanized antibodies of the invention. In one embodiment, the invention provides an isolated nucleic acid sequence encoding a heavy chain or a light chain of a humanized antibody or a fragment thereof that specifically binds one or more flaviviral antigens, particularly WNV antigens. The invention also relates to a vector comprising said nucleic acid. The invention further provides a vector comprising a first nucleic acid molecule encoding a heavy chain and a second nucleic acid molecule encoding a light chain, said heavy chain and light chain being of a humanized antibody or a fragment thereof that specifically binds one or more flaviviral antigens, particularly WNV antigens. In one specific embodiment, said vector is an expression vector. The invention further provides host cells containing vectors containing polynucleotides encoding the humanized antibodies of the invention. Preferably, the invention encompasses polynucleotides encoding heavy and light chains of the humanized antibodies of the invention.

The invention further provides methods for the production of humanized antibodies of the invention or fragments thereof. The humanized antibodies of the invention or fragments thereof can be produced by any method known in the art for the production of humanized antibodies, in particular, by secretion from cultured hybridoma cells, chemical synthesis or by recombinant expression techniques known in the art. In one specific embodiment, the invention relates to a method for recombinantly producing the humanized antibodies of the invention, said method comprising: (i) culturing under conditions suitable for the expression of said antibody in a medium, a host cell containing a first nucleic acid molecule, operably linked to a heterologous promoter and a second nucleic acid operably linked to the same or a different heterologous promoter, said first nucleic acid and second nucleic acid encoding a heavy chain and a light chain, respectively, of an antibody or a fragment thereof that specifically binds one or more flaviviral antigens; and (ii) recovery of said antibody from said medium.

The invention further provides a pharmaceutical composition comprising (i) a therapeutically or prophylactically effective amount of a humanized antibody of the invention; and (ii) a pharmaceutically acceptable carrier.

In another embodiment, the invention provides a method of diagnosis of a flaviviral infection in a subject comprising: (i) contacting a biological sample from said subject with an effective amount of a humanized antibody of the invention; and (ii) detecting binding of said humanized antibody or a fragment thereof, wherein detection of said detectable marker above a background or standard level indicates that said subject has a flaviviral infection.

5.1 Antibodies

The present invention encompasses humanized antibodies, or antigen binding fragments thereof, that immunospecifically bind to one or more flaviviral antigens, preferably WNV antigens. Preferably, the humanized antibodies of the invention or fragments thereof immunospecifically bind to one or more flaviviral antigens, preferably WNV antigens regardless of the strain of the virus. In some embodiments, the humanized antibodies of the invention bind with similar affinities and/or avidities to all WNV strains including lineage I and II strains such as North American strains (e.g., the New York 1999 and related strains).

In most preferred embodiments, the present invention provides humanized antibodies that immunospecifically bind a structural protein of WNV, e.g., E protein, for prevention and/or treatment of WNV infections in avians or mammals, particularly humans. In a specific embodiment, the isolated humanized antibodies of the invention bind to the ectodomain of WNV E protein, as determined by standard methods known to one skilled in the art and exemplified herein, e.g., ELISA, flow cytometry, immunoprecipitation, immunoblot. In another specific embodiment, the isolated humanized antibodies of the invention bind to domain III of the WNV E protein, comprising amino acids 290 to 415, as determined by standard methods known to one skilled in the art and exemplified herein, e.g., ELISA, immunoprecipitation, immunoblotting.

In some embodiments, the humanized antibodies of the invention bind to one or more epitopes of a structural protein and/or one or more epitopes of a non-structural protein of an WNV. In other embodiments, the present invention also provides humanized antibodies or fragments thereof that differentially or preferentially bind to flaviviral antigens from one strain of the *flavivirus* versus another strain.

In one particular embodiment, the humanized antibodies of the invention are derived from a mouse monoclonal antibody produced by clones E16, E24, or E34. Hybridomas producing antibodies E16, E24, or E34 have been deposited with the American Type Culture Collection (10801 University Blvd., Manassas, Va. 20110-2209) on Jun. 4, 2004 under the provisions of the Budapest Treaty on the International Recognition of the Deposit of Microorganisms for the Purposes of Patent Procedures, and assigned accession numbers PTA-6050, PTA-6051, and PTA-6052, respectively, and are incorporated herein by reference. Representative plasmids encoding humanized antibodies of the invention, e.g., pMGX623-humanized E16 light chain version 1, the vector is pCINeo (Invitrogen), the insert consists of human germline sequence VKB2 and JK2 as framework, human kappa as constant region and mouse E16 CDRs; pMGX624—humanized E16 light chain version 2, same description as pMGX623 except a Y49S mutation in the variable region; pMGX625—humanized E16 heavy chain version 1, the vector is pCINeo (Invitrogen), the insert consists of human germline sequence VH1-18 and JH6 as framework, human IgG1 as constant region, and mouse E16 CDRs; pMGX626—humanized E16 heavy chain version 2, same description as pMGX625 except V67A, M69F, and T71A mutations in the variable region; and pMGX627—humanized E16 heavy chain version 3, same description as pMGX625 except a T71A mutation in the variable region; having ATCC Accession numbers PTA-6199, PTA-6200, PTA-6201, PTA-6202, and PTA-6203, respectively, were deposited under the provisions of the Budapest Treaty with the American Type Culture Collection (10801 University Blvd., Manassas, Va. 20110-2209) on Sep. 10, 2004, and are incorporated herein by reference.

In preferred embodiments, the invention encompasses humanized antibodies comprising the CDRs of E16, E24, or E34. In some embodiments, the present invention provides humanized antibodies or fragments thereof that immunospecifically bind to one or more WNV antigens, said antibodies or antibody fragments comprising a variable heavy ("VH") chain having an amino acid sequence of any one of the VH domains listed in SEQ ID NOS: 21, 22, or 23. The present invention also provides isolated humanized antibodies or fragments thereof that immunospecifically bind to one or more WNV antigens, said humanized antibodies or antibody fragments comprising a VL domain having an amino acid sequence of any one of the VL domains listed in SEQ ID NOS: 25 or 26.

In a specific embodiment, the invention encompasses a humanized antibody comprising the CDRs of E16, E24, or E34. The humanized WNV antibodies of the invention may have a heavy chain variable region comprising the amino acid sequence of CDR1 (SEQ ID NO: 1 or SEQ ID NO: 27) and/or CDR2 (SEQ ID NO: 2, SEQ ID NO: 28 or SEQ ID NO: 39) and/or CDR3 (SEQ ID NO: 3, SEQ ID NO: 29 or SEQ ID NO: 40) and/or a light chain variable region comprising the amino acid sequence of CDR1 (SEQ ID NO: 11) and/or a CDR2 (SEQ ID NO: 12) and/or CDR3 (SEQ ID NO: 13 or SEQ ID NO: 34). The sequences of the CDRs for E16, E24, and E34 heavy and light chain variable regions are provided in Table 1.

TABLE 1

| Segment | Kabat Number | E16 | SEQ ID NO. |
|---|---|---|---|
| VH FR1 | 1-30 | QVQLQQSGSELMKPGASVQISCKATGYTFS | 4 |
| CDR H1 | 31-35 | DYWIE | 1 |
| VH FR2 | 36-49 | WVKQRPGHGLEWIG | 5 |

TABLE 1-continued

| | Segment | | | SEQ ID NO. |
|---|---|---|---|---|
| | CDR H2 | 50-65 | DILCGTGRTRYNEKLKA | 2 |
| | VH FR3 | 66-94 | MATFTADTSSNTAFMQLSSLTSEDSAVYYCAR | 6 |
| | CDR H3 | 95-102 | SASYGDYADY | 3 |
| | VH FR4 | 103-113 | WGHGTTLTVSS | 10 |
| | VL FR1 | 1-23 | DIVMTQSHKFMSTSVGDRVSITC | 14 |
| | CDR L1 | 24-34 | KASQDVSTAVA | 11 |
| | VL FR2 | 35-49 | WYQQKPGQSPKLLIS | 15 |
| | CDR L2 | 50-56 | WASTRHT | 12 |
| | VL FR3 | 57-88 | GVPDRFTGSGSGTDYTLTISSVQAEDLALYYC | 18 |
| | CDR L3 | 89-97 | QQHYTTPLT | 13 |
| | VL FR4 | 98-107 | FGAGTKLELK | 19 |

| Segment | E24 | SEQ ID NO. | E34 | SEQ ID NO. |
|---|---|---|---|---|
| VH FR1 | QVQLQQSGPELVKPGALVKISCKASGHTFT | 30 | QVQLQQSGPELVKPGTLVKISCKTSGYTFT | 41 |
| CDR H1 | SYDIN | 27 | SYDIN | 27 |
| VH FR2 | WVKQRPGQGLEWIG | 31 | WVKQRPGQGLEWIG | 31 |
| CDR H2 | WIYPGDGRIKYNEKFKG | 28 | WIFPGDGRIKYNEQIKD | 39 |
| VH FR3 | KAILTADKSSSTAYMQLSSLTSENSAVYFCAR | 32 | KATLTADKSSSTAYMELSSLTSENSAVYFCAR | 42 |
| CDR H3 | GGSSGTYFDY | 29 | ASYYGSIFDY | 40 |
| VH FR4 | WGQGTTLTVSS | 33 | WGQGTTLTVSS | 33 |
| VL FR1 | DIVMTQSHKFMSTSVGDRVSITC | 14 | DIVMTQSHKFMSTSVGDRVNITC | 43 |
| CDR L1 | KASQDVSTAVA | 11 | KASQDVSTAVA | 11 |
| VL FR2 | WYQQKPGQSPKVLIY | 35 | WYQQKPGQSPKLLIY | 44 |
| CDR L2 | WASTRHT | 12 | WASTRHT | 12 |
| VL FR3 | GVPDRFTGSGSGTDYTLTISSVQAEDLALYYC | 18 | GVPDRFTGSGSGTHYTLTISSVQAEDLALYYC | 45 |
| CDR L3 | QQHYSNPPT | 34 | QQHYTTPLT | 13 |
| VL FR4 | FGGGTKLEIK | 36 | FGAGTKLELK | 19 |

TABLE 2

| Segment | Kabat Number | HuE16-1.1 | SEQ ID NO. |
|---|---|---|---|
| VH FR1 | 1-30 | QVQLVQSGAEVKKPGASVKVSCKASGYTFT | 48 |
| CDR H1 | 31-35 | DYWIE | 1 |
| VH FR2 | 36-49 | WVRQAPGQGLEWMG | 49 |
| CDR H2 | 50-65 | DILCGTGRTRYNEKLKA | 2 |
| VH FR3 | 66-94 | RVTMTTDTSTSTAYMELRSLRSDDTAVYYCAR | 7 |
| CDR H3 | 95-102 | SASYGDYADY | 3 |
| VH FR4 | 103-113 | WGQGTTVTVSS | 50 |
| VL FR1 | 1-23 | DIVMTQSPDSLAVSLGERATINC | 51 |

TABLE 2-continued

|  | Segment | | Kabat Number | | | | |
|---|---|---|---|---|---|---|---|
| | CDR L1 | 24-34 | KASQDVSTAVA | | | | 11 |
| | VL FR2 | 35-49 | WYQQKPGQPPKLLIY | | | | 16 |
| | CDR L2 | 50-56 | WASTRHT | | | | 12 |
| | VL FR3 | 57-88 | GVPDRFSGSGSGTDFTLTISSLQAEDVAVYYC | | | | 52 |
| | CDR L3 | 89-97 | QQHYTTPLT | | | | 13 |
| | VL FR4 | 98-107 | FGQGTKLEIK | | | | 53 |

| Segment | HuE16-1.2 | SEQ ID NO. | HuE16-2.1 | SEQ ID NO. |
|---|---|---|---|---|
| VH FR1 | QVQLVQSGAEVKKPGASVKVSCKASGYTFT | 48 | QVQLVQSGAEVKKPGAS-VKVSCKASGYTFT | 48 |
| CDR H1 | DYWIE | 1 | DYWIE | 1 |
| VH FR2 | WVRQAPGQGLEWMG | 49 | WVRQAPGQGLEWMG | 49 |
| CDR H2 | DILCGTGRTRYNEKLKA | 2 | DILCGTGRTRYNEKLKA | 2 |
| VH FR3 | RVTMTTDTSTSTAYMELRSLRSDDTAVYYCAR | 7 | RATFTADTSTSTAYMEL-RSLRSDDTAVYYCAR | 8 |
| CDR H3 | SASYGDYADY | 3 | SASYGDYADY | 3 |
| VH FR4 | WGQGTTVTVSS | 50 | WGQGTTVTVSS | 50 |
| VL FR1 | DIVMTQSPDSLAVSLGERATINC | 51 | DIVMTQSPDSLAVSLGER-ATINC | 51 |
| CDR L1 | KASQDVSTAVA | 11 | KASQDVSTAVA | 11 |
| VL FR2 | WYQQKPGQPPKLLIS | 17 | WYQQKPGQPPKLLIY | 16 |
| CDR L2 | WASTRHT | 12 | WASTRHT | 12 |
| VL FR3 | GVPDRFSGSGSGTDFTLTISSLQAEDVAVYYC | 52 | GVPDRFSGSGSGTD-FTLTISSLQAEDVAVYYC | 52 |
| CDR L3 | QQHYTTPLT | 13 | QQHYTTPLT | 13 |
| VL FR4 | FGQGTKLEIK | 53 | FGQGTKLEIK | 53 |

| Segment | Kabat Number | HuE16-2.2 | SEQ ID NO. |
|---|---|---|---|
| VH FR1 | 1-30 | QVQLVQSGAEVKKPGASVKVSCKASGYTFT | 48 |
| CDR H1 | 31-35 | DYWIE | 1 |
| VH FR2 | 36-49 | WVRQAPGQGLEWMG | 49 |
| CDR H2 | 50-65 | DILCGTGRTRYNEKLKA | 2 |
| VH FR3 | 66-94 | RATFTADTSTSTAYMELRSLRSDDTAVYYCAR | 8 |
| CDR H3 | 95-102 | SASYGDYADY | 3 |
| VH FR4 | 103-113 | WGQGTTVTVSS | 50 |
| VL FR1 | 1-23 | DIVMTQSPDSLAVSLGERATINC | 51 |
| CDR L1 | 24-34 | KASQDVSTAVA | 11 |
| VL FR2 | 35-49 | WYQQKPGQPPKLLIS | 17 |
| CDR L2 | 50-56 | WASTRHT | 12 |
| VL FR3 | 57-88 | GVPDRFSGSGSGTDFTLTISSLQAEDVAVYYC | 52 |

TABLE 2-continued

| Segment | HuE16-3.1 | SEQ ID NO. | HuE16-3.2 | SEQ ID NO. |
|---|---|---|---|---|
| | CDR L3 89-97 QQHYTTPLT | | | 13 |
| | VL FR4 98-107 FGQGTKLEIK | | | 53 |
| VH FR1 | QVQLVQSGAEVKKPGASVKVSCKASGYTFT | 48 | QVQLVQSGAEVKKPGAS-VKVSCKASGYTFT | 48 |
| CDR H1 | DYWIE | 1 | DYWIE | 1 |
| VH FR2 | WVRQAPGQGLEWMG | 49 | WVRQAPGQGLEWMG | 49 |
| CDR H2 | DILCGTGRTRYNEKLKA | 2 | DILCGTGRTRYNEKLKA | 2 |
| VH FR3 | RVTMTADTSTSTAYMELRSLRSDDTAVYYCAR | 9 | RVTMTADTSTSTAYMEL-RSLRSDDTAVYYCAR | 9 |
| CDR H3 | SASYGDYADY | 3 | SASYGDYADY | 3 |
| VH FR4 | WGQGTTVTVSS | 50 | WGQGTTVTVSS | 50 |
| VL FR1 | DIVMTQSPDSLAVSLGERATINC | 51 | DIVMTQSPDSLAVSLGER-ATINC | 51 |
| CDR L1 | KASQDVSTAVA | 11 | KASQDVSTAVA | 11 |
| VL FR2 | WYQQKPGQPPKLLIY | 16 | WYQQKPGQPPKLLIS | 17 |
| CDR L2 | WASTRHT | 12 | WASTRHT | 12 |
| VL FR3 | GVPDRFSGSGSGTDFTLTISSLQAEDVAVYYC | 52 | GVPDRFSGSGSGTD-FTLTISSLQAEDVAVYYC | 52 |
| CDR L3 | QQHYTTPLT | 13 | QQHYTTPLT | 13 |
| VL FR4 | FGQGTKLEIK | 53 | FGQGTKLEIK | 53 |

In one specific embodiment, the invention provides a humanized E16, E24, or E34 antibody, wherein the VH region consists of the FR segments from the human germline VH segment VH1-18 (Matsuda et al., 1998, J. Exp. Med. 188: 2151062) and JH6 (Ravetch et al., 1981, Cell 27(3 Pt. 2): 583-91), and one or more CDR regions of a E16, E24, or E34-VH, having the amino acid sequence of SEQ ID NO: 1, SEQ ID NO: 2, SEQ ID NO: 3, SEQ ID NO: 27, SEQ ID NO: 28, SEQ ID NO: 29, SEQ ID NO: 39, or SEQ ID NO: 40. In one embodiment, the E16 VH has the amino acid sequence of SEQ ID NO: 21, SEQ ID NO: 22, or SEQ ID NO: 23. In another specific embodiment, the humanized E16 antibody further comprises a VL region, which consists of the FR segments of the human germline VL segment VK-B3, and one or more CDR regions of E16, E24, or E34 VL, having the amino acid sequence of SEQ ID NO: 11, SEQ ID NO: 12, SEQ ID NO: 13, or SEQ ID NO: 34. In one embodiment, the E16 VL has the amino acid sequence of SEQ ID NO: 25 or SEQ ID NO: 26. In another embodiment, the heavy chain FR3 may consist of the amino acid sequence of SEQ ID NO: 7, SEQ ID NO: 8, or SEQ ID NO: 9. In another embodiment, the light chain FR2 may consist of the amino acid sequence of SEQ ID NO: 16 or SEQ ID NO: 17. Humanized E16 antibodies comprising a VH FR3 sequence of SEQ ID NO: 7, SEQ ID NO: 8, or SEQ ID NO: 9 and a VH FR2 sequence of SEQ ID NO: 16 or SEQ ID NO: 17 are provided in Table 2 as HuE16-1.1, HuE16-1.2, HuE16-2.1, HuE16-2.2, HuE16-3.1, and HuE16-3.2.

In preferred embodiments, the humanized antibodies of the invention comprise the FR regions of the human germline VH segment VH1-18 and JH6 and the FR regions of the human germline VL segment VK-B3, but have one or more of the following back mutations: V67A, M69F, T71A in the heavy chain and Y49S in the light chain.

In particular, the invention provides a humanized antibody a WNV virus antigen, said antibody comprising (or alternatively, consisting of) CDR sequences of E16, E24, or E34, in any of the following combinations: a VH CDR1 and a VL CDR1; a VH CDR1 and a VL CDR2; a VH CDR1 and a VL CDR3; a VH CDR2 and a VL CDR1; VH CDR2 and VL CDR2; a VH CDR2 and a VL CDR3; a VH CDR3 and a VH CDR1; a VH CDR3 and a VL CDR2; a VH CDR3 and a VL CDR3; a VH1 CDR1, a VH CDR2 and a VL CDR1; a VH CDR1, a VH CDR2 and a VL CDR2; a VH CDR1, a VH CDR2 and a VL CDR3; a VH CDR2, a VH CDR3 and a VL CDR1, a VH CDR2, a VH CDR3 and a VL CDR2; a VH CDR2, a VH CDR2 and a VL CDR3; a VH CDR1, a VL CDR1 and a VL CDR2; a VH CDR1, a VL CDR1 and a VL CDR3; a VH CDR2, a VL CDR1 and a VL CDR2; a VH CDR2, a VL CDR1 and a VL CDR3; a VH CDR3, a VL CDR1 and a VL CDR2; a VH CDR3, a VL CDR1 and a VL CDR3; a VH CDR1, a VH CDR2, a VH CDR3 and a VL CDR1; a VH CDR1, a VH CDR2, a VH CDR3 and a VL CDR2; a VH CDR1, a VH CDR2, a VH CDR3 and a VL CDR3; a VH CDR1, a VH CDR2, a VL CDR1 and a VL CDR2; a VH CDR1, a VH CDR2, a VL CDR1 and a VL CDR3; a VH CDR1, a VH CDR3, a VL CDR1 and a VL CDR2; a VH CDR1, a VH CDR3, a VL CDR1 and a VL CDR3; a VH CDR2, a VH CDR3, a VL CDR1 and a VL CDR2; a VH CDR2, a VH CDR3, a VL CDR1 and a VL CDR3; a VH CDR2, a VH CDR3, a VL CDR2 and a VL CDR3; a VH CDR1, a VH CDR2, a VH CDR3, a VL CDR1 and a VL CDR2; a VH CDR1, a VH CDR2, a VH CDR3, a VL CDR1 and a VL CDR3; a VH CDR1, a VH CDR2, a VL CDR1, a VL CDR2, and a VL CDR3; a VH CDR1, a VH CDR3, a VL CDR1, a VL CDR2, and a VL CDR3; a VH CDR2, a VH CDR3, a VL CDR1, a VL CDR2, and a VL CDR3; or any combination thereof of the VH CDRs and VL CDRs disclosed herein.

The present invention provides humanized antibody molecules specific for WNV in which one or more regions of one or more CDRs of the heavy and/or light chain variable regions of a human antibody (the recipient antibody) have been substituted by analogous parts of one or more CDRs of a donor monoclonal antibody which specifically binds a WNV antigen, e.g., a monoclonal antibody produced by clone E16, E24, or E34. In other embodiments, the humanized antibodies of the invention bind to the same epitope as E16, E24, or E34. In a most preferred embodiment, the humanized antibody specifically binds to the same epitope as the donor murine antibody. It will be appreciated by one skilled in the art that the invention encompasses CDR grafting of antibodies in general. Thus, the donor and acceptor antibodies may be derived from animals of the same species and even same antibody class or sub-class. More usually, however, the donor and acceptor antibodies are derived from animals of different species. Typically the donor antibody is a non-human antibody, such as a rodent MAb, and the acceptor antibody is a human antibody.

In some embodiments, at least one CDR from the donor antibody is grafted onto the human antibody. In other embodiments, at least two and preferably all three CDRs of each of the heavy and/or light chain variable regions are grafted onto the human antibody. The CDRs may comprise the Kabat CDRs, the structural loop CDRs or a combination thereof. In some embodiments, the invention encompasses a humanized WNV antibody comprising at least one CDR grafted heavy chain and at least one CDR-grafted light chain.

In a preferred embodiment, the CDR regions of the humanized WNV specific antibody are derived from a murine antibody specific for WNV. In some embodiments, the humanized antibodies described herein comprise alterations, including, but not limited to, amino acid deletions, insertions, modifications, of the acceptor antibody, i.e., human, heavy and/or light chain variable domain framework regions that are necessary for retaining binding specificity of the donor monoclonal antibody. In some embodiments, the framework regions of the humanized antibodies described herein does not necessarily consist of the precise amino acid sequence of the framework region of a natural occurring human antibody variable region, but contains various alterations, including, but not limited to, amino acid deletions, insertions, modifications that alter the property of the humanized antibody, for example, improve the binding properties of a humanized antibody region that is specific for the same target as the murine WNV specific antibody. In most preferred embodiments, a minimal number of alterations are made to the framework region in order to avoid large-scale introductions of non-human framework residues and to ensure minimal immunogenicity of the humanized antibody in humans. The donor monoclonal antibody is preferably a monoclonal antibody produced by clones E16, E24, or E34 which bind the WNV E antigen.

In specific embodiments of the invention, the humanized antibodies of the invention comprise one or more of the substitutions in the VH region as depicted in Table 3 and/or one or more of the substitutions in the VL region as depicted in Table 4 (substitutions are from mouse to human).

TABLE 3

| Position | Framework region | Mouse Amino Acid | Human Amino Acid |
|---|---|---|---|
| 5 | FR1 | Q | V |
| 6 | FR1 | Q | E |
| 9 | FR1 | S | A |
| 11 | FR1 | L | V |
| 12 | FR1 | M | K |
| 19 | FR1 | Q | K |
| 20 | FR1 | I | V |
| 25 | FR1 | T | S |
| 30 | FR1 | S | T |
| 38 | FR2 | K | R |
| 40 | FR2 | R | A |
| 43 | FR2 | H | Q |
| 48 | FR2 | I | M |
| 66 | FR3 | M | R |
| 67 | FR3 | A | V |
| 69 | FR3 | F | M |
| 71 | FR3 | A | T |
| 75 | FR3 | S | T |
| 76 | FR3 | N | S |
| 79 | FR3 | F | Y |
| 81 | FR3 | Q | E |
| 82A | FR3 | S | R |
| 83 | FR3 | T | R |
| 85 | FR3 | E | D |
| 87 | FR3 | S | T |
| 105 | FR4 | H | Q |
| 109 | FR4 | L | V |

TABLE 4

| Position | Framework region | Mouse Amino Acid | Human Amino Acid |
|---|---|---|---|
| 8 | FR1 | H | P |
| 9 | FR1 | K | D |
| 10 | FR1 | F | S |
| 11 | FR1 | M | L |
| 12 | FR1 | S | A |
| 13 | FR1 | T | V |
| 15 | FR1 | V | L |
| 17 | FR1 | D | E |
| 19 | FR1 | V | A |
| 20 | FR1 | S | T |
| 22 | FR1 | T | N |
| 43 | FR2 | S | P |
| 49 | FR2 | S | Y |
| 63 | FR3 | T | S |
| 71 | FR3 | Y | F |
| 78 | FR3 | V | L |
| 83 | FR3 | L | V |
| 85 | FR3 | L | V |
| 100 | FR4 | A | Q |

In a specific embodiment, the invention encompasses a CDR-grafted antibody which specifically binds a WNV antigen, wherein the CDR-grafted antibody comprises a heavy chain variable region domain comprising framework residues of the recipient antibody and residues from the donor monoclonal antibody, which specifically binds WNV, e.g., monoclonal antibody produced from clones E16, E24, or E34. In another specific embodiment, the invention encompasses a CDR-grafted antibody which specifically binds a WNV antigen, wherein the CDR-grafted antibody comprises a light chain variable region domain comprising framework residues of the recipient antibody and residues from the donor monoclonal antibody, which specifically binds a WNV antigen, e.g., a monoclonal antibody produced from one of clones E16, E24, or E34.

Humanized WNV specific antibodies of the invention may comprise substantially all of at least one, and typically two, variable domains in which all or substantially all of the CDR regions correspond to those of a non-human immunoglobulin (i.e., donor antibody) and all or substantially all of the framework regions are those of a human immunoglobulin consensus sequence. Preferably, a humanized antibody of the invention also comprises at least a portion of an immunoglobulin constant region (Fc), typically that of a human immunoglobulin. The constant domains of the humanized antibodies of the invention may be selected with respect to the proposed function of the antibody, in particular the effector function which may be required. In some embodiments, the constant domains of the humanized antibodies of the invention are human IgA, IgE, IgG or IgM domains. In a specific embodiment, human IgG constant domains, especially of the IgG1 and IgG3 isotypes, are used when the humanized antibodies of the invention are intended for therapeutic uses and antibody effector functions are needed. In alternative embodiments, IgG2 and IgG4 isotypes are used when the humanized antibodies of the invention are intended for therapeutic purposes and antibdy effector function is not required. The invention encompasses Fc constant domains comprising one or more amino acid modifications which alter antibody effector functions such as those disclosed in U.S. application Ser. No. 10/754,922, filed Jan. 9, 2004; U.S. Provisional Application Nos. 60/439,498; 60/456,041; 60/514,549; 60/569,882, 60/582,045; and 60/582,043 filed on Jan. 9, 2003; Mar. 19, 2003; Oct. 23, 2003; May 10, 2004; Jun. 21, 2004; and Jun. 21, 2004, respectively; all of which are incorporated herein by reference in their entireties.

In some embodiments, humanized antibodies of the invention contain both the light chain as well as at least the variable domain of a heavy chain. In other embodiments, humanized antibodies of the invention may further comprise one or more of the CH1, hinge, CH2, CH3, and CH4 regions of the heavy chain. The humanized antibody can be selected from any class of immunoglobulins, including IgM, IgG, IgD, IgA and IgE, and any isotype, including $IgG_1$, $IgG_2$, $IgG_3$ and $IgG_4$. In some embodiments, the constant domain is a complement fixing constant domain where it is desired that the humanized antibody exhibit cytotoxic activity, and the class is typically $IgG_1$. In other embodiments, where such cytotoxic activity is not desirable, the constant domain may be of the $IgG_2$ class. Humanized antibodies of the invention may comprise sequences from more than one class or isotype, and selecting particular constant domains to optimize desired effector functions is within the ordinary skill in the art.

The framework and CDR regions of a humanized antibody need not correspond precisely to the parental sequences, e.g., the donor CDR or the consensus framework may be mutagenized by substitution, insertion or deletion of at least one residue so that the CDR or framework residue at that site does not correspond to either the consensus or the donor antibody. Such mutations, however, are preferably not extensive. Usually, at least 75% of the humanized antibody residues will correspond to those of the parental framework region (FR) and CDR sequences, more often 90%, and most preferably greater than 95%.

The humanized antibodies used in the methods of the invention include derivatives that are modified, i.e, by the covalent attachment of any type of molecule to the antibody such that covalent attachment. For example, but not by way of limitation, the antibody derivatives include antibodies that have been modified, e.g., by glycosylation, acetylation, pegylation, phosphorylation, amidation, derivatization by known protecting/blocking groups, proteolytic cleavage, linkage to a cellular ligand or other protein, etc. Antibody derivatives may also include aglycosylated forms. Any of numerous chemical modifications may be carried out by known techniques, including, but not limited to, specific chemical cleavage, acetylation, formylation, metabolic synthesis of tunicamycin, etc. Additionally, the derivative may contain one or more non-classical amino acids.

Further, the humanized antibodies of the invention can, in turn, be utilized to generate anti-idiotype antibodies using techniques well known to those skilled in the art. (See, e.g., Greenspan & Bona, 1989, *FASEB J.* 7:437-444; and Nissinoff, 1991, *J. Immunol.* 147:2429-2438).

The present invention encompasses single domain antibodies, including camelized single domain antibodies (See e.g., Muyldermans et al., 2001, *Trends Biochem. Sci.* 26:230; Nuttall et al., 2000, *Cur. Pharm. Biotech.* 1:253; Reichmann and Muyldermans, 1999, *J. Immunol. Meth.* 231:25; International Publication Nos. WO 94/04678 and WO 94/25591; U.S. Pat. No. 6,005,079; which are incorporated herein by reference in their entireties). In one embodiment, the present invention provides single domain antibodies comprising two VH domains with modifications such that single domain antibodies are formed.

The methods of the present invention also encompass the use of humanized antibodies or fragments thereof that have half-lives (e.g., serum half-lives) in a mammal, preferably a human, of greater than 15 days, preferably greater than 20 days, greater than 25 days, greater than 30 days, greater than 35 days, greater than 40 days, greater than 45 days, greater than 2 months, greater than 3 months, greater than 4 months, or greater than 5 months. The increased half-lives of the humanized antibodies of the present invention or fragments thereof in a mammal, preferably a human, results in a higher serum titer of said humanized antibodies or antibody fragments in the mammal, and thus, reduces the frequency of the administration of said humanized antibodies or antibody fragments and/or reduces the concentration of said humanized antibodies or antibody fragments to be administered. Humanized antibodies or fragments thereof having increased in vivo half-lives can be generated by techniques known to those of skill in the art. For example, humanized antibodies or fragments thereof with increased in vivo half-lives can be generated by modifying (e.g., substituting, deleting or adding) amino acid residues identified as involved in the interaction between the Fc domain and the FcRn receptor. The humanized antibodies of the invention may be engineered by methods described in Ward et al. to increase biological half-lives (See U.S. Pat. No. 6,277,375 B1). For example, humanized antibodies of the invention may be engineered in the Fc-hinge domain to have increased in vivo or serum half-lives.

Humanized antibodies or fragments thereof with increased in vivo half-lives can be generated by attaching to said humanized antibodies or antibody fragments polymer molecules such as high molecular weight polyethyleneglycol (PEG). PEG can be attached to said humanized antibodies or antibody fragments with or without a multifunctional linker either through site-specific conjugation of the PEG to the N- or C-terminus of said humanized antibodies or antibody fragments or via epsilon-amino groups present on lysine residues. Linear or branched polymer derivatization that results in minimal loss of biological activity will be used. The degree of conjugation will be closely monitored by SDS-PAGE and mass spectrometry to ensure proper conjugation of PEG molecules to the humanized antibodies. Unreacted PEG can be separated from antibody-PEG conjugates by, e.g., size exclusion or ion-exchange chromatography.

The humanized antibodies of the invention may also be modified by the methods and coupling agents described by Davis et al. (See U.S. Pat. No. 4,179,337) in order to provide compositions that can be injected into the mammalian circulatory system with substantially no immunogenic response.

The invention also provides humanized antibodies with altered oligosaccharide content. Oligosaccharides, as used herein, refer to carbohydrates containing two or more simple sugars and the two terms may be used interchangeably herein. Carbohydrate moieties of the instant invention will be described with reference to commonly used nomenclature in the art. For a review of carbohydrate chemistry, see, e.g., Hubbard et al., 1981 Ann. Rev. Biochem., 50: 555-583, which is incorporated herein by reference in its entirety. This nomenclature includes, for example, Man which represents mannose; GlcNAc which represents 2-N-acetylglucosamine; Gal which represents galactose; Fuc for fucose and Glc for glucose. Sialic acids are described by the shorthand notation NeuNAc for 5-N-acetylneuraminic acid, and NeuNGc for 5-glycolneuraminic.

In general, antibodies contain carbohydrate moeities at conserved positions in the constant region of the heavy chain, and up to 30% of human IgGs have a glycosylated Fab region. IgG has a single N-linked biantennary carbohydrate structure at Asn 297 which resides in the CH2 domain (Jefferis et al., 1998, Immunol. Rev. 163: 59-76; Wright et al., 1997, Trends Biotech 15: 26-32). Human IgG typically has a carbohydrate of the following structure; GlcNAc(Fucose)-GlcNAc-Man-(ManGlcNAc)$_2$. However variations among IgGs in carbohydrate content does occur which leads to altered function, see, e.g., Jassal et al., 2001, Biochem. Biophys. Res. Commun. 288: 243-9; Groenink et al., 1996, J. Immunol. 26: 1404-7; Boyd et al., 1995, Mol. Immunol. 32: 1311-8; Kumpel et al., 1994, Human Antibody Hybridomas, 5:143-51. In one embodiment, the carbohydrate moiety has a galactose and/or galactose-sialic acid at one or both of the terminal GlcNAc and/or a third GlcNac arm (bisecting GlcNAc).

In some embodiments, the humanized antibodies of the invention are substantially free of one or more selected sugar groups, e.g., one or more sialic acid residues, one or more galactose residues, one or more fucose residues. A humanized antibody that is substantially free of one or more selected sugar groups may be prepared using common methods known to one skilled in the art, including, for example, recombinantly producing an humanized antibody of the invention in a host cell that is defective in the addition of the selected sugar groups(s) to the carbohydrate moiety of the antibody, such that about 90-100% of the humanized antibody in the composition lacks the selected sugar group(s) attached to the carbohydrate moiety. Alternative methods for preparing such antibodies include, for example, culturing cells under conditions which prevent or reduce the addition of one or more selected sugar groups, or post-translational removal of one or more selected sugar groups.

In a specific embodiment, the invention encompasses a method of producing a substantially homogenous humanized antibody preparation, wherein about 80-100% of the humanized antibody in the composition lacks a fucose on its carbohydrate moiety. The antibody may be prepared, for example, by (a) use of an engineered host cell that is deficient in fucose metabolism such that it has a reduced ability to fucosylate proteins expressed therein; (b) culturing cells under conditions which prevent or reduce fusocylation; (c) post-translational removal of fucose, e.g., with a fucosidase enzyme; or (d) purification of the antibody so as to select for the product which is not fucosylated. Most preferably, a nucleic acid encoding the desired antibody is expressed in a host cell that has a reduced ability to fucosylate the antibody expressed therein. Preferably, the host cell is a Lec 13 CHO cell (lectin resistant CHO mutant cell line; U.S. Patent Application Publication No. 2003/0115614; PCT Publication No. WO 00/61739; European Patent Application EP 1 229 125; Ribka & Stanley, 1986, Somatic Cell & Molec. Gen. 12(1): 51-62; Ripka et al., 1986 Arch. Biochem. Biophys. 249(2): 533-45), CHO-K1 cell, DUX-B11 cell, CHO-DP12 cell or CHO-DG44 cell, which has been modified so that the antibody is not substantially fucosylated. Thus, the cell may display altered expression and/or activity for the fucoysltransferase enzyme, or another enzyme or substrate involved in adding fucose to the N-linked oligosaccharide so that the enzyme has a diminished activity and/or reduced expression level in the cell. For methods to produce antibodies with altered fucose content, see, e.g., WO 03/035835 and Shields et al., 2002, J. Biol. Chem. 277(30): 26733-40; both of which are incorporated herein by reference in their entirety.

In some embodiments, the altered carbohydrate modifications modulate one or more of the following: solubilization of the antibody, facilitation of subcellular transport and secretion of the antibody, promotion of antibody assembly, conformational integrity, and antibody-mediated effector function. In a specific embodiment the altered carbohydrate modifications enhance antibody mediated effector function relative to the antibody lacking the carbohydrate modification. Carbohydrate modifications that lead to altered antibody mediated effector function are well known in the art (for example, see Shields R. L. et al., 2001, J. Biol. Chem. 277 (30): 26733-40; Davies J. et al., 2001, Biotechnology & Bioengineering, 74: 288-294). In another specific embodiment, the altered carbohydrate modifications enhance the binding of humanized antibodies of the invention to a flaviviral antigen. Altering carbohydrate modifications in accordance with the methods of the invention includes, for example, increasing the carbohydrate content of the antibody or decreasing the carbohydrate content of the antibody. Methods of altering carbohydrate contents are known to those skilled in the art, see, e.g., Wallick et al., 1988, J Exp. Med. 168(3): 1099-1109; Tao et al., 1989, Journal of Immunology, 143(8): 2595-2601; Routledge et al., 1995, Transplantation, 60(8): 847-53; Elliott et al., 2003, Nature Biotechnology 21:414-21; Shields et al., 2002, J Biol Chem, 277(30): 26733-40; all of which are incorporated herein by reference in their entirety.

In some embodiments, the invention encompasses humanized antibodies comprising one or more glycosylation sites, so that one or more carbohydrate moieties are covalently attached to the antibody. In other embodiments, the invention encompasses humanized antibodies comprising one or more glycosylation sites. In some embodiments, the invention further comprises humanized antibodies comprising one or more modifications of amino acids that are directly or indirectly known to interact with a carbohydrate moiety of the antibody. Amino acids that directly or indirectly interact with a carbohydrate moiety of an antibody are known in the art, see, e.g., Jefferis et al., 1995, Immunology Letters 44: 111-7, which is incorporated herein by reference in its entirety.

The invention encompasses humanized antibodies that have been modified by introducing one or more glycosylation sites into one or more sites of the antibodies, preferably without altering the functionality of the antibody. Glycosylation sites may be introduced into the variable and/or constant region of the humanized antibodies of the invention. As used herein, "glycosylation sites" include any specific amino acid sequence in an antibody to which an oligosaccharide (i.e., carbohydrates containing two or more simple sugars linked together) will specifically and covalently attach. Oligosaccharide side chains are typically linked to the backbone of an antibody via either N- or O-linkages. N-linked glycosylation refers to the attachment of an oligosaccharide moiety to the side chain of an asparagine residue. O-linked glycosylation refers to the attachment of an oligosaccharide moiety to a hydroxyamino acid, e.g., serine, threonine. The humanized antibodies of the invention may comprise one or more glycosylation sites, including N-linked and O-linked glycosylation sites. Any glycosylation site for N-linked or O-linked glycosylation known in the art may be used in accordance with the instant invention. An exemplary N-linked glycosylation site that is useful in accordance with the methods of the present invention, is the amino acid sequence: Asn-X-Thr/Ser, wherein X may be any amino acid and Thr/Ser indicates a threonine or a serine. Such a site or sites may be introduced into humanized antibodies of the invention using methods well known in the art to which this invention pertains. See, for example, "In vitro Mutagenesis," Recombinant DNA: A Short Course, J. D. Watson, et al. W.H. Freeman and Company, New York, 1983, chapter 8, pp. 106-116, which is incorporated herein by reference in its entirety. An exemplary method for introducing a glycosylation site into humanized antibodies of the invention may comprise: modifying or mutating an amino acid sequence of the antibody so that the desired Asn-X-Thr/Ser sequence is obtained.

In some embodiments, the invention encompasses methods of modifying the carbohydrate content of humanized antibodies of the invention by adding or deleting a glycosylation site. Methods for modifying the carbohydrate content of antibodies are well known in the art and encompassed within the invention, see, e.g., U.S. Pat. No. 6,218,149; EP 0 359 096 B1; U.S. Patent Application Publication No. U.S. 2002/0028486; WO 03/035835; U.S. Publication No. 2003/0115614; U.S. Pat. No. 6,218,149; U.S. Pat. No. 6,472,511; all of which are incorporated herein by reference in their entirety. In other embodiments, the invention encompasses methods of modifying the carbohydrate content of humanized antibodies of the invention by deleting one or more endogenous carbohydrate moieties of the antibody.

The invention further encompasses methods of modifying an effector function of humanized antibodies of the invention, wherein the method comprises modifying the carbohydrate content of the antibody using the methods disclosed herein or known in the art.

Standard techniques known to those skilled in the art can be used to introduce mutations in the nucleotide sequence encoding an antibody, or fragment thereof, including, e.g., site-directed mutagenesis and PCR-mediated mutagenesis, which results in amino acid substitutions. Preferably, the derivatives include less than 15 amino acid substitutions, less than 10 amino acid substitutions, less than 5 amino acid substitutions, less than 4 amino acid substitutions, less than 3 amino acid substitutions, or less than 2 amino acid substitutions relative to the original antibody or fragment thereof. In a preferred embodiment, the derivatives have conservative amino acid substitutions made at one or more predicted non-essential amino acid residues.

The present invention also encompasses humanized antibodies or fragments thereof comprising an amino acid sequence of a variable heavy chain and/or variable light chain that is at least 45%, at least 50%, at least 55%, at least 60%, at least 65%, at least 70%, at least 75%, at least 80%, at least 85%, at least 90%, at least 95%, or at least 99% identical to the amino acid sequence of the variable heavy chain and/or light chain of the mouse monoclonal antibody produced by clone E16, E24, or E34. The present invention further encompasses humanized antibodies or fragments thereof that specifically bind WNV, said humanized antibodies or antibody fragments comprising an amino acid sequence of one or more CDRs that is at least 45%, at least 50%, at least 55%, at least 60%, at least 65%, at least 70%, at least 75%, at least 80%, at least 85%, at least 90%, at least 95%, or at least 99% identical to the amino acid sequence of one or more CDRs of the mouse monoclonal antibody produced by clone E16, E24, or E34. The determination of percent identity of two amino acid sequences can be determined by any method known to one skilled in the art, including BLAST protein searches.

The present invention also encompasses the use of humanized antibodies or antibody fragments that specifically bind WNV, wherein said humanized antibodies or antibody fragments are encoded by a nucleotide sequence that hybridizes to the nucleotide sequence of the mouse monoclonal antibody produced by clone E16, E24, or E34, under stringent conditions. In a preferred embodiment, the invention provides humanized antibodies or fragments thereof that specifically bind WNV, said humanized antibodies or antibody fragments comprising a variable light chain and/or variable heavy chain encoded by a nucleotide sequence that hybridizes under stringent conditions to the nucleotide sequence of the variable light chain and/or variable heavy chain of the mouse monoclonal antibody produced by clone E16, E24, or E34, under stringent conditions. In another preferred embodiment, the invention provides humanized antibodies or fragments thereof that specifically bind WNV, said humanized antibodies or antibody fragments comprising one or more CDRs encoded by a nucleotide sequence that hybridizes under stringent conditions to the nucleotide sequence of one or more CDRs of the mouse monoclonal antibody produced by clone E16, E24, or E34. Stringent hybridization conditions include, but are not limited to, hybridization to filter-bound DNA in 6× sodium chloride/sodium citrate (SSC) at about 45° C. followed by one or more washes in 0.2×SSC/0.1% SDS at about 50-65° C., highly stringent conditions such as hybridization to filter-bound DNA in 6×SSC at about 45° C. followed by one or more washes in 0.1×SSC/0.2% SDS at about 60° C., or any other stringent hybridization conditions known to those skilled in the art (see, for example, Ausubel, F. M. et al., eds. 1989 Current Protocols in Molecular Biology, vol. 1, Green Publishing Associates, Inc. and John Wiley and Sons, Inc., NY at pages 6.3.1 to 6.3.6 and 2.10.3, incorporated herein by reference).

The antibody or antibody fragment generated by introducing substitutions in the VH domain, VH CDRs, VL domain and/or VL CDRs of the humanized antibodies of the invention can be tested in vitro and in vivo, for example, for its ability to bind to flaviviral antigens, particularly WNV antigens, for its ability to neutralize a *flavivirus*, particularly WNV, or for its ability to prevent, treat or ameliorate one or more symptoms associated with a *flavivirus*, particularly WNV infection.

In most preferred embodiments, the invention encompasses humanized antibodies or fragments thereof that have potent neutralizing activity as measured for example using standard methods known in the art and exemplified herein, e.g., in vivo plaque reduction neutralization titer (PRNT) assay. Although not intending to be bound by a particular mechanims of action the humanized antibodies of the invention may directly neutralize virus or block entry of the virus into the cell, thus preventing viral infections. In some embodiments, the invention encompasses humanized antibodies which immunospecifically bind WNV-E protein such that the $PRNT_{50}$ values are at least 1/500, preferably at least 1/10,000 at a concentration of 1 mg/mL.

In yet other preferred embodiments, humanized antibodies of the invention have enhanced antibody-dependent complement mediated neutralization of WNV infected virions and trigger lysis of WNV-infected cells more effectively, as determined using standard methods known in the art and exemplified herein such as complement fixation and viability assays Although not intending to be bound by a particular mechanism of action, the humanized antibodies of the invention have enhanced clinical efficacy, therapeutically and prophylactically as they have enhanced effector functions, neutralize virus attachment, trigger complement mediated lysis, promote clearance from the circulatory systems and prevent emergence of viral resistance. The humanized antibodies of the invention preferably have a potent in vivo inhibitory activity, i.e., protect against WNV infection by at least 50%, at least 60%, at least 70%, at least 80%, at least 90%, at least 99%.

The present invention provides humanized antibodies or fragments thereof which immunospecifically bind to one or more flaviviral antigens particularly WNV antigens and have an apparent dissociation constant of about 1-10 nM, as determined by a sandwich ELISA. The present invention provides humanized antibodies or fragments thereof which immuospecifically bind to one or more flaviviral antigens, particularly WNV antigens, and have an apparent dissociation constant of about 1-10 nM as measured by surface plasmon resonance (SPR) using a BIAcore sensor.

The present invention provides humanized antibodies or fragments thereof which immunospecifically bind to one or more flaviviral antigens, particularly WNV antigens, and have a $k_{off}$ rate (antibody (Ab)+antigen (Ag)$^{K_{off}}$→Ab-Ag of less than $10^{-1}$ s$^{-1}$, less than $5\times10^{-1}$ s$^{-1}$, less than $10^{-2}$ s$^{-1}$, less than $5\times10^{-2}$ s$^{-1}$, less than $10^{-3}$ s$^{-1}$, less than $5\times10^{-3}$ s$^{-1}$, less than $10^{-4}$ s$^{-1}$, less than $5\times10^{-4}$ s$^{-1}$, less than $10^{-5}$ s$^{-1}$, less than $5\times10^{-5}$ s$^{-1}$, less than $10^{-6}$ s$^{-1}$, less than $5\times10^{-6}$ s$^{-1}$, less than $10^{-7}$ s$^{-1}$, less than $5\times10^{-7}$ s$^{-1}$, less than $10^{-8}$ s$^{-1}$, less than $5\times10^{-8}$ s$^{-1}$, less than $10^{-9}$ s$^{-1}$, less than $5\times10^{-9}$ s$^{-1}$, or less than $10^{-1}$ s$^{-1}$. The present invention provides humanized antibodies or fragments thereof which immunospecifically bind to one or more flaviviral antigens, particularly WNV antigens, and have a $k_{off}$ rate (antibody (Ab)+antigen (Ag)$^{K_{off}}$→Ab-Ag of about $1\times10^{-3}$, about $5\times10^{-4}$, about $1\times10^{-4}$, about $5\times10^{-5}$, about $1\times10^{-5}$, about $5\times10^{-6}$, or about $1\times10^{-6}$. The present invention provides humanized antibodies or fragments thereof which immunospecifically bind to one or more flaviviral antigens, particularly WNV antigens, and have a $k_{on}$ rate of about $1\times10^{4}$, about $5\times10^{4}$, about $1\times10^{5}$, about $5\times10^{5}$, about $1\times10^{6}$, or about $5\times10^{6}$.

The present invention provides humanized antibodies or fragments thereof which immunospecifically bind to one or more flaviviral antigens, particularly WNV antigens, and have a median effective concentration ($EC_{50}$) of less than 1 µg/ml, in an in vitro microneutralization assay. In particular, the present invention provides compositions for use in the prevention, treatment, or amelioration of one or more symptoms associated with a flaviviral infection, said compositions comprising one or more humanized antibodies or fragments thereof which immunospecifically bind to one or more one or more flaviviral antigens particularly WNV antigens and have an $EC_{50}$ of less than 0.01 nM, less than 0.025 nM, less than 0.05 nM, less than 0.1 nM, less than 0.25 nM, less than 0.5 nM, less than 0.75 nM, less than 1 nM, less than 1.25 nM, less than 1.5 nM, less than 1.75 nM, or less than 2 nM, in an in vitro microneutralization assay.

5.1.1 Antibody Conjugates

The present invention encompasses humanized antibodies, or fragments thereof, recombinantly fused or chemically conjugated (including both covalently and non-covalently conjugations) to heterologous polypeptides (i.e., an unrelated polypeptide; or portion thereof, preferably at least 10, at least 20, at least 30, at least 40, at least 50, at least 60, at least 70, at least 80, at least 90 or at least 100 amino acids of the polypeptide) to generate fusion proteins. The fusion does not necessarily need to be direct, but may occur through linker sequences. Humanized antibodies may be used, for example, to target heterologous polypeptides to particular cell types (e.g., respiratory epithelial cells), either in vitro or in vivo, by fusing or conjugating the humanized antibodies to antibodies specific for particular cell surface receptors. Antibodies fused or conjugated to heterologous polypeptides may also be used in in vitro immunoassays and purification methods using methods known in the art. See e.g., PCT Publication No. WO 93/21232; EP 439,095; Naramura et al., 1994 *Immunol. Lett.*, 39:91-99; U.S. Pat. No. 5,474,981; Gillies et al., 1992, *Proc. Natl. Acad. Sci. USA*, 89:1428-1432; and Fell et al., 1991, *J. Immunol.*, 146:2446-2452, all of which are incorporated herein by reference in their entireties.

The present invention further includes compositions comprising heterologous polypeptides fused or conjugated to antibody fragments. For example, the heterologous polypeptides may be fused or conjugated to a Fab fragment, Fd fragment, Fv fragment, F(ab)$_2$ fragment, or portion thereof. Methods for fusing or conjugating polypeptides to antibody portions are known in the art. See, e.g., U.S. Pat. Nos. 5,336,603, 5,622,929, 5,359,046, 5,349,053, 5,447,851, and 5,112,946; EP 307,434; EP 367,166; International Publication Nos. WO 96/04388 and WO 91/06570; Ashkenazi et al., 1991, *Proc. Natl. Acad. Sci. USA* 88: 10535-10539; Zheng et al., 1995, *J. Immunol.* 154:5590-5600; and Vil et al., 1992, *Proc. Natl. Acad. Sci. USA* 89:11337-11341 (said references incorporated by reference in their entireties).

Additional fusion proteins may be generated through the techniques of gene-shuffling, motif-shuffling, exon-shuffling, and/or codon-shuffling (collectively referred to as "DNA shuffling"). DNA shuffling may be employed to alter the activities of humanized antibodies of the invention or fragments thereof (e.g., antibodies or fragments thereof with higher affinities and lower dissociation rates). See, generally, U.S. Pat. Nos. 5,605,793; 5,811,238; 5,830,721; 5,834,252; and 5,837,458, and Patten et al., 1997, *Curr. Opinion Biotechnol.* 8:724-33; Harayama, 1998, *Trends Biotechnol.* 16:76; Hansson, et al., 1999, *J. Mol. Biol.* 287:265; and Lorenzo and Blasco, 1998, *BioTechniques* 24:308 (each of these patents and publications are hereby incorporated by reference in its entirety). Antibodies or fragments thereof, or the encoded antibodies or fragments thereof, may be altered by being subjected to random mutagenesis by error-prone PCR, random nucleotide insertion or other methods prior to recombination. One or more portions of a polynucleotide encoding an antibody or antibody fragment, which portions immunospecifically bind to a flaviviral antigen may be recombined with one or more components, motifs, sections, parts, domains, fragments, etc. of one or more heterologous molecules.

Moreover, the humanized antibodies of the present invention or fragments thereof can be fused to marker sequences, such as a peptide to facilitate purification. In preferred embodiments, the marker amino acid sequence is a hexa-histidine peptide, such as the tag provided in a pQE vector (QIAGEN, Inc., 9259 Eton Avenue, Chatsworth, Calif., 91311), among others, many of which are commercially available. As described in Gentz et al., 1989, Proc. Natl. Acad. Sci. USA 86:821-824, for instance, hexa-histidine provides for convenient purification of the fusion protein. Other peptide tags useful for purification include, but are not limited to, the hemagglutinin "HA" tag, which corresponds to an epitope derived from the influenza hemagglutinin protein (Wilson et al., 1984, Cell 37:767) and the "flag" tag (Knappik et al., 1994, Biotechniques, 17:754-761).

The present invention also encompasses humanized antibodies, or fragments thereof, conjugated to a diagnostic or therapeutic agent. The humanized antibodies can be used diagnostically to, for example, monitor the development or progression of a flaviviral infection as part of a clinical testing procedure to, e.g., determine the efficacy of a given treatment regimen. Detection can be facilitated by coupling the antibody, or a fragment thereof, to a detectable substance. Examples of detectable substances include various enzymes, prosthetic groups, fluorescent materials, luminescent materials, bioluminescent materials, radioactive materials, positron emitting metals, and nonradioactive paramagnetic metal ions. The detectable substance may be coupled or conjugated either directly to the antibody or indirectly, through an intermediate (such as, for example, a linker known in the art) using techniques known in the art. See, for example, U.S. Pat. No. 4,741,900 for metal ions which can be conjugated to antibodies for use as diagnostics according to the present invention. Such diagnosis and detection can be accomplished by coupling the antibody to detectable substances including, but not limited to, various enzymes, enzymes including, but not limited to, horseradish peroxidase, alkaline phosphatase, beta-galactosidase, or acetylcholinesterase; prosthetic group complexes such as, but not limited to, streptavidin/biotin and avidin/biotin; fluorescent materials such as, but not limited to, umbelliferone, fluorescein, fluorescein isothiocyanate, rhodamine, dichlorotriazinylamine fluorescein, dansyl chloride or phycoerythrin; luminescent material such as, but not limited to, luminol; bioluminescent materials such as, but not limited to, luciferase, luciferin, and aequorin; radioactive material such as, but not limited to, bismuth ($^{213}$Bi), carbon ($^{14}$C), chromium ($^{51}$Cr), cobalt ($^{57}$Co), fluorine ($^{18}$F), gadolinium ($^{153}$Gd, $^{159}$Gd), gallium ($^{68}$Ga, $^{67}$Ga), germanium ($^{68}$Ge), holmium ($^{166}$Ho), indium ($^{115}$In, $^{113}$In, $^{112}$In, $^{111}$In), iodine ($^{131}$I, $^{125}$I, $^{123}$I, $^{121}$I), lanthanium ($^{140}$La), lutetium ($^{177}$Lu), manganese ($^{54}$Mn), molybdenum ($^{99}$Mo), palladium ($^{103}$Pd), phosphorous ($^{32}$P), praseodymium ($^{142}$Pr), promethium ($^{149}$Pm), rhenium ($^{186}$Re, $^{188}$Re), rhodium ($^{105}$Rh), ruthemium ($^{97}$Ru), samarium ($^{153}$Sm), scandium ($^{47}$Sc), selenium ($^{75}$Se), strontium ($^{85}$Sr), sulfur ($^{35}$S), technetium ($^{99}$Tc), thallium ($^{201}$Ti), tin ($^{113}$Sn, $^{117}$Sn), tritium ($^{3}$H), xenon ($^{133}$Xe), ytterbium ($^{169}$Yb, $^{175}$Yb), yttrium ($^{90}$Y), zinc ($^{65}$Zn); positron emitting metals using various positron emission tomographies, and nonradioactive paramagnetic metal ions.

An antibody, or fragment thereof, may be conjugated to a therapeutic moiety such as a cytotoxin (e.g., a cytostatic or cytocidal agent), a therapeutic agent or a radioactive element (e.g., alpha-emitters, gamma-emitters, etc.). Cytotoxins or cytotoxic agents include any agent that is detrimental to cells. Examples include paclitaxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclophosphamide, busulfan, dibromomannitol, streptozotocin, mitomycin C, and cisdichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

Further, a humanized antibody, or fragment thereof, may be conjugated to a therapeutic agent or drug moiety that modifies a given biological response. Therapeutic agents or drug moieties are not to be construed as limited to classical chemical therapeutic agents. For example, the drug moiety may be a protein or polypeptide possessing a desired biological activity. Such proteins may include, for example, a toxin such as abrin, ricin A, pseudomonas exotoxin (i.e., PE-40), or diphtheria toxin, ricin, gelonin, and pokeweed antiviral protein, a protein such as tumor necrosis factor, interferons including, but not limited to, α-interferon (IFN-α), β-interferon (IFN-β), nerve growth factor (NGF), platelet derived growth factor (PDGF), tissue plasminogen activator (TPA), an apoptotic agent (e.g., TNF-α, TNF-β, AIM I as disclosed in PCT Publication No. WO 97/33899), AIM II (see, e.g., PCT Publication No. WO 97/34911), Fas Ligand (Takahashi et al., 1994, J. Immunol. 6:1567-1574), and VEGI (PCT Publication No. WO 99/23105), a thrombotic agent or an anti-angiogenic agent (e.g., angiostatin or endostatin), or a biological response modifier such as, for example, a lymphokine (e.g., interleukin-1 ("IL-1"), interleukin-2 ("IL-2"), interleukin-6 ("IL-6"), granulocyte macrophage colony stimulating factor ("GM-CSF"), and granulocyte colony stimulating factor ("G-CSF")), macrophage colony stimulating factor, ("M-CSF"), or a growth factor (e.g., growth hormone ("GH")); a protease, or a ribonuclease.

Moreover, a humanized antibody can be conjugated to therapeutic moieties such as radioactive materials or macrocyclic chelators useful for conjugating radiometal ions (see above for examples of radioactive materials). In certain embodiments, the macrocyclic chelator is 1,4,7,10-tetraazacyclododecane-N,N',N",N"-tetraacetic acid (DOTA) which can be attached to the antibody via a linker molecule. Such linker molecules are commonly known in the art and described in Denardo et al., 1998, Clin Cancer Res. 4:2483-90; Peterson et al., 1999, Bioconjug. Chem. 10:553; and Zimmerman et al., 1999, Nucl. Med. Biol. 26:943-50 each of which is herein incorporated by reference in their entirety.

Techniques for conjugating such therapeutic moieties to antibodies are well known; see, e.g., Arnon et al., "Monoclonal Antibodies For Immunotargeting Of Drugs In Cancer Therapy", in *Monoclonal Antibodies And Cancer Therapy*, Reisfeld et al. (eds.), 1985, pp. 243-56, Alan R. Liss, Inc.; Hellstrom et al., "Antibodies For Drug Delivery", in *Controlled Drug Delivery* (2nd Ed.), Robinson et al. (eds.), 1987, pp. 623-53, Marcel Dekker, Inc.; Thorpe, "Antibody Carriers Of Cytotoxic Agents In Cancer Therapy: A Review", in *Monoclonal Antibodies '84: Biological And Clinical Applications*, Pinchera et al. (eds.), 1985, pp. 475-506; "Analysis, Results, And Future Prospective Of The Therapeutic Use Of Radiolabeled Antibody In Cancer Therapy", in *Monoclonal Antibodies For Cancer Detection And Therapy*, Baldwin et al. (eds.), 1985, pp. 303-16, Academic Press; and Thorpe et al., 1982, *Immunol. Rev.*, 62:119-58.

An antibody or fragment thereof, with or without a therapeutic moiety conjugated to it, administered alone or in combination with cytotoxic factor(s) and/or cytokine(s) can be used as a therapeutic. Alternatively, an antibody can be conjugated to a second antibody to form an antibody heteroconjugate as described by Segal in U.S. Pat. No. 4,676,980, which is incorporated herein by reference in its entirety.

Antibodies may also be attached to solid supports, which are particularly useful for immunoassays or purification of the target antigen. Such solid supports include, but are not limited to, glass, cellulose, polyacrylamide, nylon, polystyrene, polyvinyl chloride or polypropylene.

5.2 Preparation of Humanized Antibodies

The invention encompasses nucleotide sequences that encode the CDR-grafted heavy and light chains, cloning and expression vectors containing the nucleotide sequences, host cells transformed with the nucleotide sequences, and methods for the production of the CDR-grafted chains and antibody molecules comprising the nucleotide sequences in the transformed host cells.

The invention encompasses donor amino acid sequences, which encode antibodies that immunospecifically bind a West Nile Virus antigen, such as those disclosed in U.S. Provisional Application No. 60/581,819, filed on Jun. 21, 2004, incorporated herein by reference in its entirety. In a specific embodiment, the donor amino acid sequence encodes for the monoclonal antibody produced from clone E16, E24 and E34, or other monoclonal antibodies produced by immunization methods of the invention as disclosed in U.S. Provisional Application No. 60/581,819 filed on Jun. 21, 2004, incorporated herein by reference in its entirety. In another specific embodiment, the donor amino acid sequence encodes for the antibody produced from clone E16-1.1, E16-1.2, E16-2.1, E16-2.2, E16-3.1, or E16-3.2. Donor murine antibodies may be produced using any method known in the art, including those disclosed in U.S. Provisional Application No. 60/581,819, filed on Jun. 21, 2004, incorporated herein by reference in its entirety.

The invention also encompass polynucleotides that encode for donor amino acid sequences that hybridize under various stringency, e.g., high stringency, intermediate or low stringency conditions, to polynucleotides that encode for the monoclonal antibody produced from clone E16, E24 and E34, or other monoclonal antibodies produced by immunization methods of the invention as disclosed in U.S. Provisional Application No. 60/581,819 filed on Jun. 21, 2004. The hybridization can be performed under various conditions of stringency. By way of example and not limitation, procedures using conditions of low stringency are as follows (see also Shilo and Weinberg, 1981, *Proc. Natl. Acad. Sci. U.S.A.* 78, 6789-6792). Filters containing DNA are pretreated for 6 h at 40° C. in a solution containing 35% formamide, 5×SSC, 50 mM Tris-HCl (pH 7.5), 5 mM EDTA, 0.1% PVP, 0.1% Ficoll, 1% BSA, and 500 µg/ml denatured salmon sperm DNA. Hybridizations are carried out in the same solution with the following modifications: 0.02% PVP, 0.02% Ficoll, 0.2% BSA, 100 µg/ml salmon sperm DNA, 10% (wt/vol) dextran sulfate, and 5-20×10$^6$ cpm $^{32}$P-labeled probe is used. Filters are incubated in hybridization mixture for 18-20 h at 40° C., and then washed for 1.5 h at 55° C. in a solution containing 2×SSC, 25 mM Tris-HCl (pH 7.4), 5 mM EDTA, and 0.1% SDS. The wash solution is replaced with fresh solution and incubated an additional 1.5 h at 60° C. Filters are blotted dry and exposed for autoradiography. If necessary, filters are washed for a third time at 65-68° C. and re-exposed to film. Other conditions of low stringency which may be used are well known in the art (e.g., as employed for cross-species hybridizations). By way of example and not limitation, procedures using conditions of high stringency are as follows. Prehybridization of filters containing DNA is carried out for 8 h to overnight at 65° C. in buffer composed of 6×SSC, 50 mM Tris-HCl (pH 7.5), 1 mM EDTA, 0.02% PVP, 0.02% Ficoll, 0.02% BSA, and 500 µg/ml denatured salmon sperm DNA. Filters are hybridized for 48 h at 65° C. in prehybridization mixture containing 100 µg/ml denatured salmon sperm DNA and 5-20×10$^6$ cpm of $^{32}$P-labeled probe. Washing of filters is done at 37° C. for 1 h in a solution containing 2×SSC, 0.01% PVP, 0.01% Ficoll, and 0.01% BSA. This is followed by a wash in 0.1×SSC at 50° C. for 45 min before autoradiography. Other conditions of high stringency which may be used are well known in the art. Selection of appropriate conditions for such stringencies is well known in the art (see e.g., Sambrook et al., 1989, Molecular Cloning, A Laboratory Manual, 2d Ed., Cold Spring Harbor Laboratory Press, Cold Spring Harbor, N.Y.; see also, Ausubel et al., eds., in the Current Protocols in Molecular Biology series of laboratory technique manuals,© 1987-1997, Current Protocols,© 1994-1997 John Wiley and Sons, Inc.; see especially, Dyson, 1991, "Immobilization of nucleic acids and hybridization analysis," In: Essential Molecular Biology: A Practical Approach, Vol. 2, T. A. Brown, ed., pp. 111-156, IRL Press at Oxford University Press, Oxford, UK).

The polynucleotides may be obtained, and the nucleotide sequence of the polynucleotides determined, by any method known in the art.

DNA sequences which encode the acceptor amino acid sequences may be obtained by any method known to one skilled in the art. For example, DNA sequences coding for preferred human acceptor framework sequences include, but are not limited to, FR segments from the human germline VH segement VH1-8 and JH6 and the human germline VL segment VK-B3, as depicted in Table 5.

TABLE 5

| | | |
|---|---|---|
| VH1-18 | CAGGTTCAGCTGGTGCAGTCTGGAGCTGAGGTGAAGAAGCCTGGGGCCTCAGTG<br>AAGGTCTCCTGCAAGGCTTCTGGTTACACCTTTACCAGCTATGGTATCAGCTGGG<br>TGCGACAGGCCCCTGGACAAGGGCTTGAGTGGATGGGATGGATCAGCGCTTACA<br>ATGGTAACACAAACTATGCACAGAAGCTCCAGGGCAGAGTCACCATGACCACAG<br>ACACATCCACGAGCACAGCCTACATGGAGCTGAGGAGCCTGAGATCTGACGACA<br>CGGCCGTGTATTACTGTGCGAGAGA | SEQ ID<br>NO:54 |
| JH6 | ATTACTACTACTACTACGGTATGGACGTCTGGGGGCAAGGGACCACGGTCACCGT<br>CTCCTCAG | SEQ ID<br>NO:55 |
| VKB-3 | GACATCGTGATGACCCAGTCTCCAGACTCCCTGGCTGTGTCTCTGGGCGAGAGGG<br>CCACCATCAACTGCAAGTCCAGCCAGAGTGTTTTATACAGCTCCAACAATAAGAA<br>CTACTTAGCTTGGTACCAGCAGAAACCAGGACAGCCTCCTAAGCTGCTCATTTAC<br>TGGGCATCTACCCGGGAATCCGGGGTCCCTGACCGATTGAGTGGCAGCGGGTCTG<br>GGACAGATTTCACTCTCACCATCAGCAGCCTGCAGGCTGAAGATGTGGCAGTTTA<br>TTACTGTCAGCAATATTATAGTACTCCTCC | SEQ ID<br>NO:56 |

A polynucleotide encoding an antibody may be generated from nucleic acid from a suitable source (e.g., a cDNA library generated from, or nucleic acid, preferably poly A+ RNA, isolated from, any tissue or cells expressing the antibody, such as hybridoma cells selected to express a humanized antibody of the invention) by hybridization with Ig specific probes and/or PCR amplification using synthetic primers hybridizable to the 3' and 5' ends of the sequence or by cloning using an oligonucleotide probe specific for the particular gene sequence to identify, e.g., a cDNA clone from a cDNA library that encodes the antibody. Amplified nucleic acids generated by PCR may then be cloned into replicable cloning vectors using any method well known in the art.

Once the nucleotide sequence of the antibody is determined, the nucleotide sequence of the antibody may be manipulated using methods well known in the art for the manipulation of nucleotide sequences, e.g., recombinant DNA techniques, site directed mutagenesis, PCR, etc. (see, for example, the techniques described in Sambrook et al., 1990, *Molecular Cloning, A Laboratory Manual*, 2d Ed., Cold Spring Harbor Laboratory, Cold Spring Harbor, N.Y. and Ausubel et al., eds., 1998, Current Protocols in Molecular Biology, John Wiley & Sons, NY, which are both incorporated by reference herein in their entireties), to generate antibodies having a different amino acid sequence, for example to create amino acid substitutions, deletions, and/or insertions.

In a specific embodiment, one or more of the CDRs are inserted within framework regions using routine recombinant DNA techniques. The framework regions may be naturally occurring or consensus framework regions, and preferably human framework regions (see, e.g., Chothia et al., 1998, *J. Mol. Biol.* 278: 457-479 for a listing of human framework regions). Preferably, the polynucleotide generated by the combination of the framework regions and CDRs encodes an antibody that specifically binds to a flaviviral antigen. Preferably, as discussed supra, one or more amino acid substitutions may be made within the framework regions, and, preferably, the amino acid substitutions improve binding of the humanized antibodies of the invention to a flaviviral antigen.

The humanized antibodies of the present invention may be produced by any method known in the art useful for the production of polypeptides, e.g., in vitro synthesis, recombinant DNA production, and the like. Preferably, the humanized antibodies are produced by recombinant DNA technology. The humanized WNV specific antibodies of the invention may be produced using recombinant immunoglobulin expression technology. The recombinant production of immunoglobulin molecules, including humanized antibodies are described in U.S. Pat. No. 4,816,397 (Boss et al.), U.S. Pat. Nos. 6,331,415 and 4,816,567 (both to Cabilly et al.), U.K. patent GB 2,188,638 (Winter et al.), and U.K. patent GB 2,209,757; all of which are incorporated herein by reference in their entireties. Techniques for the recombinant expression of immunoglobulins, including humanized immunoglobulins, can also be found, in Goeddel et al., Gene Expression Technology Methods in Enzymology Vol. 185 Academic Press (1991), and Borreback, Antibody Engineering, W. H. Freeman (1992). Additional information concerning the generation, design and expression of recombinant antibodies can be found in Mayforth, Designing Antibodies, Academic Press, San Diego (1993).

An exemplary process for the production of the recombinant humanized antibodies of the invention may comprise the following: a) constructing, by conventional molecular biology methods, an expression vector comprising an operon that encodes an antibody heavy chain in which the CDRs and a minimal portion of the variable region framework that are required to retain donor antibody binding specificity are derived from a non-human immunoglobulin, such as the murine WNV monoclonal antibody, and the remainder of the antibody is derived from a human immunoglobulin, thereby producing a vector for the expression of a humanized antibody heavy chain; b) constructing, by conventional molecular biology methods, an expression vector comprising an operon that encodes an antibody light chain in which the CDRs and a minimal portion of the variable region framework that are required to retain donor antibody binding specificity are derived from a non-human immunoglobulin, such as the murine WNV monoclonal antibody, and the remainder of the antibody is derived from a human immunoglobulin, thereby producing a vector for the expression of humanized antibody light chain; c) transferring the expression vectors to a host cell by conventional molecular biology methods to produce a transfected host cell for the expression of humanized anti-WNV antibodies; and d) culturing the transfected cell by conventional cell culture techniques so as to produce humanized anti-WNV antibodies. Host cells may be cotransfected with two expression vectors of the invention, the first vector containing an operon encoding a heavy chain derived polypeptide and the second containing an operon encoding a light chain derived polypeptide. The two vectors may contain different selectable markers but, with the exception of the heavy and light chain coding sequences, are preferably identical. This procedure provides for equal expression of heavy and light chain polypeptides. Alternatively, a single vector may be used which encodes both heavy and light chain polypeptides. The coding sequences for the heavy and light chains may comprise cDNA or genomic DNA or both. The host cell used to express the recombinant humanized antibodies of the invention may be either a bacterial cell such as *Escherichia coli*, or preferably a eukaryotic cell. Preferably, a mammalian cell such as a chinese hamster ovary cell or HEK-293 cells, may be used. The choice of expression vector is dependent upon the choice of host cell, and may be selected so as to have the desired expression and regulatory characteristics in the selected host cell. Other cell lines that may be used include, but are not limited to, CHO-K1, NSO, and PER.C6 (Crucell, Leiden, Netherlands).

In a specific embodiment the method for producing a humanized WNV antibody comprises the following: RNA from hybridoma cells of E16 is converted to cDNA and the VH and VL segments are PCR amplified using, for example, the RLM-RACE kit (Ambion, Inc.). Gene specific primers for the VH are used. Examples of such primers for VH include: SJ15R, SEQ ID NO: 57 (5' GGT CAC TGT CAC TGG CTC AGG G 3') and SJ16R, SEQ ID NO: 58 (5' AGG CGG ATC CAG GGG CCA GTG GAT AGA C 3'), and for VL include SJ17R, SEQ ID NO: 59 (5' GCA CAC GAC TGA GGC ACC TCC AGA TG 3') and SJ18R, SEQ ID NO: 60 (5' CGG CGG ATC CGA TGG ATA CAG TTG GTG CAG CAT C 3'). The RACE product is inserted into a plasmid, e.g., pCR2.1-TOPO using a TOPO TA Cloning kit (Invitrogen, Inc.). The resulting plasmids are then subjected to DNA sequencing to determine the VH and VL sequences for E16. The resulting sequences are translated and the predicted amino acid sequence determined for each. From these sequences the framework (FR) and complementarity determining (CDR) regions are identified as defined by Kabat. The mouse VH is then joined to a human C-Gammal constant region and an Ig leader sequence and inserted into pCI-neo for mammalian expression. The mouse VL is joined to a human C-kappa segment and an Ig leader sequence and also cloned into pCI-neo for mammalian expression. The humanized E16 VH consists of the FR segments from the human germline VH segment VH1-18 and JH6, and the CDR regions of the E16 VH. The humanized E16 VL consists of the FR segments of the human germline VL segment VK-B3, and the CDR regions of E16 VL. The humanized VH and VL segments are assembled de novo from oligonucleotides combined and amplified by PCR. The resulting fragment is then combined by PCR with a leader sequence and the appropriate constant region segment cloned into the expression vector pCI-neo. The DNA sequence of the resulting plasmids is confirmed by sequence analysis. After this procedure light chain segments having predicted humanized E16 VL sequence are identified. Humanized E24 and humanized E34 antibodies are made in a similar manner.

The general methods for construction of the vectors of the invention, transfection of cells to produce the host cell of the invention, culture of cells to produce the humanized antibodies of the invention are all conventional molecular biology methods. Likewise, once produced, the recombinant humanized antibodies of the invention may be purified by standard procedures of the art, including cross-flow filtration, ammonium sulphate precipitation, affinity column chromatography, gel electrophoresis and the like.

The humanized WNV specific antibodies of the present invention may be used in conjunction with, or attached to, other antibodies (or parts thereof) such as human or humanized monoclonal antibodies. These other antibodies may be reactive with other markers (epitopes) characteristic for the disease against which the humanized antibodies of the invention are directed or may have different specificities chosen, for example, to recruit molecules or cells of the human immune system to the infected cells. The humanized antibodies of the invention (or parts thereof) may be administered with such antibodies (or parts thereof) as separately administered compositions or as a single composition with the two agents linked by conventional chemical or by molecular biological methods. Additionally the diagnostic and therapeutic value of the humanized antibodies of the invention may be augmented by labelling the humanized antibodies with labels that produce a detectable signal (either in vitro or in vivo) or with a label having a therapeutic property. Some labels, e.g., radionucleotides, may produce a detectable signal and have a therapeutic property. Examples of radionuclide labels include, but are not limited to, $^{125}I$, $^{131}I$, and $^{14}C$. Examples of other detectable labels include a fluorescent chromophore such as fluorescein, phycobiliprotein or tetraethyl rhodamine for fluorescence microscopy, an enzyme which produces a fluorescent or colored product for detection by fluorescence, absorbance, visible color or agglutination, which produces an electron dense product for demonstration by electron microscopy; or an electron dense molecule such as ferritin, peroxidase or gold beads for direct or indirect electron microscopic visualization.

The invention encompasses standard recombinant DNA methods for preparing DNA sequences which code for the CDR-grafted humanized antibodies of the invention. DNA sequences may be synthesized completely or in part using oligonucleotide synthesis techniques. Methods for oliogonucleotide directed synthesis are well known in the art. The invention further encompasses site-directed mutagenesis methods such as those known in the art.

Any suitable host cell/vector system may be used for expression of the DNA sequences coding for the CDR-grafted heavy and light chains. Bacterial, e.g., *E. coli*, and other microbial systems may be used, in particular for expression of antibody fragments such as Fab and (Fab')2 fragments, and especially FV fragments and single chain antibody fragments, e.g., single chain FVs. Eucaryotic systems, e.g., mammalian host cell expression systems, may be used for production of larger CDR-grafted antibody products, including complete antibody molecules. Suitable mammalian host cells include CHO cells and myeloma or hybridoma cell lines. Other cell lines that may be used include, but are not limited to, CHO-K1, NSO, and PER.C6 (Crucell, Leiden, Netherlands).

Antibody fragments which recognize specific epitopes may be generated by known techniques. For example, Fab and $F(ab')_2$ fragments may be produced by proteolytic cleavage of immunoglobulin molecules, using enzymes such as papain (to produce Fab fragments) or pepsin (to produce $F(ab')_2$ fragments). $F(ab')_2$ fragments contain the complete light chain, and the variable region, the CH1 region and at least a portion of the hinge region of the heavy chain.

Humanized antibodies of the invention can also be generated using various phage display methods known in the art. In phage display methods, functional antibody domains are displayed on the surface of phage particles which carry the polynucleotide sequences encoding them. In a particular embodiment, such phage can be utilized to display antigen binding domains, such as Fab and Fv or disulfide-bond stabilized Fv, expressed from a repertoire or combinatorial antibody library (e.g., human or murine). Phage expressing an antigen binding domain that binds the antigen of interest can be selected or identified with antigen, e.g., using labeled antigen or antigen bound or captured to a solid surface or bead. Phage used in these methods are typically filamentous phage, including fd and M13. The antigen binding domains are expressed as a recombinantly fused protein to either the phage gene III or gene VIII protein. Examples of phage display methods that can be used to make the immunoglobulins, or fragments thereof, of the present invention include those disclosed in Brinkman et al., 1995, *J. Immunol. Methods* 182:41-50; Ames et al., 1995, *J. Immunol. Methods* 184:177-186; Kettleborough et al., 1994, *Eur. J. Immunol.*, 24:952-958; Persic et al., 1997, *Gene* 187:9-18; Burton et al., 1994, *Advances in Immunology* 57:191-280; PCT Application No. PCT/GB91/01134; PCT Publications WO 90/02809; WO 91/10737; WO 92/01047; WO 92/18619; WO 93/11236; WO 95/15982; WO 95/20401; and U.S. Pat. Nos. 5,698,426; 5,223,409; 5,403,484; 5,580,717; 5,427,908; 5,750,753; 5,821,047; 5,571,698; 5,427,908; 5,516,637; 5,780,225; 5,658,727; 5,733,743 and 5,969,108; each of which is incorporated herein by reference in its entirety.

As described in the above references, after phage selection, the antibody coding regions from the phage can be isolated and used to generate whole antibodies, including human antibodies, or any other desired fragments, and expressed in any desired host, including mammalian cells, insect cells, plant cells, yeast, and bacteria, e.g., as described in detail below. For example, techniques to recombinantly produce Fab, Fab' and $F(ab')_2$ fragments can also be employed using methods known in the art such as those disclosed in PCT Publication WO 92/22324; Mullinax et al., *BioTechniques*, 12(6):864-869, 1992; and Sawai et al., *AJRI*, 34:26-34, 1995; and Better et al., *Science*, 240:1041-1043, 1988 (each of which is incorporated by reference in its entirety). Examples of techniques which can be used to produce single-chain Fvs and antibodies include those described in U.S. Pat. Nos. 4,946,778 and 5,258,498; Huston et al., 1991, *Methods in Enzymology* 203:46-88; Shu et al., 1993, *Proc. Natl. Acad. Sci. USA* 90:7995-7999; and Skerra et al., 1988, *Science* 240:1038-1040.

Phage display technology can be used to increase the affinity of humanized antibodies of the invention for its cognate antigen, e.g., flaviviral antigen. This technique would be useful in obtaining high affinity antibodies that could be used in the combinatorial methods of the invention. This technology, referred to as affinity maturation, employs mutagenesis or CDR walking and re-selection using a flaviviral antigen or an antigenic fragment thereof to identify antibodies that bind with higher affinity to the antigen when compared with the initial or parental antibody (See, e.g., Glaser et al., 1992, *J. Immunology* 149:3903). Mutagenizing entire codons rather than single nucleotides results in a semi-randomized repertoire of amino acid mutations. Libraries can be constructed consisting of a pool of variant clones each of which differs by a single amino acid alteration in a single CDR and which contain variants representing each possible amino acid substitution for each CDR residue. Mutants with increased binding affinity for the antigen can be screened by contacting the immobilized mutants with labeled antigen. Any screening method known in the art can be used to identify mutant antibodies with increased avidity to the antigen (e.g., ELISA) (See Wu et al., 1998, *Proc Natl. Acad. Sci. USA* 95:6037; Yelton et al., 1995, *J. Immunology* 155:1994). CDR walking which randomizes the light chain is also possible (See Schier et al., 1996, *J. Mol. Bio.* 263:551).

5.3 Screening For Biological Properties

The humanized antibodies of the invention may be characterized for specific binding to a WNV antigen using any immunological or biochemical based method known in the art for characterizing, including quantitating the interaction of the antibody to a WNV antigen. Specific binding of the humanized antibodies of the invention to a WNV antigen may be determined, for example, using immunological or biochemical based methods including, but not limited to, an ELISA assay, surface plasmon resonance assays, immunoprecipitation assay, affinity chromatography, fluorescence activated cell sorting (FACS), and equilibrium dialysis. Immunoassays which can be used to analyze immunospecific binding and cross-reactivity of the humanized antibodies of the invention include, but are not limited to, competitive and non-competitive assay systems using techniques such as western blots, radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, protein A immunoassays, to name but a few. Such assays are routine and well known in the art (see, e.g., Ausubel et al., eds, 1994, Current Protocols in Molecular Biology, Vol. 1, John Wiley & Sons, Inc., New York, which is incorporated by reference herein in its entirety).

Humanized antibodies of the invention may be characterized by epitope mapping, so that humanized antibodies may be selected that have the greatest specificity for for a WNV antigen, e.g., E protein. Epitope mapping methods of antibodies are well known in the art and encompassed within the methods of the invention. In certain embodiments fusion proteins comprising one or more regions of an WNV antigen may be used in mapping epitopes of the humanized antibodies of the invention.

To define distinct structural epitopes that are present on WNV protein, e.g., E proteins of WNV, the invention encompasses competition-binding studies using an ELISA and/or surface plasmon resonance based assays such as those disclosed in (Lanciotti et al., 2000, J Clin Microbiol 38:4066-71; Modis et al., 2003, Proc Natl Acad Sci USA 100:6986-91).

ELISA based assays are well known in the art and encompassed within the instant invention. Such assays are routine and well known in the art (see, e.g., Ausubel et al., eds, 1994, Current Protocols in Molecular Biology, Vol. 1, John Wiley & Sons, Inc., New York, which is incorporated by reference herein in its entirety). In an exemplary assay, in the ELISA format, small quantities of individual purified monoclonal antibodies will be labeled with biotin. Competing unlabeled monoclonal antibodies will be bound to recombinant E proteins in microtiter plates. Subsequently, biotinylated monoclonal antibodies will be added, and after washing, detected with peroxidase-conjugated streptavidin. Competition for an individual structural epitope will be defined as a >40% decrease in the mean $OD_{450}$ across multiple experiments after comparing binding of biotinylated monoclonal antibodies plus competing monoclonal antibodies with binding of biotinylated monoclonal antibodies alone.

Surface plasmon resonance based assays are known in the art and encompassed within the instant invention. For a review of SPR-based technology see Mullet et al., 2000, *Methods* 22: 77-91; Dong et al., 2002, *Review in Mol. Biotech.*, 82: 303-23; Fivash et al., 1998, *Current Opinion in Biotechnology* 9: 97-101; Rich et al., 2000, *Current Opinion in Biotechnology* 11: 54-61; all of which are incorporated herein by reference in their entirety. Additionally, any of the SPR instruments and SPR based methods for measuring protein-protein interactions described in U.S. Pat. Nos. 6,373,577; 6,289,286; 5,322,798; 5,341,215; 6,268,125 are contemplated in the methods of the invention, all of which are incorporated herein by reference in their entirety. In an exemplary assay, in the BIAcore format, monoclonal antibodies are reacted sequentially with a surface onto which the antigen WNV E protein has been coupled, leading to an increase in the SPR signal. After saturation of all of the available sites by a first antibody, the addition of a competing monoclonal antibody will should not increase the SPR signal appreciably. A non-competing monoclonal antibody, on the other hand will increase the overall signal independent of the first binding level achieved. Since the maximum signal obtained with different mAbs may vary, each assay will be repeated in the reverse order of monoclonal antibody addition. Preferably the invention encompasses characterizing the humanized antibodies of the invention using both an ELISA and a BIAcore based assay to define a functional epitope map using the panel of mAbs obtained.

The invention encompasses epitope mapping using one or more of the following three strategies: (1) directed evolution of an WNV antigen, e.g., E protein on the surface of yeast; (2) synthetic peptides; (3) WNV protein chimeras. An exemplary yeast display system for epitope mapping of the humanized WNV specific antibodies of the invention may comprise the following: expressing the entire ectodomain of WNV E protein or domain III alone on the surface of yeast; using the yeast displaying these proteins to identify humanized antibodies that are domain III-specific; a combinatorial library of E variants will be generated by error-prone PCR and used to map antibody epitopes at the amino acid level. The entire ectodomain or domain III of the WNV E protein will be mutagenized by error-prone PCR; importantly, an N-terminal Xpress™ peptide tag will be added to track E protein surface expression independently. Mutagenesis will be achieved by changing the $Mg^{2+}:Mn^{2+}$ ratio (to ~6.6:1) in the initial PCR reaction to obtain a nucleotide error rate of approximately 0.5% using a method such as that disclosed in Chothia et al., 1989, Nature 342:877-83, or on average 1 amino acid change per variant. These variants will be cloned into a yeast expression vector, e.g., pYD1, with the goal of generating ~$10^5$ independent transformants. Libraries will be constructed by cloning or homologous recombination of PCR-mutagenized segments with the parental vector in yeast cells, a technique that gives rise to libraries of high diversity (See, Chothia et al., 1989, Nature 342:877-83; Holgate et al., 2001, Curr Med Res Opin 17:233-40). To isolate variants that have lost a particular mAb epitope, an initial depletion step will be performed with protein G-coated magnetic beads using a method disclosed in Pogodina et al., 1983, Arch Virol 75:71-86. The remaining yeast cells will be sorted by two-color flow cytometry using a directly conjugated mAb to the Xpress tag and the individual antibody to the E protein that is being mapped. Yeast cells that are $Xpress^{HI}$ and anti-E low or null will be collected, cultivated and subjected to repeated rounds of sorting and then immunostained with other anti-E mAbs to confirm that large-scale structural changes have not occurred. Finally, the E protein variants from individual clones will be sequenced; plasmids can be recovered from yeast by *E.coli* rescue using a commercially available kit (Zymo Research, Orange, Calif.) and used to prepare DNA for sequencing. Under optimal screening conditions, flow cytometry sorting should allow fine discrimination between mutants with antibody specificity changes. In some instances, a single amino acid change may not be sufficient to abrogate mAb recognition. For mAbs that show decreased but detectable expression after the initial screen, serial mutagenesis will be undertaken.

In other embodiments, the invention encompasses methods whereby mAb binding sites may be mapped by analysis of binding to synthetic peptides or recombinant E protein fragments. Initially, about 30 overlapping peptides (e.g., 15-20 amino acids in length) will be synthesized; these peptides will be designed based on previous mapping studies with the related DEN (see, e.g., Kulkarni et al., 1991, Viral Immunol 4:73-82; Kurane et al., 1984, J Virol 52:223-30) and Murray Valley encephalitis viruses (see, e.g., Kurane et al., 1992, Semin Immunol 4:121-7) and the three-dimensional crystal structure of DEN (see, e.g., Kacani et al., 2001, Mol Immunol 38:241-7), tick-borne encephalitis (see, e.g., Kramer et al., 2001, Ann N Y Acad Sci 951:84-93), and WNV E proteins. mAbs will be mapped on the basis of their ability to bind peptides adsorbed to microtiter plates using a standard ELISA assay.

Because some of the mAbs may bind non-linear epitopes or epitopes not correctly displayed by the yeast cells, the invention further encompasses an alternate strategy using recombinantly derived fragments of the E protein. The extracellular domain of DEN and WNV E protein will each be expressed and secreted in mammalian cells (HEK-293) using a mammalian expression vector (e.g., pCDNA3.1). E protein chimera will be generated such that sub-domains of the WNV E protein are replaced by the equivalent regions of DEN (or vice versa). Finally, WNV and DEN E proteins chimera will be made in which specific segments or amino acid residues of domain III are substituted. Binding of the antibodies to this each of these proteins will be determined by ELISA and used for fine structural mapping.

The invention encompasses characterization of the humanized antibodies produced by the methods of the invention using certain characterization assays for identifying the function of the humanized antibodies of the invention, particularly the activity to inhibit a flaviviral infection using in vitro and in vivo based assays. The characterization assays of the invention can be cell-based or cell-free assays.

The invention encompasses characterizing the humanized antibodies of the invention using qualitative based screens, e.g., an ELISA assay, preferably as a primary screen for characterizing the humanized antibodies of the invention. The invention provides an ELISA that detects humanized antibodies against adsorbed purified E protein as the primary screen. An exemplary ELISA based assay for characterizing the humanized antibodies of the invention comprises the following: when intact virus is used as an immunogen, lysates from WNV-infected BHK21 cells will be substituted to insure that additional E protein epitopes are present during the screen; Positive clones will be confirmed for immunoreactivity with WNV-infected cells by flow cytometry. To obtain mAbs that recognize conserved WNV epitopes, immunoreactivity with other (lineage I and II) WNV strains will be confirmed. To avoid possible complications associated with *flavivirus* cross-reactive antibodies (e.g., ADE associated with heterologous *flavivirus* infection), candidate mAbs that positively react with WNV proteins will be tested for binding to Vero cells infected with DEN, yellow fever, or St. Louis encephalitis viruses; only WNV-specific mAbs will be used for further studies. Because different mAb isotypes may display different effector functions in vivo, isotypes will be determined using a commercially available ELISA kit.

In other embodiments, the invention encompasses quantitative functional screens to characterize the potential mechanisms of mAb-mediated inhibition of WNV infection. A scoring system will be generated from each assay to identify mAbs with the greatest inhibitory activity. The invention encompasses characterization of the anitbodies of the invention using virus neutralization assays using methods known in the art and encompassed herein. In an exemplary assay, the ability to neutralize WNV infection in cell culture will be determined using a plaque reduction neutralization assay (PRNT) with BHK21 cells. For the anti-E mAbs, a neutralizing index will be generated. Using a standard concentration (e.g., 100 µg/ml) of purified antibody, a point scale will be assigned from the $PRNT_{50}$ value: <1/10=0 points, 1/10-1/100=1 point, >1/100=2 points. The invention encompasses characterization of the anitbodies of the invention using complement-mediated cytolysis assays using methods known in the art and encompassed herein. The ability of antibodies to trigger complement-mediated lysis of WNV-infected cells will be assessed by a standard target cell lysis assay (see, e.g., Stanley et al., 1986, J Virol 58:107-115). BHK21 cells will be infected with WNV for 24 hours and labeled with $^{51}Cr$. Washed cells will be incubated with purified mAbs and guinea pig complement (1 h at 37° C.). Supernatants will be harvested and antibody-dependent complement-mediated cell lysis will be measured by scintillation counting. A point scale will be assigned based on the percentage of cells that are specifically lysed by mAb and complement: <10%=0 points, 10-40%=1 point, >40%=2 points. In yet other embodiments, the invention encompasses characterization of the anitbodies of the invention using Complement-fixation on virus. The ability of mAbs to bind to virus and fix complement directly in solution will be evaluated by detecting cleavage products of C3 that occur after fixation using methods known in the art such as those disclosed in Manderson et al., 2001, J Exp Med 194:747-56). WNV or DEN virus (negative control) will be incubated with anti-WNV mAbs against E in the presence of serum from wild type mice at 37° C. to enable C3 binding. Samples will be denatured with detergent, immunoprecipitated with goat anti-mouse C3, and subjected to Western blot analysis with rabbit polyclonal antibodies against C3. If complement fixation occurs, the C3α chain ($M_r$ of 100) will be cleaved and increased levels of C3d ($M_r$ of 40) will be detected. As an additional control, mAbs and WNV will also be incubated with factor B −/− and C1q −/− serum. If complement fixation on virus requires antibodies (and uses the classical pathway of complement activation), a deficiency of C1q but not factor B will prevent conversion of C3 to C3d. The use of these complement-deficient sera will confirm that antibody binding triggers C3 activation directly and rule out C3 activation that occurs spontaneously in solution (Manderson et al., 2001, J Exp Med 194:747-56) or via the alternative pathway. A point scale will be assigned based on whether mAbs facilitate direct complement-fixation on WNV: no C3 fixation=0 points, C3 fixation=2 points.

In yet other embodiments, the invention encompasses characterization of the humanized antibodies of the invention using Antibody-dependent cell-mediated cytotoxicity (ADCC) assays known in the art and encompassed herein. The ability of mAbs to promote ADCC of WNV-infected cells will be evaluated according to previously described assays (Kurane et al., 1984, J Virol 52:223-30; Meguro et al., 1979, J Immunol 122:2521-6; Zhang et al., 1992, Acta Virol 36:533-40). MC57GL mouse fibroblasts will be infected with WNV for 24 hours, labeled with $^{51}$Cr, incubated with purified anti-WNV or control mAbs, and mixed with different concentrations of washed syngeneic peripheral blood mononuclear cells (PBMC) isolated from WNV-naïve mice. After incubation (12 to 16 h at 37° C.), supernatants will be harvested and ADCC activity will be measured by scintillation counting. A point scale will be assigned based on the percentage of cells that are specifically lysed in the presence of mAb with an effector:target ratio of 50:1: <10%=0 points, 10-40%=1 point, >40%=2 points.

Because passive administration of high-affinity non-neutralizing mAbs can prevent lethal encephalitis caused by Sindbis virus (Schmaljohn et al., 1982, Nature 297:70-2), mAbs will also be evaluated for their relative avidity. Avidity will be assessed by the constant antigen varying antibody method (Tyler et al., 1993, J Virol 67:3446-53; Virgin et al., 1991, J Virol 65:6772-81). A fixed quantity of recombinant E protein will be adsorbed to a microtiter well, incubated with varying concentrations of $I^{125}$-labeled purified mAb, and evaluated for reactivity by scintillation counting. Competition studies will be performed with a 100-fold excess of unlabeled antibody so that a $K_D$ can be determined by Scatchard analysis. A point scale will be assigned based on the relative avidity of the bivalent mAbs for purified WNV proteins: >$10^{-6}$ M=0 points, $10^{-6}$-$10^{-8}$ M=1 point, <$10^{-8}$ M=2 points.

As mentioned, the point system is designed to facilitate ranking and selection of the mAbs with the greatest potential inhibitory activity of three categories will be selected for further competition binding and in vivo studies.

5.4 Prophylactic and Therapeutic Methods

The present invention encompasses antibody-based therapies which involve administering one or more of the humanized antibodies of the invention to an animal, preferably a mammal, and most preferably a human, for preventing, treating, or ameliorating one or more symptoms associated with a flaviviral infection, particularly an WNV infection. Prophylactic and therapeutic compounds of the invention include, but are not limited to, the humanized antibodies of the invention (including fragments, analogs and derivatives thereof as described herein) and nucleic acids encoding the humanized antibodies of the invention (including fragments, analogs and derivatives thereof) and anti-idiotypic antibodies as described herein. Humanized antibodies of the invention or fragments thereof may be provided in pharmaceutically acceptable compositions as known in the art or as described herein.

Humanized antibodies of the present invention or fragments thereof that function as antagonists of a flaviviral infection can be administered to a mammal, preferably a human, to treat, prevent or ameliorate one or more symptoms associated with a flaviviral infection. For example, humanized antibodies or fragments thereof which disrupt or prevent the interaction between a flaviviral antigen and its host cell receptor may be administered to a mammal, preferably a human, to treat, prevent or ameliorate one or more symptoms associated with a flaviviral infection.

The present invention provides methods for treating, preventing, or ameliorating a flaviviral infection by administration of one or more humanized antibodies of the invention. In a specific embodiment, the invention encompasses methods for treating, preventing, or ameliorating a WNV infection comprising administering a humanized antibody that immunospecifically binds a structural protein of WNV, e.g., E protein. In another embodiment, the invention encompasses methods for treating, preventing, or ameliorating a WNV infection comprising administering a first humanized antibody that immunospecifically binds a structural protein of WNV, e.g., E protein, and a second antibody that binds a non-structural protein of WNV, e.g., NS1 protein. Although not intending to be bound by a particular mechanism of action such combination regimens are more effective than single antibody treatment regimens because the RNA-dependent RNA polymerase of WNV has a high error rate and thus a potential to rapidly alter immunodominant residues. In other specific embodiments, the invention encompasses methods for treating, preventing, or ameliorating a WNV infection comprising administering a first antibody that immunospecifically binds an epitope of a structural protein of WNV, e.g., E protein, and a second antibody that binds the same structural protein of WNV but binds a different epitope.

In a specific embodiment, a humanized antibody or fragment thereof prevents *flavivirus*, e.g. WNV from binding to its host cell receptor by at least 99%, at least 95%, at least 90%, at least 85%, at least 80%, at least 75%, at least 70%, at least 60%, at least 50%, at least 45%, at least 40%, at least 45%, at least 35%, at least 30%, at least 25%, at least 20%, or at least 10% relative to flaviviral binding to its host cell receptor in the absence of said humanized antibodies or antibody fragments. In another embodiment, a combination of humanized antibodies, a combination of antibody fragments, or a combination of humanized antibodies and antibody fragments prevent flaviviral from binding to its host cell receptor by at least 99%, at least 95%, at least 90%, at least 85%, at least 80%, at least 75%, at least 70%, at least 60%, at least 50%, at least 45%, at least 40%, at least 45%, at least 35%, at least 30%, at least 25%, at least 20%, or at least 10% relative to WNV binding to its host cell receptor in the absence of said antibodies and/or antibody fragments.

One or more humanized antibodies of the present invention or fragments thereof that immunospecifically bind to one or more flaviviral antigens, particularly a WNV antigen, may be used locally or systemically in the body as a therapeutic. The humanized antibodies of this invention or fragments thereof may also be advantageously utilized in combination with other monoclonal or chimeric antibodies, or with lymphokines or hematopoietic growth factors (such as, e.g., IL-2, IL-3 and IL-7), which, for example, serve to increase the number or activity of effector cells which interact with the antibodies or serve to increase the immune response. The humanized antibodies of this invention or fragments thereof may also be advantageously utilized in combination with one or more drugs used to treat flaviviral infections, particularly WNV infections, such as, for example anti-viral agents. Examples of anti-viral agents include, but are not limited to, protease inhibitors, nucleoside reverse transcriptase inhibitors, non-nucleoside reverse transcriptase inhibitors and nucleoside analogs, zidovudine, acyclovir, gangcyclovir, vidarabine, idoxuridine, trifluridine, and ribavirin, as well as foscarnet, amantadine, rimantadine, saquinavir, indinavir, amprenavir, lopinavir, ritonavir, the alpha-interferons; adefovir, clevadine, entecavir, and pleconaril. The invention encompasses any other anti-viral agent being developed and known to those skilled in the art.

The humanized antibodies of the invention may be administered alone or in combination with other types of treatments (e.g., hormonal therapy, immunotherapy, and anti-inflammatory agents). Generally, administration of products of a species origin or species reactivity (in the case of antibodies) that is the same species as that of the patient is preferred. Thus, in a preferred embodiment, human or humanized antibodies, fragments derivatives, analogs, or nucleic acids, are administered to a human patient for therapy or prophylaxis.

It is preferred to use high affinity and/or potent in vivo inhibiting antibodies and/or neutralizing antibodies that immunospecifically bind to a flaviviral antigen, particularly WNV antigen, for prevention of flaviviral infection, particularly WNV infection and therapy for flaviviral infection, particularly WNV infection. It is also preferred to use polynucleotides encoding high affinity and/or potent in vivo inhibiting antibodies and/or neutralizing antibodies that immunospecifically bind to a flaviviral antigen, particularly WNV antigen, for both immunoassays directed to WNV and therapy for WNV infection. Such antibodies or fragments thereof will preferably have an affinity for the WNV E protein. In a specific embodiment, a mammal, preferably a human, is administered a therapeutic or pharmaceutical composition comprising one or more humanized antibodies of the present invention or fragments thereof for the treatment, prevention or amelioration of one or more symptoms associated with a flavirial infection, particularly WNF infection.

Prophylactic and therapeutic compounds that may be used in combination with the humanized antibodies of the invention include, but are not limited to, proteinaceous molecules, including, but not limited to, peptides, polypeptides, proteins, including post-translationally modified proteins, antibodies, etc.; small molecules (less than 1000 daltons), inorganic or organic compounds; nucleic acid molecules including, but not limited to, double-stranded or single-stranded DNA, double-stranded or single-stranded RNA, as well as triple helix nucleic acid molecules. Prophylactic and therapeutic compounds can be derived from any known organism (including, but not limited to, animals, plants, bacteria, fungi, and protista, or viruses) or from a library of synthetic molecules.

In certain embodiments, one or more humanized antibodies of the invention are administered to a mammal, preferably, a human, concurrently with one or more other therapeutic agents, e.g., anti-viral agents, useful for the treatment or prevention of a flaviviral infection, particularly, a WNV infection. The term "concurrently" is not limited to the administration of prophylactic or therapeutic agents at exactly the same time, but rather it is meant that humanized antibodies of the invention and the other agent are administered to a subject in a sequence and within a time interval such that the humanized antibodies of the invention can act together with the other agent to provide an increased benefit than if they were administered otherwise. For example, each prophylactic or therapeutic agent may be administered at the same time or sequentially in any order at different points in time; however, if not administered at the same time, they should be administered sufficiently close in time so as to provide the desired therapeutic or prophylactic effect. Each therapeutic agent can be administered separately, in any appropriate form and by any suitable route.

In various embodiments, the prophylactic or therapeutic agents are administered less than 1 hour apart, at about 1 hour apart, at about 1 hour to about 2 hours apart, at about 2 hours to about 3 hours apart, at about 3 hours to about 4 hours apart, at about 4 hours to about 5 hours apart, at about 5 hours to about 6 hours apart, at about 6 hours to about 7 hours apart, at about 7 hours to about 8 hours apart, at about 8 hours to about 9 hours apart, at about 9 hours to about 10 hours apart, at about 10 hours to about 11 hours apart, at about 111 hours to about 12 hours apart, no more than 24 hours apart or no more than 48 hours apart. In preferred embodiments, two or more components are administered within the same patient visit.

The dosage amounts and frequencies of administration provided herein are encompassed by the terms therapeutically effective and prophylactically effective. The dosage and frequency further will typically vary according to factors specific for each patient depending on the specific therapeutic or prophylactic agents administered, the severity and type of cancer, the route of administration, as well as age, body weight, response, and the past medical history of the patient. Suitable regimens can be selected by one skilled in the art by considering such factors and by following, for example, dosages reported in the literature and recommended in the *Physician's Desk Reference* (56th ed., 2002).

5.5 Compositions and Methods of Administering

The invention provides methods of treatment, prophylaxis, and amelioration of one or more symptoms associated with flaviviral infection, particularly WNV infection, by administrating to a subject of an effective amount of a humanized antibody of the invention or fragment thereof, or pharmaceutical composition comprising a humanized antibody of the invention or fragment thereof. In a preferred aspect, an antibody or fragment thereof is substantially purified (i.e., substantially free from substances that limit its effect or produce undesired side-effects). The subject is preferably a mammal such as non-primate (e.g., cows, pigs, horses, cats, dogs, rats etc.) and a primate (e.g., monkey such as a cynomolgous monkey and a human). In a preferred embodiment, the subject is a human, particularly a human who is at an increased risk of flaviviral infection, particularly WNV infection. In another preferred embodiment, the subject is a human infant, an elderly human, or a human with an impaired immune system.

Various delivery systems are known and can be used to administer a composition comprising humanized antibodies of the invention, e.g., encapsulation in liposomes, microparticles, microcapsules, recombinant cells capable of expressing the antibody or fusion protein, receptor-mediated endocytosis (see, e.g., Wu and Wu, 1987, *J. Biol. Chem.* 262:4429-4432), construction of a nucleic acid as part of a retroviral or other vector, etc.

In some embodiments, the humanized antibodies of the invention are formulated in liposomes for targeted delivery of the humanized antibodies of the invention. Liposomes are vesicles comprised of concentrically ordered phopsholipid bilayers which encapsulate an aqueous phase. Liposomes typically comprise various types of lipids, phospholipids, and/or surfactants. The components of liposomes are arranged in a bilayer configuration, similar to the lipid arrangement of biological membranes. Liposomes are particularly preferred delivery vehicles due, in part, to their biocompatibility, low immunogenicity, and low toxicity. Methods for preparation of liposomes are known in the art and are encompassed within the invention, see, e.g., Epstein et al., 1985, *Proc. Natl. Acad. Sci. USA,* 82: 3688; Hwang et al., 1980 *Proc. Natl. Acad. Sci. USA,* 77: 4030-4; U.S. Pat. Nos. 4,485,045 and 4,544,545; all of which are incorporated herein by reference in their entirety.

The invention also encompasses methods of preparing liposomes with a prolonged serum half-life, i.e., enhanced circulation time, such as those disclosed in U.S. Pat. No. 5,013,556. Preferred liposomes used in the methods of the invention are not rapidly cleared from circulation, i.e., are not taken up into the mononuclear phagocyte system (MPS). The invention encompasses sterically stabilized liposomes which are prepared using common methods known to one skilled in the art. Although not intending to be bound by a particular mechanism of action, sterically stabilized liposomes contain lipid components with bulky and highly flexible hydrophilic moieties, which reduces the unwanted reaction of liposomes with serum proteins, reduces oposonization with serum components and reduces recognition by MPS. Sterically stabilized liposomes are preferably prepared using polyethylene glycol. For preparation of liposomes and sterically stabilized liposome, see, e.g., Bendas et al., 2001 *BioDrugs,* 15(4): 215-224; Allen et al., 1987 *FEBS Lett.* 223: 42-6; Klibanov et al., 1990 *FEBS Lett.,* 268: 235-7; Blum et al., 1990, *Biochim. Biophys. Acta.,* 1029: 91-7; Torchilin et al., 1996, *J. Liposome Res.* 6: 99-116; Litzinger et al., 1994, *Biochim. Biophys. Acta,* 1190: 99-107; Maruyama et al., 1991, *Chem. Pharm. Bull.,* 39: 1620-2; Klibanov et al., 1991, *Biochim Biophys Acta,* 1062; 142-8; Allen et al., 1994, *Adv. Drug Deliv. Rev,* 13: 285-309; all of which are incorporated herein by reference in their entirety. The invention also encompasses liposomes that are adapted for specific organ targeting, see, e.g., U.S. Pat. No. 4,544,545. Particularly useful liposomes for use in the compositions and methods of the invention can be generated by reverse phase evaporation method with a lipid composition comprising phosphatidylcholine, cholesterol, and PEG derivatized phosphatidylethanolamine (PEG-PE). Liposomes are extruded through filters of defined pore size to yield liposomes with the desired diameter. In some embodiments, a fragment of a humanized antibody of the invention, e.g., F(ab'), may be conjugated to the liposomes using previously described methods, see, e.g., Martin et al., 1982, J. Biol. Chem. 257: 286-288, which is incorporated herein by reference in its entirety.

The humanized antibodies of the invention may also be formulated as immunoliposomes. Immunoliposomes refer to a liposomal composition, wherein a humanized antibody of the invention or a fragment thereof is linked, covalently or non-covalently to the liposomal surface. The chemistry of linking an antibody to the liposomal surface is known in the art and encompassed within the invention, see, e.g., Allen et al., 1995, Stealth Liposomes, Boca Raton: CRC Press, 233-44; Hansen et al., 1995, *Biochim. Biophys. Acta,* 1239: 133-44; which are incorporated herein by reference in their entirety. In most preferred embodiments, immunoliposomes for use in the methods and compositions of the invention are further sterically stabilized. Preferably, the humanized antibodies of the invention are linked covalently or non-covalently to a hydrophobic anchor, which is stably rooted in the lipid bilayer of the liposome. Examples of hydrophobic anchors include, but are not limited to, phospholipids, e.g., phosoatidylethanolamine (PE), phospahtidylinositol (PI). To achieve a covalent linkage between an antibody and a hydrophobic anchor, any of the known biochemical strategies in the art may be used, see, e.g., J. Thomas August, ed., 1997, Gene Therapy: Advances in Pharmacology, Volume 40, Academic Press, San Diego, Calif., p. 399-435, which is incorporated herein by reference in its entirety. For example, a functional group on an antibody molecule may react with an active group on a liposome associated hydrophobic anchor, e.g., an amino group of a lysine side chain on an antibody may be coupled to liposome associated N-glutaryl-phosphatidylethanolamine activated with water-soluble carbodiimide; or a thiol group of a reduced antibody can be coupled to liposomes via thiol reactive anchors, such as pyridylthiopropionyl-phosphatidylethanolamine. See, e.g., Dietrich et al., 1996, Biochemistry, 35: 1100-1105; Loughrey et al., 1987, *Biochim. Biophys. Acta,* 901: 157-160; Martin et al., 1982, *J. Biol. Chem.* 257: 286-288; Martin et al., 1981, *Biochemistry,* 20: 4429-38; all of which are incorporated herein by reference in their entirety.

The invention encompasses immunoliposomes comprising a humanized antibody of the invention or a fragment thereof. In some embodiments, the immunoliposomes further comprise one or more additional therapeutic agents, such as those disclosed herein.

The immunoliposomal compositions of the invention comprise one or more vesicle forming lipids, a humanized antibody of the invention or a fragment or derivative thereof, and, optionally, a hydrophilic polymer. A vesicle forming lipid is preferably a lipid with two hydrocarbon chains, such as acyl chains and a polar head group. Examples of vesicle forming lipids include phospholipids, e.g., phosphatidylcholine, phosphatidylethanolamine, phosphatidic acid, phosphatidylinositol, sphingomyelin, and glycolipids, e.g., cerebrosides, gangliosides. Additional lipids useful in the formulations of the invention are known to one skilled in the art and encompassed within the invention. In some embodiments, the immunoliposomal compositions further comprise a hydrophilic polymer, e.g., polyethylene glycol, and gnaglioside GM 1, which increases the serum half life of the liposome. Methods of conjugating hydrophilic polymers to liposomes are well known in the art and encompassed within the invention. For a review of immunoliposomes and methods of preparing them, see, e.g., PCT International Publication No. WO 97/38731, Vingerhoeads et al., 1994, *Immunomethods,* 4: 259-72; Maruyama, 2000, *Biol. Pharm. Bull.* 23(7): 791-799; Abra et al., 2002, *Journal of Liposome Research,* 12(1&2): 1-3; Park, 2002, *Bioscience Reports,* 22(2): 267-281; Bendas et al., 2001 *BioDrugs,* 14(4): 215-224, J. Thomas August, ed., 1997, Gene Therapy: Advances in Pharmacology, Volume 40, Academic Press, San Diego, Calif., p. 399-435, all of which are incorporated herein by reference in their entireties.

Methods of administering the humanized antibodies of the invention include, but are not limited to, parenteral administration (e.g., intradermal, intramuscular, intraperitoneal, intravenous and subcutaneous), epidural, and mucosal (e.g., intranasal and oral routes). In a specific embodiment, the humanized antibodies of the invention are administered intramuscularly, intravenously, or subcutaneously. The compositions may be administered by any convenient route, for example, by infusion or bolus injection, by absorption through epithelial or mucocutaneous linings (e.g., oral mucosa, rectal and intestinal mucosa, etc.) and may be administered together with other biologically active agents. Administration can be systemic or local. In addition, pulmonary administration can also be employed, e.g., by use of an inhaler or nebulizer, and formulation with an aerosolizing agent. See, e.g., U.S. Pat. Nos. 6,019,968; 5,985,20; 5,985,309; 5,934,272; 5,874,064; 5,855,913; 5,290,540; and 4,880,078; and PCT Publication Nos. WO 92/19244; WO 97/32572; WO 97/44013; WO 98/31346; and WO 99/66903, each of which is incorporated herein by reference in its entirety.

The invention also provides that the humanized antibodies of the invention are packaged in a hermetically sealed container, such as an ampoule or sachette, indicating the quantity of antibody. In one embodiment, the humanized antibodies of the invention are supplied as a dry sterilized lyophilized powder or water free concentrate in a hermetically sealed container and can be reconstituted, e.g., with water or saline to the appropriate concentration for administration to a subject. Preferably, the humanized antibodies of the invention are supplied as a dry sterile lyophilized powder in a hermetically sealed container at a unit dosage of at least 5 mg, more preferably at least 10 mg, at least 15 mg, at least 25 mg, at least 35 mg, at least 45 mg, at least 50 mg, or at least 75 mg. The lyophilized humanized antibodies of the invention should be stored at between 2 and 8° C. in their original container and the humanized antibodies should be administered within 12 hours, preferably within 6 hours, within 5 hours, within 3 hours, or within 1 hour after being reconstituted. In an alternative embodiment, humanized antibodies of the invention are supplied in liquid form in a hermetically sealed container indicating the quantity and concentration of the antibody, fusion protein, or conjugated molecule. Preferably, the liquid form of the humanized antibodies are supplied in a hermetically sealed container at least 1 mg/ml, more preferably at least 2.5 mg/ml, at least 5 mg/ml, at least 8 mg/ml, at least 10 mg/ml, at least 15 mg/kg, at least 25 mg/ml, at least 50 mg/ml, at least 100 mg/ril, at least 150 mg/ml, at least 200 mg/ml of the humanized antibodies.

The amount of the composition of the invention which will be effective in the treatment, prevention or amelioration of one or more symptoms associated with a flaviviral infection, particularly, a WNV infection, can be determined by standard clinical techniques. The precise dose to be employed in the formulation will also depend on the route of administration, and the seriousness of the condition, and should be decided according to the judgment of the practitioner and each patient's circumstances. Effective doses may be extrapolated from dose-response curves derived from in vitro or animal model test systems.

For humanized antibodies encompassed by the invention, the dosage administered to a patient is typically 0.0001 mg/kg to 100 mg/kg of the patient's body weight. Preferably, the dosage administered to a patient is between 0.0001 mg/kg and 20 mg/kg, 0.0001 mg/kg and 10 mg/kg, 0.0001 mg/kg and 5 mg/kg, 0.0001 and 2 mg/kg, 0.0001 and 1 mg/kg, 0.0001 mg/kg and 0.75 mg/kg, 0.0001 mg/kg and 0.5 mg/kg, 0.0001 mg/kg to 0.25 mg/kg, 0.0001 to 0.15 mg/kg, 0.0001 to 0.10 mg/kg, 0.001 to 0.5 mg/kg, 0.01 to 0.25 mg/kg or 0.01 to 0.10 mg/kg of the patient's body weight. In one embodiment, the dosage of the humanized antibodies of the invention administered to a patient are 0.01 mg to 1000 mg/day, when used as single agent therapy. In other embodiments, the therapeutically or prophylactically effective dosage administered to a subject is typically 0.1 mg/kg to 200 mg/kg of the subject's body weight. Preferably, the dosage administered to a subject is between 0.1 mg/kg and 20 mg/kg of the subject's body weight and more preferably the dosage administered to a subject is between 1 mg/kg to 10 mg/kg of the subject's body weight. Generally, human antibodies have a longer half-life within the human body than antibodies from other species due to the immune response to the foreign polypeptides. Thus, lower dosages of human antibodies and less frequent administration is often possible. Further, the dosage and frequency of administration of humanized antibodies of the invention or fragments thereof may be reduced by enhancing uptake and tissue penetration of the antibodies by modifications such as, for example, lipidation.

In another embodiment the antibodies of the invention are used in combination with other therapeutic compositions and the dosage administered to a patient are lower than when said humanized antibodies are used as a single agent therapy.

In a specific embodiment, it may be desirable to administer the pharmaceutical compositions of the invention locally to the area in need of treatment; this may be achieved by, for example, and not by way of limitation, local infusion, by injection, or by means of an implant, said implant being of a porous, non-porous, or gelatinous material, including membranes, such as sialastic membranes, or fibers. Preferably, when administering a humanized antibody of the invention, care must be taken to use materials to which the antibody or the fusion protein does not absorb.

In another embodiment, the compositions can be delivered in a vesicle, in particular a liposome (See Langer, *Science* 249:1527-1533 (1990); Treat et al., in Liposomes in the Therapy of Infectious Disease and Cancer, Lopez-Berestein and Fidler (eds.), Liss, New York, pp. 353-365 (1989); Lopez-Berestein, ibid., pp. 317-327; see generally ibid.).

In yet another embodiment, the compositions can be delivered in a controlled release or sustained release system. Any technique known to one of skill in the art can be used to produce sustained release formulations comprising one or more humanized antibodies of the invention. See, e.g., U.S. Pat. No. 4,526,938; PCT publication WO 91/05548; PCT publication WO 96/20698; Ning et al., 1996, "Intratumoral Radioimmunotherapy of a Human Colon Cancer Xenograft Using a Sustained-Release Gel," *Radiotherapy & Oncology* 39:179-189, Song et al., 1995, "Antibody Mediated Lung Targeting of Long-Circulating Emulsions," *PDA Journal of Pharmaceutical Science & Technology* 50:372-397; Cleek et al., 1997, "Biodegradable Polymeric Carriers for a bFGF Antibody for Cardiovascular Application," *Pro. Int'l. Symp. Control. Rel. Bioact. Mater.* 24:853-854; and Lam et al., 1997, "Microencapsulation of Recombinant Humanized Monoclonal Antibody for Local Delivery," Proc. *Int'l. Symp. Control Rel. Bioact. Mater.* 24:759-760, each of which is incorporated herein by reference in its entirety. In one embodiment, a pump may be used in a controlled release system (See Langer, supra; Sefton, 1987, *CRC Crit. Ref. Biomed. Eng.* 14:20; Buchwald et al., 1980, Surgery 88:507; and Saudek et al., 1989, *N. Engl. J. Med.* 321:574). In another embodiment, polymeric materials can be used to achieve controlled release of antibodies (see e.g., Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger and Peppas, 1983, J., *Macromol. Sci. Rev. Macromol. Chem.* 23:61; See also Levy et al., 1985, *Science* 228:190; During et al., 1989, Ann. Neurol. 25:351; Howard et al., 1989, *J. Neurosurg.* 71:105); U.S. Pat. No. 5,679,377; U.S. Pat. No. 5,916,597; U.S. Pat. No. 5,912,015; U.S. Pat. No. 5,989,463; U.S. Pat. No. 5,128,326; PCT Publication No. WO 99/15154; and PCT Publication No. WO 99/20253). Examples of polymers used in sustained release formulations include, but are not limited to, poly(2-hydroxy ethyl methacrylate), poly(methyl methacrylate), poly(acrylic acid), poly(ethylene-co-vinyl acetate), poly (methacrylic acid), polyglycolides (PLG), polyanhydrides, poly(N-vinyl pyrrolidone), poly(vinyl alcohol), polyacrylamide, poly(ethylene glycol), polylactides (PLA), poly(lactide-co-glycolides) (PLGA), and polyorthoesters. In yet another embodiment, a controlled release system can be placed in proximity of the therapeutic target (e.g., the lungs), thus requiring only a fraction of the systemic dose (see, e.g., Goodson, in Medical Applications of Controlled Release, supra, vol. 2, pp. 115-138 (1984)). In another embodiment, polymeric compositions useful as controlled release implants are used according to Dunn et al. (See U.S. Pat. No. 5,945, 155). This particular method is based upon the therapeutic effect of the in situ controlled release of the bioactive material from the polymer system. The implantation can generally occur anywhere within the body of the patient in need of therapeutic treatment. In another embodiment, a non-polymeric sustained delivery system is used, whereby a non-polymeric implant in the body of the subject is used as a drug delivery system. Upon implantation in the body, the organic solvent of the implant will dissipate, disperse, or leach from the composition into surrounding tissue fluid, and the non-polymeric material will gradually coagulate or precipitate to form a solid, microporous matrix (See U.S. Pat. No. 5,888, 533).

Controlled release systems are discussed in the review by Langer (1990, *Science* 249:1527-1533). Any technique known to one of skill in the art can be used to produce sustained release formulations comprising one or more therapeutic agents of the invention. See, e.g., U.S. Pat. No. 4,526, 938; International Publication Nos. WO 91/05548 and WO 96/20698; Ning et al., 1996, *Radiotherapy & Oncology* 39:179-189; Song et al., 1995, *PDA Journal of Pharmaceutical Science & Technology* 50:372-397; Cleek et al., 1997, *Pro. Int'l. Symp. Control. Rel. Bioact. Mater.* 24:853-854; and Lam et al., 1997, *Proc. Int'l. Symp. Control Rel. Bioact. Mater.* 24:759-760, each of which is incorporated herein by reference in its entirety.

In a specific embodiment where the composition of the invention is a nucleic acid encoding an antibody, the nucleic acid can be administered in vivo to promote expression of its encoded humanized antibody, by constructing it as part of an appropriate nucleic acid expression vector and administering it so that it becomes intracellular, e.g., by use of a retroviral vector (See U.S. Pat. No. 4,980,286), or by direct injection, or by use of microparticle bombardment (e.g., a gene gun; Biolistic, Dupont), or coating with lipids or cell-surface receptors or transfecting agents, or by administering it in linkage to a homeobox-like peptide which is known to enter the nucleus (See e.g., Joliot et al., 1991, *Proc. Natl. Acad. Sci. USA* 88:1864-1868), etc. Alternatively, a nucleic acid can be introduced intracellularly and incorporated within host cell DNA for expression by homologous recombination.

Treatment of a subject with a therapeutically or prophylactically effective amount of humanized antibodies of the invention can include a single treatment or, preferably, can include a series of treatments. In a preferred example, a subject is treated with humanized antibodies of the invention in the range of between about 0.1 to 30 mg/kg body weight, one time per week for between about 1 to 10 weeks, preferably between 2 to 8 weeks, more preferably between about 3 to 7 weeks, and even more preferably for about 4, 5, or 6 weeks. In other embodiments, the pharmaceutical compositions of the invention are administered once a day, twice a day, or three times a day. In other embodiments, the pharmaceutical compositions are administered once a week, twice a week, once every two weeks, once a month, once every six weeks, once every two months, twice a year or once per year. It will also be appreciated that the effective dosage of the humanized antibodies used for treatment may increase or decrease over the course of a particular treatment.

5.5.1 Pharmaceutical Compositions

The compositions of the invention include bulk drug compositions useful in the manufacture of pharmaceutical compositions (e.g., impure or non-sterile compositions) and pharmaceutical compositions (i.e., compositions that are suitable for administration to a subject or patient) which can be used in the preparation of unit dosage forms. Such compositions comprise a prophylactically or therapeutically effective amount of a prophylactic and/or therapeutic agent disclosed herein or a combination of those agents and a pharmaceutically acceptable carrier. Preferably, compositions of the invention comprise a prophylactically or therapeutically effective amount of humanized antibodies of the invention and a pharmaceutically acceptable carrier.

In one particular embodiment, the pharmaceutical composition comprises of a therapeutically effective amount of a humanized antibody, or a fragment thereof, that binds one or more flaviviral antigens, particularly WNV antigens, and a pharmaceutically acceptable carrier. In another embodiment, said pharmaceutical composition further comprises one or more additional prophylactic or therapeutic agents.

In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant (e.g., Freund's adjuvant (complete and incomplete)), excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like.

Generally, the ingredients of compositions of the invention are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The compositions of the invention can be formulated as neutral or salt forms. Pharmaceutically acceptable salts include, but are not limited to, those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

5.6 Characterization and Demonstration of Therapeutic Utility

Humanized antibodies of the present invention or fragments thereof may be characterized in a variety of ways. In particular, humanized antibodies of the invention or fragments thereof may be assayed for the ability to immunospecifically bind to a WNV antigen. Such an assay may be performed in solution (e.g., Houghten, 1992, Bio/Techniques 13:412-421), on beads (Lam, 1991, Nature 354:82-84), on chips (Fodor, 1993, Nature 364:555-556), on bacteria (U.S. Pat. No. 5,223,409), on spores (U.S. Pat. Nos. 5,571,698; 5,403,484; and 5,223,409), on plasmids (Cull et al., 1992, Proc. Natl. Acad. Sci. USA 89:1865-1869) or on phage (Scott and Smith, 1990, Science 249:386-390; Devlin, 1990, Science 249:404-406; Cwirla et al., 1990, Proc. Natl. Acad. Sci. USA 87:6378-6382; and Felici, 1991, J. Mol. Biol. 222:301-310) (each of these references is incorporated herein in its entirety by reference). Humanized antibodies or fragments thereof that have been identified to immunospecifically bind to a flaviviral antigen or a fragment thereof can then be assayed for their specificity and affinity for a flaviviral antigen.

The humanized antibodies of the invention or fragments thereof may be assayed for immunospecific binding to a flaviviral antigen, particularly WNV antigen and cross-reactivity with other antigens by any method known in the art. Immunoassays which can be used to analyze immunospecific binding and cross-reactivity include, but are not limited to, competitive and non-competitive assay systems using techniques such as western blots, radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, protein A immunoassays, to name but a few. Such assays are routine and well known in the art (see, e.g., Ausubel et al, eds, 1994, Current Protocols in Molecular Biology, Vol. 1, John Wiley & Sons, Inc., New York, which is incorporated by reference herein in its entirety). Exemplary immunoassays are described briefly below (but are not intended by way of limitation).

Immunoprecipitation protocols generally comprise lysing a population of cells in a lysis buffer such as RIPA buffer (1% NP-40 or Triton X-100, 1% sodium deoxycholate, 0.1% SDS, 0.15 M NaCl, 0.01 M sodium phosphate at pH 7.2, 1% Trasylol) supplemented with protein phosphatase and/or protease inhibitors (e.g., EDTA, PMSF, aprotinin, sodium vanadate), adding the antibody of interest to the cell lysate, incubating for a period of time (e.g., 1 to 4 hours) at 40° C., adding protein A and/or protein G sepharose beads to the cell lysate, incubating for about an hour or more at 40° C., washing the beads in lysis buffer and resuspending the beads in SDS/sample buffer. The ability of the antibody of interest to immunoprecipitate a particular antigen can be assessed by, e.g., western blot analysis. One of skill in the art would be knowledgeable as to the parameters that can be modified to increase the binding of the antibody to an antigen and decrease the background (e.g., pre-clearing the cell lysate with sepharose beads). For further discussion regarding immunoprecipitation protocols see, e.g., Ausubel et al, eds, 1994, Current Protocols in Molecular Biology, Vol. 1, John Wiley & Sons, Inc., New York at 10.16.1.

Western blot analysis generally comprises preparing protein samples, electrophoresis of the protein samples in a polyacrylamide gel (e.g., 8%-20% SDS-PAGE depending on the molecular weight of the antigen), transferring the protein sample from the polyacrylamide gel to a membrane such as nitrocellulose, PVDF or nylon, blocking the membrane in blocking solution (e.g., PBS with 3% BSA or non-fat milk), washing the membrane in washing buffer (e.g., PBS-Tween 20), blocking the membrane with primary antibody (the antibody of interest) diluted in blocking buffer, washing the membrane in washing buffer, blocking the membrane with a secondary antibody (which recognizes the primary antibody, e.g., an anti-human antibody) conjugated to an enzymatic substrate (e.g., horseradish peroxidase or alkaline phosphatase) or radioactive molecule (e.g., $^{32}P$ or $^{125}I$) diluted in blocking buffer, washing the membrane in wash buffer, and detecting the presence of the antigen. One of skill in the art would be knowledgeable as to the parameters that can be modified to increase the signal detected and to reduce the background noise. For further discussion regarding western blot protocols see, e.g., Ausubel et al, eds, 1994, Current Protocols in Molecular Biology, Vol. 1, John Wiley & Sons, Inc., New York at 10.8.1.

ELISAs comprise preparing antigen, coating the well of a 96 well microtiter plate with the antigen, adding the antibody of interest conjugated to a detectable compound such as an enzymatic substrate (e.g., horseradish peroxidase or alkaline phosphatase) to the well and incubating for a period of time, and detecting the presence of the antigen. In ELISAs the antibody of interest does not have to be conjugated to a detectable compound; instead, a second antibody (which recognizes the antibody of interest) conjugated to a detectable compound may be added to the well. Further, instead of coating the well with the antigen, the antibody may be coated to the well. In this case, a second antibody conjugated to a detectable compound may be added following the addition of the antigen of interest to the coated well. One of skill in the art would be knowledgeable as to the parameters that can be modified to increase the signal detected as well as other variations of ELISAs known in the art. For further discussion regarding ELISAs see, e.g., Ausubel et al,. eds, 1994, Current Protocols in Molecular Biology, Vol. 1, John Wiley & Sons, Inc., New York at 11.2.1.

The binding affinity of an antibody to an antigen and the off-rate of an antibody-antigen interaction can be determined by competitive binding assays. One example of a competitive binding assay is a radioimmunoassay comprising the incubation of labeled antigen (e.g., $^{3}H$ or $^{125}I$) with the antibody of interest in the presence of increasing amounts of unlabeled antigen, and the detection of the antibody bound to the labeled antigen. The affinity of the humanized antibodies of the present invention or fragments thereof for a WNV antigen and the binding off-rates can be determined from the data by scatchard plot analysis. Competition with a second antibody can also be determined using radioimmunoassays. In this case, a WNV antigen is incubated with a humanized antibody of the present invention or a fragment thereof conjugated to a labeled compound (e.g., $^{3}H$ or $^{125}I$) in the presence of increasing amounts of an unlabeled second antibody.

In a preferred embodiment, BIAcore kinetic analysis is used to determine the binding on and off rates of humanized antibodies or fragments thereof to a WNV antigen. BIAcore kinetic analysis comprises analyzing the binding and dissociation of a WNV antigen from chips with immobilized humanized antibodies or fragments thereof on their surface.

The humanized antibodies of the invention or fragments thereof can also be assayed for their ability to inhibit the binding of a flaviviral antigen to its host cell receptor using techniques known to those of skill in the art and exemplified herein. For example, cells expressing the receptor for WNV can be contacted with WNV in the presence or absence of an antibody or fragment thereof and the ability of the antibody or fragment thereof to inhibit WNV's binding can measured by, for example, flow cytometry or a scintillation assay. WNV (e.g., WNV antigen such as E protein) or the antibody or antibody fragment can be labeled with a detectable compound such as a radioactive label (e.g., $^{32}P$, $^{35}S$, and $^{125}I$) or a fluorescent label (e.g., fluorescein isothiocyanate, rhodamine, phycoerythrin, phycocyanin, allophycocyanin, o-phthaldehyde and fluorescamine) to enable detection of an interaction between WNV and its host cell receptor. Alternatively, the ability of humanized antibodies or fragments thereof to inhibit WNV from binding to its receptor can be determined in cell-free assays. For example, WNV or a WNV antigen can be contacted with an antibody or fragment thereof and the ability of the antibody or antibody fragment to inhibit WNV or the WNV antigen from binding to its host cell receptor can be determined. Preferably, the antibody or the antibody fragment is immobilized on a solid support and WNV or a WNV antigen is labeled with a detectable compound. Alternatively, WNV or a WNV antigen is immobilized on a solid support and the antibody or fragment thereof is labeled with a detectable compound. WNV or a WNV antigen may be partially or completely purified (e.g., partially or completely free of other polypeptides) or part of a cell lysate. Further, an WNV antigen may be a fusion protein comprising the WNV antigen and a domain such as glutathionine-S-transferase. Alternatively, an WNV antigen can be biotinylated using techniques well known to those of skill in the art (e.g., biotinylation kit, Pierce Chemicals; Rockford, Ill.).

Several aspects of the pharmaceutical compositions or prophylactic or therapeutic agents of the invention are preferably tested in vitro, e.g., in a cell culture system, and then in vivo, e.g., in an animal model organism, such as a rodent animal model system, for the desired therapeutic or prophylatic activity, prior to use in humans. For example, in vitro assays which can be used to determine whether administration of a specific pharmaceutical composition is indicated, include cell culture assays in which a patient tissue sample is grown in culture, and exposed to or otherwise contacted with a pharmaceutical composition, and the effect of such composition upon the tissue sample is observed. In various specific embodiments, in vitro assays can be carried out with representative cells of cell types involved in a WNV infection to determine if a pharmaceutical composition of the invention has a desired effect upon such cell types. Preferably, the humanized antibodies or compositions of the invention are also tested in in vitro assays and animal model systems prior to administration to humans. In a specific embodiment, mice are administered a humanized antibody the invention or fragment thereof, or a composition of the invention, challenged with 100 to 1000 pfu of WNV, and four or more days later the mice are sacrificed and WNV titer and anti-WNV antibody serum titer is determined.

Efficacy in treating or preventing viral infection may be demonstrated by detecting the ability of a humanized antibody or composition of the invention to inhibit the replication of the virus, to inhibit transmission or prevent the virus from establishing itself in its host, to reduce the incidence of WNV nfection, or to prevent, ameliorate or alleviate one or more symptoms associated with WNV infection. The treatment is considered therapeutic if there is, for example, a reduction is viral load, amelioration of one or more symptoms, a reduction in the duration of a WNV infection, or a decrease in mortality and/or morbidity following administration of a humanized antibody or composition of the invention. Further, the treatment is considered therapeutic if there is an increase in the immune response following the administration of one or more humanized antibodies or fragments thereof which immunospecifically bind to one or more WNV antigens.

Humanized antibodies or compositions of the invention can be tested in vitro and in vivo for the ability to induce the expression of cytokines such as IFN-α, IFN-β, IFN-γ, IL-2, IL-3, IL-4, IL-5, IL-6, IL-7, IL-8, IL-9, IL-10, IL-12 and IL-15. Techniques known to those of skill in the art can be used to measure the level of expression of cytokines. For example, the level of expression of cytokines can be measured by analyzing the level of RNA of cytokines by, for example, RT-PCR and Northern blot analysis, and by analyzing the level of cytokines by, for example, immunoprecipitation followed by western blot analysis and ELISA.

Humanized antibodies or compositions of the invention can be tested in vitro and in vivo for their ability to modulate the biological activity of immune cells, preferably human immune cells (e.g., T-cells, B-cells, and Natural Killer cells). The ability of a humanized antibody or composition of the invention to modulate the biological activity of immune cells can be assessed by detecting the expression of antigens, detecting the proliferation of immune cells, detecting the activation of signaling molecules, detecting the effector function of immune cells, or detecting the differentiation of immune cells. Techniques known to those of skill in the art can be used for measuring these activities. For example, cellular proliferation can be assayed by $^3$H-thymidine incorporation assays and trypan blue cell counts. Antigen expression can be assayed, for example, by immunoassays including, but are not limited to, competitive and non-competitive assay systems using techniques such as western blots, immunohistochemistry radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, protein A immunoassays and FACS analysis. The activation of signaling molecules can be assayed, for example, by kinase assays and electrophoretic shift assays (EMSAs).

Humanized antibodies or compositions of the invention can also be tested for their ability to inhibit viral replication or reduce viral load in in vitro, ex vivo and in vivo assays. Humanized antibodies or compositions of the invention can also be tested for their ability to decrease the time course of WNV infection. Humanized antibodies or compositions of the invention can also be tested for their ability to increase the survival period of humans suffering from WNV infection by at least 25%, preferably at least 50%, at least 60%, at least 75%, at least 85%, at least 95%, or at least 99%. Further, humanized antibodies or compositions of the invention can be tested for their ability reduce the hospitalization period of humans suffering from WNV infection by at least 60%, preferably at least 75%, at least 85%, at least 95%, or at least 99%. Techniques known to those of skill in the art can be used to analyze the function of the humanized antibodies or compositions of the invention in vivo.

Compounds for use in therapy can be tested in suitable animal model systems prior to testing in humans, including, but not limited to, in rats, mice, chicken, cows, monkeys, pigs, dogs, rabbits, hamsters, etc., for example, the animal models described above. Any animal system well-known in the art may be used.

Combinations of prophylactic and/or therapeutic agents can be tested in suitable animal model systems prior to use in humans. In a specific embodiment of the invention, combinations of prophylactic and/or therapeutic agents are tested in a mouse model system. Such model systems are widely used and well-known to the skilled artisan. Prophylactic and/or therapeutic agents can be administered repeatedly. Several aspects of the procedure may vary such as the temporal regime of administering the prophylactic and/or therapeutic agents, and whether such agents are administered separately or as an admixture.

Once the prophylactic and/or therapeutic agents of the invention have been tested in an animal model they can be tested in clinical trials to establish their efficacy. Establishing clinical trials will be done in accordance with common methodologies known to one skilled in the art, and the optimal dosages and routes of administration as well as toxicity profiles of the compositions of the invention can be established using routine experimentation.

The data obtained from the cell culture assays and animal studies can be used in formulating a range of dosage of the prophylactic and/or therapeutic agents for use in humans. The dosage of such agents lies preferably within a range of circulating concentrations that include the $ED_{50}$ with little or no toxicity. The dosage may vary within this range depending upon the dosage form employed and the route of administration utilized. For any agent used in the method of the invention, the therapeutically effective dose can be estimated initially from cell culture assays. A dose may be formulated in animal models to achieve a circulating plasma concentration range that includes the $IC_{50}$ (i.e., the concentration of the test compound that achieves a half-maximal inhibition of symptoms) as determined in cell culture. Such information can be used to more accurately determine useful doses in humans. Levels in plasma may be measured, for example, by high performance liquid chromatography.

Further, any assays known to those skilled in the art can be used to evaluate the prophylactic and/or therapeutic utility of the combinatorial therapies disclosed herein for a WNV infection.

5.7 Diagnostic Methods

Labeled antibodies, fragments, derivatives and analogs thereof, which immunospecifically bind to a WNV antigen can be used for diagnostic purposes to detect, diagnose, or monitor a WNV infection. The invention provides for the detection of a WNV infection, comprising: (a) assaying the expression of a WNV antigen in cells or a tissue sample of a subject using one or more humanized antibodies or fragments thereof that immunospecifically bind to the WNV antigen; and (b) comparing the level of the WNV antigen with a control level, e.g., levels in normal tissue samples not infected with WNV, whereby an increase in the assayed level of WNV antigen compared to the control level of the WNV antigen is indicative of a WNV infection.

The invention provides a diagnostic assay for diagnosing a WNV infection, comprising: (a) assaying for the level of a WNV antigen in cells or a tissue sample of an individual using one or more humanized antibodies or fragments thereof that immunospecifically bind to a WNV antigen; and (b) comparing the level of the WNV antigen with a control level, e.g., levels in normal tissue samples not infected with WNV, whereby an increase in the assayed WNV antigen level compared to the control level of the WNV antigen is indicative of a WNV infection. A more definitive diagnosis of WNV infection may allow health professionals to employ preventative measures or aggressive treatment earlier thereby preventing the development or further progression of WNV infection.

Humanized antibodies of the invention, or fragments thereof, can be used to assay WNV antigen levels in a biological sample using classical immunohistological methods as described herein or as known to those of skill in the art (e.g., see Jalkanen et al., 1985, J. Cell. Biol. 101:976-985; and Jalkanen et al., 1987, J. Cell. Biol. 105:3087-3096). Other antibody-based methods useful for detecting protein gene expression include immunoassays, such as the enzyme linked immunosorbent assay (ELISA) and the radioimmunoassay (RIA). Suitable antibody assay labels are known in the art and include enzyme labels, such as, alkaline phosphatase, glucose oxidase; radioisotopes, such as iodine ($^{125}I$, $^{131}I$), carbon ($^{14}C$), sulfur ($^{35}S$), tritium ($^{3}H$), indium ($^{121}In$), and technetium ($^{99m}Tc$); luminescent labels, such as luminol; and fluorescent labels, such as fluorescein and rhodamine, and biotin.

One aspect of the invention is the detection and diagnosis of a WNV infection in a human. In one embodiment, diagnosis comprises: a) administering (for example, parenterally, subcutaneously, or intraperitoneally) to a subject an effective amount of a labeled antibody or fragment thereof that immunospecifically binds to a WNV antigen; b) waiting for a time interval following the administering for permitting the labeled antibody or fragment thereof to preferentially concentrate at sites in the subject where the WNV antigen is expressed (and for unbound labeled molecule to be cleared to background level); c) determining background level; and d) detecting the labeled antibody or fragment thereof in the subject, such that detection of labeled antibody or fragment thereof above the background level indicates that the subject has a WNV infection. In accordance with this embodiment, the antibody may be labeled with an imaging moiety which is detectable using an imaging system known to one of skill in the art. Background level can be determined by various methods including, comparing the amount of labeled molecule detected to a standard value previously determined for a particular system.

It will be understood in the art that the size of the subject and the imaging system used will determine the quantity of imaging moiety needed to produce diagnostic images. In the case of a radioisotope moiety, for a human subject, the quantity of radioactivity injected will normally range from about 5 to 20 millicuries of $^{99m}Tc$. The labeled antibody or antibody fragment will then preferentially accumulate at the location of cells which contain the specific protein. In vivo tumor imaging is described in S. W. Burchiel et al., "Immunopharmacokinetics of Radiolabeled Antibodies and Their Fragments." (Chapter 13 in Tumor Imaging: The Radiochemical Detection of Cancer, S. W. Burchiel and B. A. Rhodes, eds., Masson Publishing Inc. (1982).

Depending on several variables, including the type of label used and the mode of administration, the time interval following the administration for permitting the labeled molecule to preferentially concentrate at sites in the subject and for unbound labeled molecule to be cleared to background level is 6 to 48 hours or 6 to 24 hours or 6 to 12 hours. In another embodiment the time interval following administration is 5 to 20 days or 5 to 10 days.

In one embodiment, monitoring of a WNV infection is carried out by repeating the method for diagnosing the WNV infection, for example, one month after initial diagnosis, six months after initial diagnosis, one year after initial diagnosis, etc.

Presence of the labeled molecule can be detected in the subject using methods known in the art for in vivo scanning. These methods depend upon the type of label used. Skilled artisans will be able to determine the appropriate method for detecting a particular label. Methods and devices that may be used in the diagnostic methods of the invention include, but are not limited to, computed tomography (CT), whole body scan such as position emission tomography (PET), magnetic resonance imaging (MRI), and sonography.

In a specific embodiment, the molecule is labeled with a radioisotope and is detected in the patient using a radiation responsive surgical instrument (Thurston et al., U.S. Pat. No. 5,441,050). In another embodiment, the molecule is labeled with a fluorescent compound and is detected in the patient using a fluorescence responsive scanning instrument. In another embodiment, the molecule is labeled with a positron emitting metal and is detected in the patient using positron emission-tomography. In yet another embodiment, the molecule is labeled with a paramagnetic label and is detected in a patient using magnetic resonance imaging (MRI).

5.8 Kits

The invention provides a pharmaceutical pack or kit comprising one or more containers filled with humanized antibodies of the invention. In an alterative embodiment, a kit comprises an antibody fragment that immunospecifically binds to a WNV antigen. Additionally, one or more other prophylactic or therapeutic agents useful for the treatment of a disease can also be included in the pharmaceutical pack or kit. The invention also provides a pharmaceutical pack or kit comprising one or more containers filled with one or more of the ingredients of the pharmaceutical compositions of the invention. Optionally associated with such container(s) can be a notice in the form prescribed by a governmental agency regulating the manufacture, use or sale of pharmaceuticals or biological products, which notice reflects approval by the agency of manufacture, use or sale for human administration.

The present invention provides kits that can be used in the above methods. In one embodiment, a kit comprises one or more humanized antibodies of the invention. In another embodiment, a kit further comprises one or more other prophylactic or therapeutic anti-viral agents, in one or more containers. In another embodiment, a kit further comprises one or more cytotoxic antibodies.

In a specific embodiment, the kits of the present invention contain a substantially isolated WNV antigen as a control. Preferably, the kits of the present invention further comprise a control antibody which does not react with the WNV antigen. In another specific embodiment, the kits of the present invention contain a means for detecting the binding of an antibody to a WNV antigen (e.g., the antibody may be conjugated to a detectable substrate such as a fluorescent compound, an enzymatic substrate, a radioactive compound or a luminescent compound, or a second antibody which recognizes the first antibody may be conjugated to a detectable substrate). In specific embodiments, the kit may include a recombinantly produced or chemically synthesized WNV antigen. The WNV antigen provided in the kit may also be attached to a solid support. In a more specific embodiment the detecting means of the above-described kit includes a solid support to which WNV antigen is attached. Such a kit may also include a non-attached reporter-labeled anti-human antibody. In this embodiment, binding of the antibody to the WNV antigen can be detected by binding of the said reporter-labeled antibody.

In an additional embodiment, the invention includes a diagnostic kit for use in screening serum containing WNV antigens. The diagnostic kit includes a substantially isolated humanized antibody specifically immunoreactive with a WNV antigen, and means for detecting the binding of the WNV antigen to the antibody. In one embodiment, the antibody is attached to a solid support. The detecting means of the kit may include a second, labeled monoclonal antibody. Alternatively, or in addition, the detecting means may include a labeled, competing antigen.

In one diagnostic configuration, test serum is reacted with a solid phase reagent having a surface-bound WNV antigen obtained by the methods of the present invention. After the WNV antigen binds to a specific antibody, the unbound serum components are removed by washing, reporter-labeled anti-human antibody is added, unbound anti-human antibody is removed by washing, and a reagent is reacted with reporter-labeled anti-human antibody to bind reporter to the reagent in proportion to the amount of bound anti-WNV antigen antibody on the solid support. Typically, the reporter is an enzyme which is detected by incubating the solid phase in the presence of a suitable fluorometric, luminescent or calorimetric substrate (Sigma, St. Louis, Mo.).

The solid surface reagent in the above assay is prepared by known techniques for attaching protein material to solid support material, such as polymeric beads, dip sticks, 96-well plate or filter material. These attachment methods generally include non-specific adsorption of the protein to the support or covalent attachment of the protein, typically through a free amine group, to a chemically reactive group on the solid support, such as an activated carboxyl, hydroxyl, or aldehyde group. Alternatively, streptavidin coated plates can be used in conjunction with biotinylated antigen(s).

Thus, the invention provides an assay system or kit for carrying out this diagnostic method. The kit generally includes a support with surface-bound recombinant WNV antigen, and a reporter-labeled anti-human antibody for detecting surface-bound anti-WNV antigen antibody.

6. EXAMPLES

6.1 Humanization of Mouse Anti West Nile Virus MAB E16

RNA was converted to cDNA and the VH and VL segments were PCR amplified using the 5' RACE kit (Invitrogen, Inc.). Gene specific primers for the VH were SJ15R, SEQ ID NO. 57 (5' GGT CAC TGT CAC TGG CTC AGG G 3') and SJ16R, SEQ ID NO. 58 (5' AGG CGG ATC CAG GGG CCA GTG GAT AGA C 3'). Gene specific primers for the VL were SJ17R, SEQ ID NO. 59 (5' GCA CAC GAC TGA GGC ACC TCC AGA TG 3') and SJ18R, SEQ ID NO. 60 (5' CGG CGG ATC CGA TGG ATA CAG TTG GTG CAG CAT C 3'). The RACE product was inserted into the plasmid pCR2.1-TOPO using a TOPO TA Cloning kit (Invitrogen, Inc.). The resulting plasmids were then subjected to DNA sequencing to determine the VH and VL sequences for E16 and E34. The resulting sequences were then translated and the predicted amino acid sequence determined for each. From these sequences the framework (FR) and complementarity determining (CDR) regions were identified as defined by Kabat. The mouse VH was then joined to a human C-Gammal constant region and an Ig leader sequence and inserted into pCI-neo for mammalian expression. The mouse VL was joined to a human C-kappa segment and an Ig leader sequence and also cloned into pCI-neo for mammalian expression.

The humanized E16 VH consists of the CDR regions of E16 VH and the FR segments from the human germline VH1-18 VH segment and JH6. The humanized E16 VL consists of the CDR regions of E16 VL and the FR segments of the human germline VK-B3 VL segment and JK4. The humanized VH segments were assembled de novo from oligonucleotides combined and amplified by PCR. The humanized VL segments were assembled by PCR and overlapping PCR. The resulting fragment was then combined by PCR with a leader sequence and the appropriate constant region segment cloned into the expression vector pCI-neo as a Nhe I-EcoRI fragment. The DNA sequence of the resulting plasmids was confirmed by sequence analysis.

The alignment of the amino acid sequences of mouse E16 VH and humanized E16 VH is shown in FIG. 1A. The alignment of the amino acid sequences of mouse E16 VL and humanized E16 VL is shown in FIG. 1B.

6.2 Expression and Characterization of the Humanized E16 Heavy and Light Chains.

Chimeric E16 (chE16), humanized E16 (huE16) and hybrid E16 antibodies were expressed in HEK-293 cells by co-transfecting the following combinations of E16 heavy chain (HC) and E16 light chain expression plasmids: huE16HC/huE16LC, huE16HC/chE16LC, chE16HC/huE16LC and chE16HC/chE16LC. After three days in culture the amount of antibody expressed having a human IgG constant domain was quantitated by ELISA. Binding to WNV E-protein domain III (dIII) was determined by ELISA and antibody-capture ELISA as described below.

Protocol for ELISA assay: 100 ng/well of dIII was coated directly on 96-well Maxisorp plates at 4° C. overnight. A series of two-fold dilutions of conditioned medium of chE16, huE16, huE16HC/chE16LC or chE16HC/huE16LC starting from 5 ng/well was added to each well. The plate was incubated at room temperature for 1 hour, then binding was detected by HRP conjugated F(ab')$_2$ goat anti human IgG F(ab')'$_2$ specific secondary antibody (Jackson ImmunoResearch, Inc.) at 1:10,000 dilution. After incubation with the secondary antibody for approximately 45 minutes, the plate was developed using a TMB substrate. After 5 minutes incubation, the reaction was stopped by adding 1% $H_2SO_4$. The $OD_{450}$ nm was read by SOFTmax program. Between each step, the plates were washed 3 times with PBS/0.1% Tween 20. Plates were blocked by 0.5% BSA in PBS/0.1% Tween 20 for 30 mins at room temperature before adding conditioned medium.

Protocol for antibody-capture ELISA assay: 2.5 ng/well of dIII was captured on 96-well Maxisorp plates by mouse anti-WNV E-protein antibody E9 at room temperature for 2 hours. A serial of two-fold dilution of conditioned medium of chE16, huE16, huE16HC/ch2B6LC or chE16HC/huE16LC starting from 5 ng/well was added to each well. The plate was incubated at room temperature for 1 hour, then binding was detected by HRP conjugated F(ab')$_2$ goat anti human IgG F(ab')'$_2$ specific secondary antibody (Jackson ImmunoResearch, Inc.) at 1:10,000 dilution. After incubation with the secondary antibody for approximately 45 minutes, the plate was developed using a TMB substrate. After 5 minutes incubation, the reaction was stopped by adding 1% $H_2SO_4$. The $OD_{450}$ nm was read by SOFTmax program. Between each step, the plates were washed 3 times with PBS/0.1% Tween20. Plates were blocked by 0.5% BSA in PBS/0.1% Tween 20 for 30 mins at room temperature before adding conditioned medium.

Results: The results of the ELISA assay depicted in FIG. 2A indicated that all mAbs bound to the receptor with similar affinity/aviditiy. In the dIII capture ELISA, depicted in FIG. 2B, huE16 exhibited lower binding levels than chE16 or either hybrid E16. One interpretation of this result is that the humanized E16 may shift the binding epitope slightly so that it now competes with the E9 antibody used to originally capture dIII.

6.3 Generation, Expression and Characterization of Humanized E16, Heavy and Light Chain Variants.

To further improve the binding affinity/avidity of humanized E16 antibody, variants of huE16LC and huE16HC were created using site directed mutagenesis (Stratagene kit). For example, HuE16LC-2 (Y49S) was formed by mutating the tyrosine (Y) at huE16LC position 49 to serine (S).

Mutated huE16 antibody was expressed by co-transfection of HEK-293 cells with the variant huE16HC and huE16LC according to the following combinations:

| Expressed Antibody | Heavy Chain | Light Chain |
|---|---|---|
| huE16-1.1 | huE16HC | huE16LC |
| huE16-1.2 | huE16HC | huE16LC-2 (Y49S) |
| huE16-2.1 | huE16HC-2 (V67A, M69F, T71A) | huE16LC |
| huE16-2.2 | huE16HC-2 (V67A, M69F, T71A) | huE16LC-2 (Y49S) |
| huE16-3.1 | huE16-3 (T71A) | huE16LC |
| huE16-3.2 | huE16-2 (T71A) | huE16LC-2 (Y49S) |

After three days in culture the amount of human IgG expressed was quantitated by ELISA. Binding to WNV E-protein domain III (dIII) was determined by ELISA and antibody-capture ELISA assays as described above.

Results: The effects of mutating huE16LC on binding affinity are depicted in FIGS. 3A and 3B. The results indicate that the Y49S change in the light chain improved the binding of E16 to the antigen. This improvement was further enhanced when combined with the described mutations in huE16HC as shown in FIGS. 4 and 5. A comparison of the last two figures also shows that the single (T71A) mutation in huE16HC is functionally equivalent to the triple mutation (V67A, M69F, T71A) in huE16HC in terms of mAb binding to the receptor.

6.4 Model of WNV Encephalitis in Mice and Therapeutic and Prophylaxis Studies of Humanized Anti West Nile Virus MAB E16

Murine model: A WNV infection model was established in C57BL/6 (wild type) mice that closely paralleled the human disease. One week after subcutaneous inoculation, wild-type mice developed systemic and central nervous system (CNS) infection with a subset progressing to paralysis and death. Younger mice were found to have consistently higher mortality rates and thus offered the possibility for greater mortality benefit in response to treatment. Five week-old mice were selected for all therapeutic studies; for this group, footpad inoculation with $10^2$ plaque-forming units (PFU) of WNV resulted in 87% mortality in the absence of therapy.

Prophylaxis study of human γ-globulin: To confirm that antibodies mediated protection against WNV, the efficacy of purified immune human γ-globulin against WNV infection was evaluated in the mouse model described above. Purified immune human γ-globulin, specifically human γ-globulin with immunoreactivity against WNV, was obtained from pooled donors in Israel: an area of sporadic outbreaks of WNV such that 10-20% of the population carries antibodies against WNV. A single 15 mg dose of purified immune human γ-globulin against WNV was administered via intraperitoneal (IP) injection immediately prior (day 0) to or at the indicated days after footpad inoculation with $10^2$ PFU of WNV.

Figure 6:
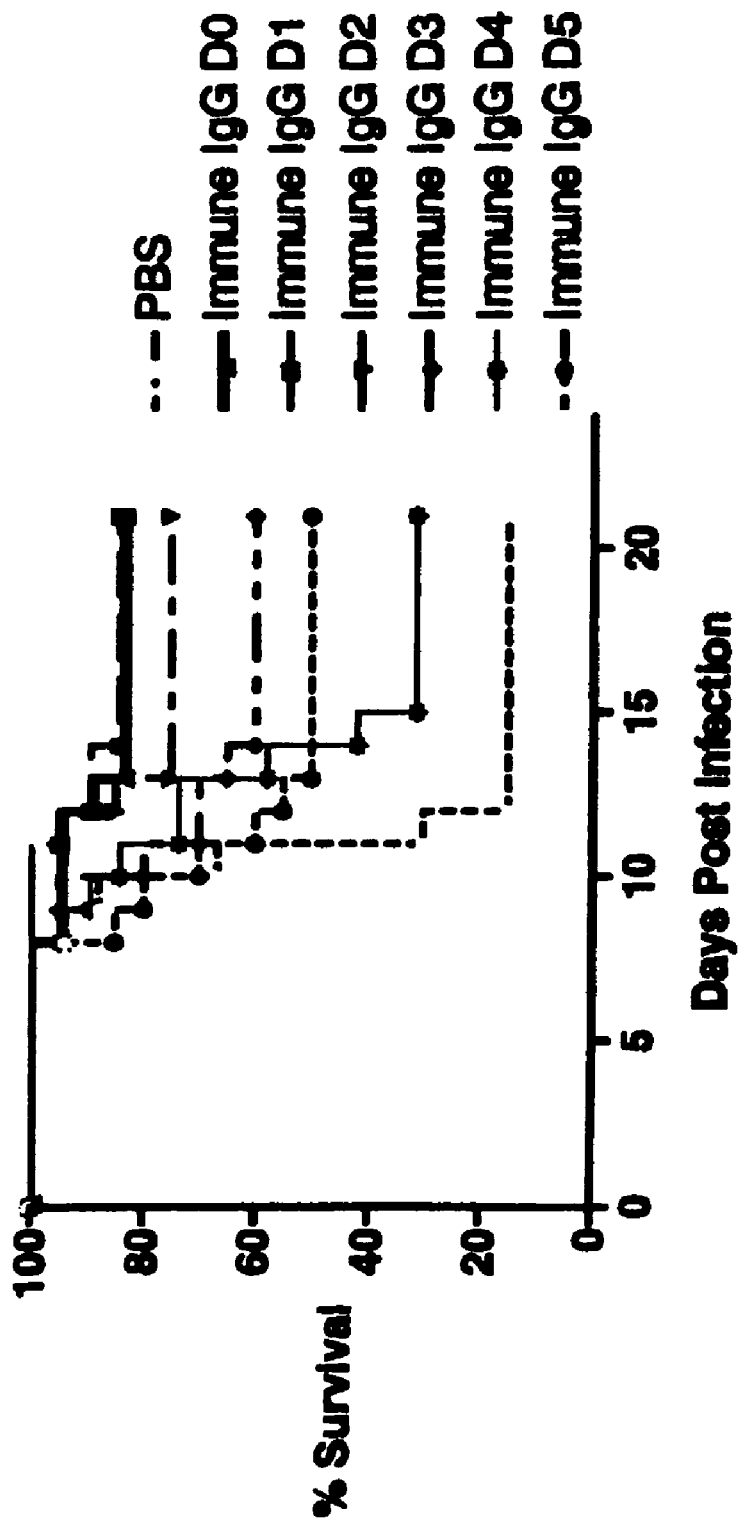

The results depicted in FIG. 6 indicate that treatment with immune γ-globulin at day 1, 2, 3, 4 or 5 (D1, D2, D3, D4 and D5, respectively) post infection increased the average survival time and decreased mortality rates. The beneficial effect of therapy at day 5 is interesting because it suggests that antibody may be able to limit the disease even after it has spread to the CNS.

Post exposure therapeutic studies with murine anti-WNV mAb: Several murine anti-WNV protein E mAbs and a control mAb against SARS ORF7a were evaluated for therapeutic effect in the described mouse model, FIG. 7A. At 4 days post infection, intra-peritoneal administration of 0.5 mg of mAb E16 produced the greatest increase in both mean survival time and mortality benefit.

Figures 7A, 7B:
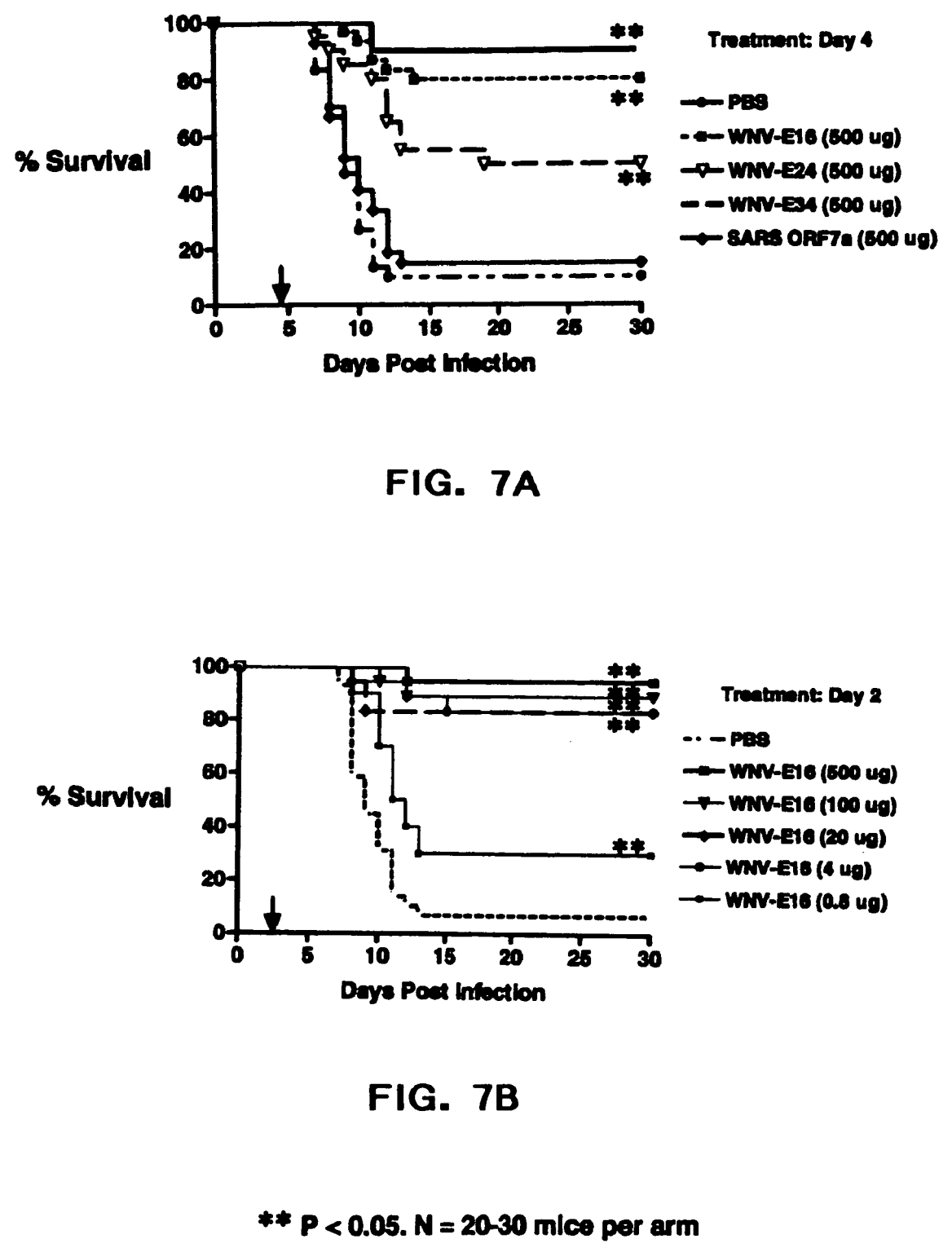

The dose response to this antibody was further examined as depicted in FIG. 7B. At 2 days post infection, intra-peritoneal administration of 0.8 μg improved survival from 5% to 30% at day 30. More dramatic improvements were seen at doses of at least 4 μg mAb E16; at this dose, day 30 survival improved by at least 75% as compared to control. Although higher doses did correlate with improved survival, the highly comparable survival curves for doses ranging from 4 to 500 μg indicate only minimal gains from a substantially increased concentration of circulating antibody. This may suggest a threshold of antigen saturation beyond which the administered antibody has no available target.

Figure 8:
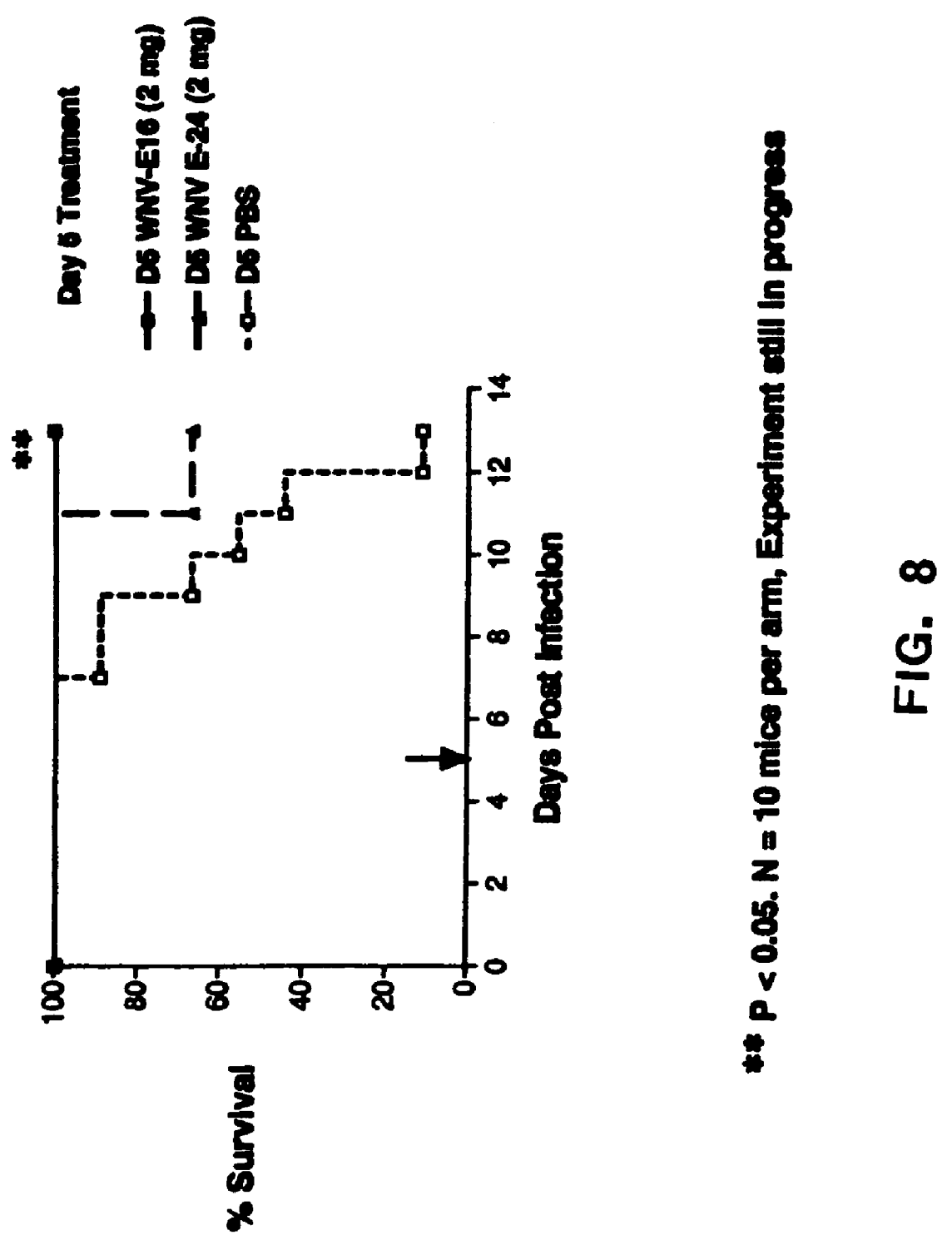

The more effective of the murine anti-WNV protein E antibodies, mAb E16 and mAb E24, were also tested at the higher viral load at 5 days post infection and at an increased dose of 2 mg, FIG. 8. Administration of either mAb E16 and mAb E24 increased the average survival over the control with mAb16 the seemingly more effective of the two in the short term.

Figure 9A:
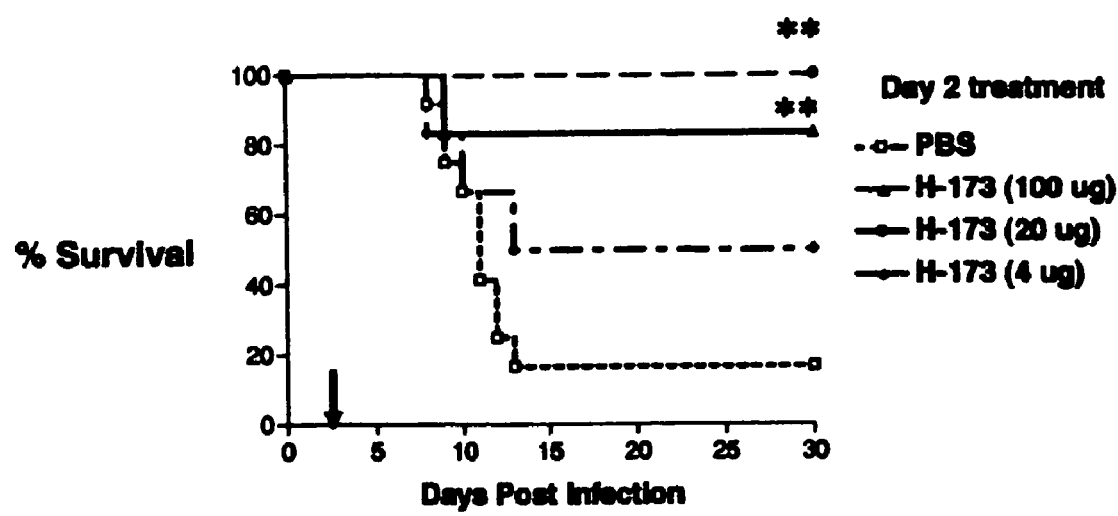
Figure 9B:
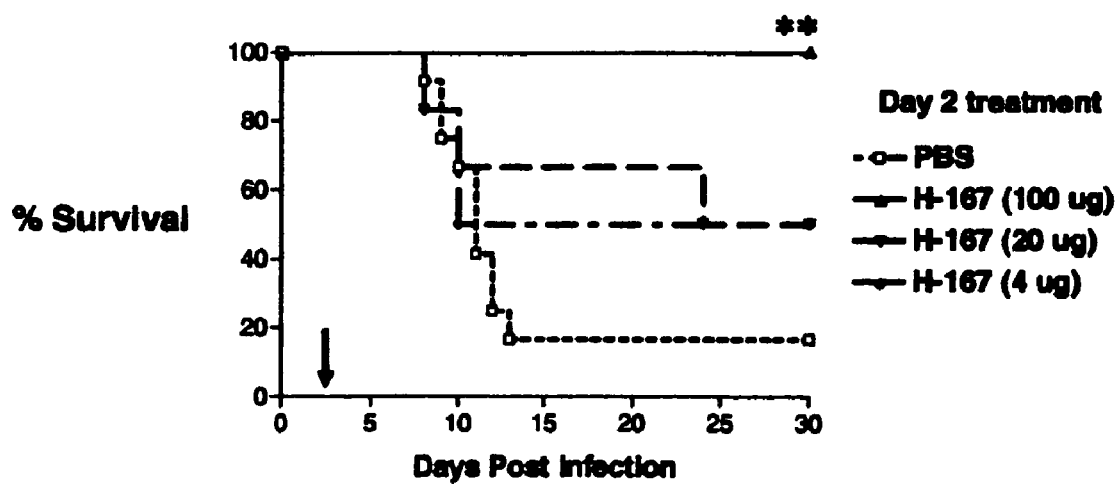

Post exposure therapeutic studies with humanized anti-WNVmAb E16: Two humanized versions of murine mAb E16 have been tested in the mouse model, mAb E16H-173 (huE16-1.2) and mAb E16H-167 (huE16-1.1). As shown in FIGS. 9A and 9B, respectively, doses of at least 4 μg at 2 days post-infection substantially increased 30 day survival. For either version of the humanized mAb E16, higher doses improved survival; however, clear differences in their functioning are apparent.

Prophylaxis studies with humanized anti-WNV mAB E16: A humanized version of murine mAB E16, hE16-3.2, was tested in the above mouse model in a prophylaxis study. Groups of 10 mice each were administered PBS or hE16-3.2 at doses of 0.03, 0.1, 0.3, 1.0 or 3.0 mg/kg via an intraperitoneal route. Approximately 24 hr later animals were bled and administered $10^2$ PFU of WNV via footpad inoculation. Survival was monitored over a 24 day period. Antibody levels were determined by ELISA. Data reflects 10 mice per condition. FIG. 10 and Table 6 depict the survival of mice administered varying doses of hE16-3.2. Significant protection was seen at all doses.

TABLE 6

| Dose (mg/kg) | Survival (day 24) | Percent Survival |
| --- | --- | --- |
| 0 | 1/10 | 10% |
| 0.03 | 9/10 | 90% |
| 0.1 | 9/10 | 90% |
| 0.3 | 6/10 | 60% |
| 1.0 | 10/10 | 100% |
| 3.0 | 10/10 | 100% |

6.5 Clinical Trial of Humanized Anti West Nile Virus MAB E16

This study is a phase I trial of humanized mAb E16 administration to patients with active West Nile virus infection, and is designed to evaluate both its effect on WNV infection and its possible toxicity. Patients with suspected WNV infection may be enrolled after positive identification of viral DNA/RNA or infectious virus in serum or cerebrospinal fluid. Accepted diagnostic tests include immunohistochemisty with anti-WNV antibodies and detection of the WNV genome through polymerase chain reaction (PCR), Southern blot or in situ hybridization analysis.

No specific therapy currently exists for West Nile viral illness, limiting treatment to supportive care. Thus no alternative WNV treatments are given in association with the anti-WNV antibody. However, because sub-neutralizing concentrations of antibody enhance flatavirus replication in myeloid cells in vitro, acute or unusual progression of the disease will halt administration of anti-WNV antibody.

Anti-WNV dose and administration: Initial patients receive 0.5 mg/kg humanized mAb E16 administered as a 1 hour intravenous infusion. Given adequate tolerance, the dose will be increased stepwise in subsequent patients to 5 mg/kg. Additionally, the method of administration may be changed to bolus injection.

Study Protocol and Criteria: Toxicity of humanized mAb E16 is evaluated in patients according to the World Health Organization Toxicity Criteria: blood pressure, temperature and heart rate are monitored every 10 minutes during mAb E16 infusion, then every hour for 3 hours and finally every 3 hours for 24 hours. Hematologic, renal and liver function tests are conducted every other day for one week and on day 15, 30, 60 and 120 post injection.

Serum and/or tissue samples are obtained once a day for two weeks so that the effects of mAb E16 on viremia and viral load may be determined by plaque and fluorogenic RT-PCR assays. Virologic analysis will quantitatively define the effect of mAb E16 on the progression of WNV infection, and pathologic studies will asses their effect on related tissue damage and leukocyte infiltration.

The present invention is not to be limited in scope by the specific embodiments described which are intended as single illustrations of individual aspects of the invention, and functionally equivalent methods and components are within the scope of the invention. Indeed, various modifications of the invention, in addition to those shown and described herein will become apparent to those skilled in the art from the foregoing description and accompanying drawings. Such modifications are intended to fall within the scope of the appended claims.

Various references are cited herein, the disclosure of which are incorporated by reference in their entirety.

The invention claimed is:

1. A humanized antibody or an epitope binding fragment thereof comprising three VH complementary determining regions (CDRs) and three VL CDRs,
   wherein the CDRs are from monoclonal antibody E16, E24, or E34,
   wherein one or more of said CDRs optionally differs by one amino acid substitution from a CDR from monoclonal antibody E16, E24, or E34, and
   wherein the antibody or epitope binding fragment thereof specifically binds a West Nile Virus (WNV) epitope defined by monoclonal antibody E16, E24, or E34.

2. The humanized antibody of claim 1 comprising a humanized variable region having a heavy chain and a light chain, said heavy chain region comprising the amino acid sequence of SEQ ID NO: 20, SEQ ID NO: 21, SEQ ID NO: 22, SEQ ID NO: 23, SEQ ID NO: 37, or SEQ ID NO: 46 and said light chain region comprising the amino acid sequence of SEQ ID NO: 25, SEQ ID NO: 26, SEQ ID NO: 38, or SEQ ID NO: 47.

3. The humanized antibody of claim 1 comprising a VH CDR1 comprising the amino acid sequence of SEQ ID NO: 1 or SEQ ID NO: 27, a VH CDR2 comprising the amino acid sequence of SEQ ID NO: 2, SEQ ID NO: 28, or SEQ ID NO: 39, and
   a VH CDR3 comprising the amino acid sequence of SEQ ID NO: 3, SEQ ID NO: 29, or SEQ ID NO: 40.

4. The humanized antibody of claim 1 comprising a VL CDR1 having the amino acid sequence of SEQ ID NO: 11, a VL CDR2 comprising the amino acid sequence of SEQ ID NO: 12, and a VL CDR3 comprising the amino acid sequence of SEQ ID NO: 13 or SEQ ID NO: 34.

5. The humanized antibody of claim 1 comprising a framework region comprising at least one amino acid modification in heavy chain FR3 or light chain FR2.

6. The humanized antibody of claim 5, wherein the at least one amino acid modification in heavy chain FR3 comprises a substitution at position 5, 6, 9, 11, 12, 19, 20, 25, 30, 38, 40, 43, 48, 66, 67, 69, 71, 75, 76, 79, 81, 82A, 83, 85, 87, 105, or 109.

7. The humanized antibody of claim 5, wherein the at least one amino acid modification in light chain FR2 comprises a substitution at position 8, 9, 10, 11, 12, 13, 15, 17, 19, 20, 22, 43, 49, 63, 71, 78, 83, 85, or 100.

8. A pharmaceutical composition comprising (i) a therapeutically effective amount of the humanized antibody of any of claims 1 or 2-7; and (ii) a pharmaceutically acceptable carrier.

9. A method of treating a WNV infection in a patient, said method comprising administering to said patient a therapeutically effective amount of the humanized antibody of any of claims 1 or 2-7.

10. The method of claim 9 further comprising administering an anti-viral agent.

11. The method of claim 10, wherein the anti-viral agent is selected from the group consisting of protease inhibitors, nucleoside reverse transcriptase inhibitors, non-nucleoside reverse transcriptase inhibitors, nucleoside analogs, and alpha-interferons.

12. The method of claim 9, wherein said patient is human.

13. A method of diagnosis of WNV infection in a subject comprising:
   (a) contacting a biological sample from said subject with an effective amount of the humanized antibody of any of claims 1 or 2-7; and
   (b) detecting binding of said antibody, wherein detection of said detectable marker above a background or standard level indicates that said subject has a WNV infection.

14. The method of claim 13, wherein said detectable marker is a chemiluminescent, enzymatic, fluorescent, or radioactive label.

15. A hybridoma that produces antibody E16, E24, or E34, which is deposited at the American Type Culture Collection and assigned Accession Number PTA-6050, PTA-6051, or PTA-6052, respectively.

16. A plasmid that encodes a humanized antibody, wherein the plasmid is designated pMGX623, pMGX624, pMGX625, pMGX626, or pMGX627 and is deposited at the American Type Culture Collection with Accession Number PTA-6199, PTA-6200, PTA-6201, PTA-6202, or PTA-6203, respectively.

17. The humanized antibody of claim 1, wherein the humanized antibody is an epitope-binding antibody fragment.

18. The humanized antibody of claim 17, wherein the epitope-binding antibody fragment is a Fab, F(ab')$_2$, or scFv fragment.

19. The method of claim 10, wherein the anti-viral agent is selected from the group consisting of zidovudine, acyclovir, gangcyclovir, vidarabine, idoxuridine, trifluridine, and ribavirin, foscarnet, amantadine, rimantadine, saquinavir, indinavir, amprenavir, lopinavir, ritonavir, adefovir, clevadine, entecavir, and pleconaril.

* * * * *

SEQUENCE LISTING

```
<160> NUMBER OF SEQ ID NOS: 60

<210> SEQ ID NO 1
<211> LENGTH: 5
<212> TYPE: PRT
<213> ORGANISM: mus.
<220> FEATURE:
<223> OTHER INFORMATION: Heavy chain variable CDR1 from clone E16
```

```
<400> SEQUENCE: 1

Asp Tyr Trp Ile Glu
1               5

<210> SEQ ID NO 2
<211> LENGTH: 17
<212> TYPE: PRT
<213> ORGANISM: mus.
<220> FEATURE:
<223> OTHER INFORMATION: Heavy chain variable CDR2 from clone E16

<400> SEQUENCE: 2

Asp Ile Leu Cys Gly Thr Gly Arg Thr Arg Tyr Asn Glu Lys Leu Lys
1               5                   10                  15

Ala

<210> SEQ ID NO 3
<211> LENGTH: 10
<212> TYPE: PRT
<213> ORGANISM: mus.
<220> FEATURE:
<223> OTHER INFORMATION: Heavy chain variable CDR3 from clone E16

<400> SEQUENCE: 3

Ser Ala Ser Tyr Gly Asp Tyr Ala Asp Tyr
1               5                   10

<210> SEQ ID NO 4
<211> LENGTH: 30
<212> TYPE: PRT
<213> ORGANISM: mus.
<220> FEATURE:
<223> OTHER INFORMATION: Heavy chain variable FR1 from clone E16

<400> SEQUENCE: 4

Gln Val Gln Leu Gln Gln Ser Gly Ser Glu Leu Met Lys Pro Gly Ala
1               5                   10                  15

Ser Val Gln Ile Ser Cys Lys Ala Thr Gly Tyr Thr Phe Ser
            20                  25                  30

<210> SEQ ID NO 5
<211> LENGTH: 14
<212> TYPE: PRT
<213> ORGANISM: mus.
<220> FEATURE:
<223> OTHER INFORMATION: Heavy chain variable FR2 from clone E16

<400> SEQUENCE: 5

Trp Val Lys Gln Arg Pro Gly His Gly Leu Glu Trp Ile Gly
1               5                   10

<210> SEQ ID NO 6
<211> LENGTH: 32
<212> TYPE: PRT
<213> ORGANISM: mus.
<220> FEATURE:
<223> OTHER INFORMATION: Heavy chain variable FR3 from clone E16

<400> SEQUENCE: 6

Met Ala Thr Phe Thr Ala Asp Thr Ser Ser Asn Thr Ala Phe Met Gln
1               5                   10                  15

Leu Ser Ser Leu Thr Ser Glu Asp Ser Ala Val Tyr Tyr Cys Ala Arg
            20                  25                  30
```

```
<210> SEQ ID NO 7
<211> LENGTH: 32
<212> TYPE: PRT
<213> ORGANISM: homo sapiens
<220> FEATURE:
<223> OTHER INFORMATION: Heavy chain variable FR3 from VH1-18

<400> SEQUENCE: 7

Arg Val Thr Met Thr Thr Asp Thr Ser Thr Ser Thr Ala Tyr Met Glu
 1               5                  10                  15

Leu Arg Ser Leu Arg Ser Asp Asp Thr Ala Val Tyr Tyr Cys Ala Arg
            20                  25                  30

<210> SEQ ID NO 8
<211> LENGTH: 32
<212> TYPE: PRT
<213> ORGANISM: Artificial Sequence
<220> FEATURE:
<223> OTHER INFORMATION: Mutated Heavy chain variable FR3 from VH1-18

<400> SEQUENCE: 8

Arg Ala Thr Phe Thr Ala Asp Thr Ser Thr Ser Thr Ala Tyr Met Glu
 1               5                  10                  15

Leu Arg Ser Leu Arg Ser Asp Asp Thr Ala Val Tyr Tyr Cys Ala Arg
            20                  25                  30

<210> SEQ ID NO 9
<211> LENGTH: 32
<212> TYPE: PRT
<213> ORGANISM: Artificial Sequence
<220> FEATURE:
<223> OTHER INFORMATION: Mutated Heavy chain variable FR3 from VH1-18

<400> SEQUENCE: 9

Arg Val Thr Met Thr Ala Asp Thr Ser Thr Ser Thr Ala Tyr Met Glu
 1               5                  10                  15

Leu Arg Ser Leu Arg Ser Asp Asp Thr Ala Val Tyr Tyr Cys Ala Arg
            20                  25                  30

<210> SEQ ID NO 10
<211> LENGTH: 11
<212> TYPE: PRT
<213> ORGANISM: mus.
<220> FEATURE:
<223> OTHER INFORMATION: Heavy chain variable FR4 from clone E16

<400> SEQUENCE: 10

Trp Gly His Gly Thr Thr Leu Thr Val Ser Ser
 1               5                  10

<210> SEQ ID NO 11
<211> LENGTH: 11
<212> TYPE: PRT
<213> ORGANISM: mus.
<220> FEATURE:
<223> OTHER INFORMATION: Light chain variable CDR1 from clones E16, E24
      and E34

<400> SEQUENCE: 11

Lys Ala Ser Gln Asp Val Ser Thr Ala Val Ala
 1               5                  10

<210> SEQ ID NO 12
<211> LENGTH: 7
<212> TYPE: PRT
<213> ORGANISM: mus.
```

```
<220> FEATURE:
<223> OTHER INFORMATION: Light chain variable CDR2 from clones E16, E24
      and E34

<400> SEQUENCE: 12

Trp Ala Ser Thr Arg His Thr
1               5

<210> SEQ ID NO 13
<211> LENGTH: 9
<212> TYPE: PRT
<213> ORGANISM: mus.
<220> FEATURE:
<223> OTHER INFORMATION: Light chain variable CDR3 from clones E16, E24
      and E34

<400> SEQUENCE: 13

Gln Gln His Tyr Thr Thr Pro Leu Thr
1               5

<210> SEQ ID NO 14
<211> LENGTH: 23
<212> TYPE: PRT
<213> ORGANISM: mus.
<220> FEATURE:
<223> OTHER INFORMATION: Light chain variable FR1 from clones E16 and
      E24

<400> SEQUENCE: 14

Asp Ile Val Met Thr Gln Ser His Lys Phe Met Ser Thr Ser Val Gly
1               5                   10                  15

Asp Arg Val Ser Ile Thr Cys
            20

<210> SEQ ID NO 15
<211> LENGTH: 15
<212> TYPE: PRT
<213> ORGANISM: mus.
<220> FEATURE:
<223> OTHER INFORMATION: Light chain variable FR2 from clones E16

<400> SEQUENCE: 15

Trp Tyr Gln Gln Lys Pro Gly Gln Ser Pro Lys Leu Leu Ile Ser
1               5                   10                  15

<210> SEQ ID NO 16
<211> LENGTH: 15
<212> TYPE: PRT
<213> ORGANISM: homo sapiens
<220> FEATURE:
<223> OTHER INFORMATION: Light chain variable FR2 from VK-B3

<400> SEQUENCE: 16

Trp Tyr Gln Gln Lys Pro Gly Gln Pro Pro Lys Leu Leu Ile Tyr
1               5                   10                  15

<210> SEQ ID NO 17
<211> LENGTH: 15
<212> TYPE: PRT
<213> ORGANISM: Artificial Sequence
<220> FEATURE:
<223> OTHER INFORMATION: Mutated Light chain variable FR2 from VK-B3

<400> SEQUENCE: 17

Trp Tyr Gln Gln Lys Pro Gly Gln Pro Pro Lys Leu Leu Ile Ser
1               5                   10                  15
```

<210> SEQ ID NO 18
<211> LENGTH: 32
<212> TYPE: PRT
<213> ORGANISM: mus.
<220> FEATURE:
<223> OTHER INFORMATION: Light chain variable FR3 from clones E16 and E24

<400> SEQUENCE: 18

```
Gly Val Pro Asp Arg Phe Thr Gly Ser Gly Ser Gly Thr Asp Tyr Thr
1               5                   10                  15
Leu Thr Ile Ser Ser Val Gln Ala Glu Asp Leu Ala Leu Tyr Tyr Cys
            20                  25                  30
```

<210> SEQ ID NO 19
<211> LENGTH: 10
<212> TYPE: PRT
<213> ORGANISM: mus.
<220> FEATURE:
<223> OTHER INFORMATION: Light chain variable FR4 from clones E16 and E24

<400> SEQUENCE: 19

```
Phe Gly Ala Gly Thr Lys Leu Glu Leu Lys
1               5                   10
```

<210> SEQ ID NO 20
<211> LENGTH: 119
<212> TYPE: PRT
<213> ORGANISM: mus.
<220> FEATURE:
<223> OTHER INFORMATION: Heavy chain variable from clones E16

<400> SEQUENCE: 20

```
Gln Val Gln Leu Gln Gln Ser Gly Ser Glu Leu Met Lys Pro Gly Ala
1               5                   10                  15
Ser Val Gln Ile Ser Cys Lys Ala Thr Gly Tyr Thr Phe Ser Asp Tyr
            20                  25                  30
Trp Ile Glu Trp Val Lys Gln Arg Pro Gly His Gly Leu Glu Trp Ile
        35                  40                  45
Gly Asp Ile Leu Cys Gly Thr Gly Arg Thr Arg Tyr Asn Glu Lys Leu
    50                  55                  60
Lys Ala Met Ala Thr Phe Thr Ala Asp Thr Ser Ser Asn Thr Ala Phe
65                  70                  75                  80
Met Gln Leu Ser Ser Leu Thr Ser Glu Asp Ser Ala Val Tyr Tyr Cys
                85                  90                  95
Ala Arg Ser Ala Ser Tyr Gly Asp Tyr Ala Asp Tyr Trp Gly His Gly
            100                 105                 110
Thr Thr Leu Thr Val Ser Ser
        115
```

<210> SEQ ID NO 21
<211> LENGTH: 119
<212> TYPE: PRT
<213> ORGANISM: Artificial Sequence
<220> FEATURE:
<223> OTHER INFORMATION: humanized E16 heavy chain version 1

<400> SEQUENCE: 21

```
Gln Val Gln Leu Val Gln Ser Gly Ala Glu Val Lys Lys Pro Gly Ala
1               5                   10                  15
Ser Val Lys Val Ser Cys Lys Ala Ser Gly Tyr Thr Phe Thr Asp Tyr
            20                  25                  30
```

```
Trp Ile Glu Trp Val Arg Gln Ala Pro Gly Gln Gly Leu Glu Trp Met
            35                  40                  45

Gly Asp Ile Leu Cys Gly Thr Gly Arg Thr Arg Tyr Asn Glu Lys Leu
     50                  55                  60

Lys Ala Arg Val Thr Met Thr Asp Thr Ser Thr Ser Thr Ala Tyr
 65                  70                  75                  80

Met Glu Leu Arg Ser Leu Arg Ser Asp Asp Thr Ala Val Tyr Tyr Cys
                 85                  90                  95

Ala Arg Ser Ala Ser Tyr Gly Asp Tyr Ala Asp Tyr Trp Gly Gln Gly
                100                 105                 110

Thr Thr Val Thr Val Ser Ser
            115

<210> SEQ ID NO 22
<211> LENGTH: 119
<212> TYPE: PRT
<213> ORGANISM: Artificial Sequence
<220> FEATURE:
<223> OTHER INFORMATION: humanized E16 heavy chain version 2

<400> SEQUENCE: 22

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Asp Tyr
             20                  25                  30

Trp Ile Glu Trp Val Arg Gln Ala Pro Gly Gln Gly Leu Glu Trp Met
            35                  40                  45

Gly Asp Ile Leu Cys Gly Thr Gly Arg Thr Arg Tyr Asn Glu Lys Leu
     50                  55                  60

Lys Ala Arg Ala Thr Phe Thr Ala Asp Thr Ser Ser Thr Ala Tyr
 65                  70                  75                  80

Met Glu Leu Arg Ser Leu Arg Ser Asp Asp Thr Ala Val Tyr Tyr Cys
                 85                  90                  95

Ala Arg Ser Ala Ser Tyr Gly Asp Tyr Ala Asp Tyr Trp Gly Gln Gly
                100                 105                 110

Thr Thr Val Thr Val Ser Ser
            115

<210> SEQ ID NO 23
<211> LENGTH: 119
<212> TYPE: PRT
<213> ORGANISM: Artificial Sequence
<220> FEATURE:
<223> OTHER INFORMATION: humanized E16 heavy chain version 3

<400> SEQUENCE: 23

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Asp Tyr
             20                  25                  30

Trp Ile Glu Trp Val Arg Gln Ala Pro Gly Gln Gly Leu Glu Trp Met
            35                  40                  45

Gly Asp Ile Leu Cys Gly Thr Gly Arg Thr Arg Tyr Asn Glu Lys Leu
     50                  55                  60

Lys Ala Arg Val Thr Met Thr Ala Asp Thr Ser Ser Thr Ala Tyr
 65                  70                  75                  80

Met Glu Leu Arg Ser Leu Arg Ser Asp Asp Thr Ala Val Tyr Tyr Cys
                 85                  90                  95
```

Ala Arg Ser Ala Ser Tyr Gly Asp Tyr Ala Asp Tyr Trp Gly Gln Gly
            100                 105                 110

Thr Thr Val Thr Val Ser Ser
        115

<210> SEQ ID NO 24
<211> LENGTH: 107
<212> TYPE: PRT
<213> ORGANISM: mus.
<220> FEATURE:
<223> OTHER INFORMATION: Light chain variable from clone E16

<400> SEQUENCE: 24

Asp Ile Val Met Thr Gln Ser His Lys Phe Met Ser Thr Ser Val Gly
 1               5                  10                  15

Asp Arg Val Ser Ile Thr Cys Lys Ala Ser Gln Asp Val Ser Thr Ala
            20                  25                  30

Val Ala Trp Tyr Gln Gln Lys Pro Gly Gln Ser Pro Lys Leu Leu Ile
        35                  40                  45

Ser Trp Ala Ser Thr Arg His Thr Gly Val Pro Asp Arg Phe Thr Gly
    50                  55                  60

Ser Gly Ser Gly Thr Asp Tyr Thr Leu Thr Ile Ser Ser Val Gln Ala
65                  70                  75                  80

Glu Asp Leu Ala Leu Tyr Tyr Cys Gln Gln His Tyr Thr Thr Pro Leu
                85                  90                  95

Thr Phe Gly Ala Gly Thr Lys Leu Glu Leu Lys
            100                 105

<210> SEQ ID NO 25
<211> LENGTH: 107
<212> TYPE: PRT
<213> ORGANISM: Artificial Sequence
<220> FEATURE:
<223> OTHER INFORMATION: humanized E16 light chain version 1

<400> SEQUENCE: 25

Asp Ile Val Met Thr Gln Ser Pro Asp Ser Leu Ala Val Ser Leu Gly
 1               5                  10                  15

Glu Arg Ala Thr Ile Asn Cys Lys Ala Ser Gln Asp Val Ser Thr Ala
            20                  25                  30

Val Ala Trp Tyr Gln Gln Lys Pro Gly Gln Pro Pro Lys Leu Leu Ile
        35                  40                  45

Tyr Trp Ala Ser Thr Arg His Thr Gly Val Pro Asp Arg Phe Ser Gly
    50                  55                  60

Ser Gly Ser Gly Thr Asp Phe Thr Leu Thr Ile Ser Ser Leu Gln Ala
65                  70                  75                  80

Glu Asp Val Ala Val Tyr Tyr Cys Gln Gln His Tyr Thr Thr Pro Leu
                85                  90                  95

Thr Phe Gly Gln Gly Thr Lys Leu Glu Ile Lys
            100                 105

<210> SEQ ID NO 26
<211> LENGTH: 107
<212> TYPE: PRT
<213> ORGANISM: Artificial Sequence
<220> FEATURE:
<223> OTHER INFORMATION: humanized E16 light chain version 2

<400> SEQUENCE: 26

Asp Ile Val Met Thr Gln Ser Pro Asp Ser Leu Ala Val Ser Leu Gly
1               5                   10                  15

Glu Arg Ala Thr Ile Asn Cys Lys Ala Ser Gln Asp Val Ser Thr Ala
            20                  25                  30

Val Ala Trp Tyr Gln Gln Lys Pro Gly Gln Pro Pro Lys Leu Leu Ile
        35                  40                  45

Ser Trp Ala Ser Thr Arg His Thr Gly Val Pro Asp Arg Phe Ser Gly
50                  55                  60

Ser Gly Ser Gly Thr Asp Phe Thr Leu Thr Ile Ser Ser Leu Gln Ala
65                  70                  75                  80

Glu Asp Val Ala Val Tyr Tyr Cys Gln Gln His Tyr Thr Thr Pro Leu
                85                  90                  95

Thr Phe Gly Gln Gly Thr Lys Leu Glu Ile Lys
            100                 105

<210> SEQ ID NO 27
<211> LENGTH: 5
<212> TYPE: PRT
<213> ORGANISM: mus.
<220> FEATURE:
<223> OTHER INFORMATION: Heavy chain variable CDR1 from clone E24

<400> SEQUENCE: 27

Ser Tyr Asp Ile Asn
1               5

<210> SEQ ID NO 28
<211> LENGTH: 17
<212> TYPE: PRT
<213> ORGANISM: mus.
<220> FEATURE:
<223> OTHER INFORMATION: Heavy chain variable CDR2 from clone E24

<400> SEQUENCE: 28

Trp Ile Tyr Pro Gly Asp Gly Arg Ile Lys Tyr Asn Glu Lys Phe Lys
1               5                   10                  15

Gly

<210> SEQ ID NO 29
<211> LENGTH: 10
<212> TYPE: PRT
<213> ORGANISM: mus.
<220> FEATURE:
<223> OTHER INFORMATION: Heavy chain variable CDR3 from clone E24

<400> SEQUENCE: 29

Gly Gly Ser Ser Gly Thr Tyr Phe Asp Tyr
1               5                   10

<210> SEQ ID NO 30
<211> LENGTH: 30
<212> TYPE: PRT
<213> ORGANISM: mus.
<220> FEATURE:
<223> OTHER INFORMATION: Heavy chain variable FR1 from clone E24

<400> SEQUENCE: 30

Gln Val Gln Leu Gln Gln Ser Gly Pro Glu Leu Val Lys Pro Gly Ala
1               5                   10                  15

Leu Val Lys Ile Ser Cys Lys Ala Ser Gly His Thr Phe Thr
            20                  25                  30

```
<210> SEQ ID NO 31
<211> LENGTH: 14
<212> TYPE: PRT
<213> ORGANISM: mus.
<220> FEATURE:
<223> OTHER INFORMATION: Heavy chain variable FR2 from clone E24 and E34

<400> SEQUENCE: 31

Trp Val Lys Gln Arg Pro Gly Gln Gly Leu Glu Trp Ile Gly
 1               5                  10

<210> SEQ ID NO 32
<211> LENGTH: 32
<212> TYPE: PRT
<213> ORGANISM: mus.
<220> FEATURE:
<223> OTHER INFORMATION: Heavy chain variable FR3 from clone E24

<400> SEQUENCE: 32

Lys Ala Ile Leu Thr Ala Asp Lys Ser Ser Ser Thr Ala Tyr Met Gln
 1               5                  10                  15

Leu Ser Ser Leu Thr Ser Glu Asn Ser Ala Val Tyr Phe Cys Ala Arg
             20                  25                  30

<210> SEQ ID NO 33
<211> LENGTH: 11
<212> TYPE: PRT
<213> ORGANISM: mus.
<220> FEATURE:
<223> OTHER INFORMATION: Heavy chain variable FR4 from clone E24 and E34

<400> SEQUENCE: 33

Trp Gly Gln Gly Thr Thr Leu Thr Val Ser Ser
 1               5                  10

<210> SEQ ID NO 34
<211> LENGTH: 9
<212> TYPE: PRT
<213> ORGANISM: mus.
<220> FEATURE:
<223> OTHER INFORMATION: Light chain variable CDR3 from clone E24

<400> SEQUENCE: 34

Gln Gln His Tyr Ser Asn Pro Pro Thr
 1               5

<210> SEQ ID NO 35
<211> LENGTH: 15
<212> TYPE: PRT
<213> ORGANISM: mus.
<220> FEATURE:
<223> OTHER INFORMATION: Light chain variable FWR2 from clone E24

<400> SEQUENCE: 35

Trp Tyr Gln Gln Lys Pro Gly Gln Ser Pro Lys Val Leu Ile Tyr
 1               5                  10                  15

<210> SEQ ID NO 36
<211> LENGTH: 10
<212> TYPE: PRT
<213> ORGANISM: mus.
<220> FEATURE:
<223> OTHER INFORMATION: Light chain variable FWR4 from clone E24

<400> SEQUENCE: 36

Phe Gly Gly Gly Thr Lys Leu Glu Ile Lys
 1               5                  10
```

```
<210> SEQ ID NO 37
<211> LENGTH: 119
<212> TYPE: PRT
<213> ORGANISM: mus.
<220> FEATURE:
<223> OTHER INFORMATION: Heavy chain variable from clone E24

<400> SEQUENCE: 37

Gln Val Gln Leu Gln Gln Ser Gly Pro Glu Leu Val Lys Pro Gly Ala
 1               5                  10                  15

Leu Val Lys Ile Ser Cys Lys Ala Ser Gly His Thr Phe Thr Ser Tyr
            20                  25                  30

Asp Ile Asn Trp Val Lys Gln Arg Pro Gly Gln Gly Leu Glu Trp Ile
        35                  40                  45

Gly Trp Ile Tyr Pro Gly Asp Gly Arg Ile Lys Tyr Asn Glu Lys Phe
 50                  55                  60

Lys Gly Lys Ala Ile Leu Thr Ala Asp Lys Ser Ser Thr Ala Tyr
 65                  70                  75                  80

Met Gln Leu Ser Ser Leu Thr Ser Glu Asn Ser Ala Val Tyr Phe Cys
                85                  90                  95

Ala Arg Gly Gly Ser Ser Gly Thr Tyr Phe Asp Tyr Trp Gly Gln Gly
            100                 105                 110

Thr Thr Leu Thr Val Ser Ser
        115

<210> SEQ ID NO 38
<211> LENGTH: 107
<212> TYPE: PRT
<213> ORGANISM: mus.
<220> FEATURE:
<223> OTHER INFORMATION: Light chain variable from clone E24

<400> SEQUENCE: 38

Asp Ile Val Met Thr Gln Ser His Lys Phe Met Ser Thr Ser Val Gly
 1               5                  10                  15

Asp Arg Val Ser Ile Thr Cys Lys Ala Ser Gln Asp Val Ser Thr Ala
            20                  25                  30

Val Ala Trp Tyr Gln Gln Lys Pro Gly Gln Ser Pro Lys Val Leu Ile
        35                  40                  45

Tyr Trp Ala Ser Thr Arg His Thr Gly Val Pro Asp Arg Phe Thr Gly
 50                  55                  60

Ser Gly Ser Gly Thr Asp Tyr Thr Leu Thr Ile Ser Ser Val Gln Ala
 65                  70                  75                  80

Glu Asp Leu Ala Leu Tyr Tyr Cys Gln Gln His Tyr Ser Asn Pro Pro
                85                  90                  95

Thr Phe Gly Gly Gly Thr Lys Leu Glu Ile Lys
            100                 105

<210> SEQ ID NO 39
<211> LENGTH: 17
<212> TYPE: PRT
<213> ORGANISM: mus.
<220> FEATURE:
<223> OTHER INFORMATION: Heavy chain variable CDR2 from clone E34

<400> SEQUENCE: 39

Trp Ile Phe Pro Gly Asp Gly Arg Ile Lys Tyr Asn Glu Gln Ile Lys
 1               5                  10                  15

Asp
```

<210> SEQ ID NO 40
<211> LENGTH: 10
<212> TYPE: PRT
<213> ORGANISM: mus.
<220> FEATURE:
<223> OTHER INFORMATION: Heavy chain variable CDR3 from clone E34

<400> SEQUENCE: 40

Ala Ser Tyr Tyr Gly Ser Ile Phe Asp Tyr
1               5                   10

<210> SEQ ID NO 41
<211> LENGTH: 30
<212> TYPE: PRT
<213> ORGANISM: mus.
<220> FEATURE:
<223> OTHER INFORMATION: Heavy chain variable FWR1 from clone E34

<400> SEQUENCE: 41

Gln Val Gln Leu Gln Gln Ser Gly Pro Glu Leu Val Lys Pro Gly Thr
1               5                   10                  15

Leu Val Lys Ile Ser Cys Lys Thr Ser Gly Tyr Thr Phe Thr
            20                  25                  30

<210> SEQ ID NO 42
<211> LENGTH: 32
<212> TYPE: PRT
<213> ORGANISM: mus.
<220> FEATURE:
<223> OTHER INFORMATION: Heavy chain variable FWR3 from clone E34

<400> SEQUENCE: 42

Lys Ala Thr Leu Thr Ala Asp Lys Ser Ser Ser Thr Ala Tyr Met Glu
1               5                   10                  15

Leu Ser Ser Leu Thr Ser Glu Asn Ser Ala Val Tyr Phe Cys Ala Arg
            20                  25                  30

<210> SEQ ID NO 43
<211> LENGTH: 23
<212> TYPE: PRT
<213> ORGANISM: mus.
<220> FEATURE:
<223> OTHER INFORMATION: Light chain variable FWR1 from clone E34

<400> SEQUENCE: 43

Asp Ile Val Met Thr Gln Ser His Lys Phe Met Ser Thr Ser Val Gly
1               5                   10                  15

Asp Arg Val Asn Ile Thr Cys
            20

<210> SEQ ID NO 44
<211> LENGTH: 15
<212> TYPE: PRT
<213> ORGANISM: mus.
<220> FEATURE:
<223> OTHER INFORMATION: Light chain variable FWR2 from clone E34

<400> SEQUENCE: 44

Trp Tyr Gln Gln Lys Pro Gly Gln Ser Pro Lys Leu Leu Ile Tyr
1               5                   10                  15

<210> SEQ ID NO 45
<211> LENGTH: 32
<212> TYPE: PRT
<213> ORGANISM: mus.

```
<220> FEATURE:
<223> OTHER INFORMATION: Light chain variable FWR3 from clone E34

<400> SEQUENCE: 45

Gly Val Pro Asp Arg Phe Thr Gly Ser Gly Ser Gly Thr His Tyr Thr
 1               5                  10                  15

Leu Thr Ile Ser Ser Val Gln Ala Glu Asp Leu Ala Leu Tyr Tyr Cys
            20                  25                  30

<210> SEQ ID NO 46
<211> LENGTH: 119
<212> TYPE: PRT
<213> ORGANISM: mus.
<220> FEATURE:
<223> OTHER INFORMATION: Heavy chain variable from clone E24

<400> SEQUENCE: 46

Gln Val Gln Leu Gln Gln Ser Gly Pro Glu Leu Val Lys Pro Gly Thr
 1               5                  10                  15

Leu Val Lys Ile Ser Cys Lys Thr Ser Gly Tyr Thr Phe Thr Ser Tyr
            20                  25                  30

Asp Ile Asn Trp Val Lys Gln Arg Pro Gly Gln Gly Leu Glu Trp Ile
        35                  40                  45

Gly Trp Ile Phe Pro Gly Asp Gly Arg Ile Lys Tyr Asn Glu Gln Ile
    50                  55                  60

Lys Asp Lys Ala Thr Leu Thr Ala Asp Lys Ser Ser Thr Ala Tyr
65                  70                  75                  80

Met Glu Leu Ser Ser Leu Thr Ser Glu Asn Ser Ala Val Tyr Phe Cys
                85                  90                  95

Ala Arg Ala Ser Tyr Tyr Gly Ser Ile Phe Asp Tyr Trp Gly Gln Gly
            100                 105                 110

Thr Thr Leu Thr Val Ser Ser
        115

<210> SEQ ID NO 47
<211> LENGTH: 107
<212> TYPE: PRT
<213> ORGANISM: mus.
<220> FEATURE:
<223> OTHER INFORMATION: Light chain variable from clone E24

<400> SEQUENCE: 47

Asp Ile Val Met Thr Gln Ser His Lys Phe Met Ser Thr Ser Val Gly
 1               5                  10                  15

Asp Arg Val Asn Ile Thr Cys Lys Ala Ser Gln Asp Val Ser Thr Ala
            20                  25                  30

Val Ala Trp Tyr Gln Gln Lys Pro Gly Gln Ser Pro Lys Leu Leu Ile
        35                  40                  45

Tyr Trp Ala Ser Thr Arg His Thr Gly Val Pro Asp Arg Phe Thr Gly
    50                  55                  60

Ser Gly Ser Gly Thr His Tyr Thr Leu Thr Ile Ser Ser Val Gln Ala
65                  70                  75                  80

Glu Asp Leu Ala Leu Tyr Tyr Cys Gln Gln His Tyr Thr Thr Pro Leu
                85                  90                  95

Thr Phe Gly Ala Gly Thr Lys Leu Glu Leu Lys
            100                 105
```

```
<210> SEQ ID NO 48
<211> LENGTH: 30
<212> TYPE: PRT
<213> ORGANISM: homo sapiens
<220> FEATURE:
<223> OTHER INFORMATION: Heavy chain variable FR1 from VH1-18

<400> SEQUENCE: 48

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr
             20                  25                  30

<210> SEQ ID NO 49
<211> LENGTH: 14
<212> TYPE: PRT
<213> ORGANISM: homo sapiens
<220> FEATURE:
<223> OTHER INFORMATION: Heavy chain variable FR2 from VH1-18

<400> SEQUENCE: 49

Trp Val Arg Gln Ala Pro Gly Gln Gly Leu Glu Trp Met Gly
 1               5                  10

<210> SEQ ID NO 50
<211> LENGTH: 11
<212> TYPE: PRT
<213> ORGANISM: homo sapiens
<220> FEATURE:
<223> OTHER INFORMATION: Heavy chain variable FR4 from JH-6

<400> SEQUENCE: 50

Trp Gly Gln Gly Thr Thr Val Thr Val Ser Ser
 1               5                  10

<210> SEQ ID NO 51
<211> LENGTH: 23
<212> TYPE: PRT
<213> ORGANISM: homo sapiens
<220> FEATURE:
<223> OTHER INFORMATION: Light chain variable FR1 from VK-B3

<400> SEQUENCE: 51

Asp Ile Val Met Thr Gln Ser Pro Asp Ser Leu Ala Val Ser Leu Gly
 1               5                  10                  15

Glu Arg Ala Thr Ile Asn Cys
             20

<210> SEQ ID NO 52
<211> LENGTH: 32
<212> TYPE: PRT
<213> ORGANISM: homo sapiens
<220> FEATURE:
<223> OTHER INFORMATION: Light chain variable FR3 from VK-B3

<400> SEQUENCE: 52

Gly Val Pro Asp Arg Phe Ser Gly Ser Gly Ser Gly Thr Asp Phe Thr
 1               5                  10                  15

Leu Thr Ile Ser Ser Leu Gln Ala Glu Asp Val Ala Val Tyr Tyr Cys
             20                  25                  30

<210> SEQ ID NO 53
<211> LENGTH: 10
<212> TYPE: PRT
<213> ORGANISM: homo sapiens
```

<220> FEATURE:
<223> OTHER INFORMATION: Light chain variable FR4 from VK-B3

<400> SEQUENCE: 53

Phe Gly Gln Gly Thr Lys Leu Glu Ile Lys
 1               5                  10

<210> SEQ ID NO 54
<211> LENGTH: 296
<212> TYPE: DNA
<213> ORGANISM: homo sapiens
<220> FEATURE:
<223> OTHER INFORMATION: Heavy chain frame work from VH1-18

<400> SEQUENCE: 54

```
caggttcagc tggtgcagtc tggagctgag gtgaagaagc ctggggcctc agtgaaggtc      60
tcctgcaagg cttctggtta ccctttacc agctatggta tcagctgggt gcgacaggcc     120
cctggacaag gcttgagtg gatgggatgg atcagcgctt acaatggtaa cacaaactat     180
gcacagaagc tccagggcag agtcaccatg accacagaca catccacgag cacagcctac     240
atggagctga ggagcctgag atctgacgac acggccgtgt attactgtgc gagaga         296
```

<210> SEQ ID NO 55
<211> LENGTH: 63
<212> TYPE: DNA
<213> ORGANISM: homo sapiens
<220> FEATURE:
<223> OTHER INFORMATION: Heavy chain frame work from JH-6

<400> SEQUENCE: 55

```
attactacta ctactacggt atggacgtct gggggcaagg gaccacggtc accgtctcct      60
cag                                                                    63
```

<210> SEQ ID NO 56
<211> LENGTH: 305
<212> TYPE: DNA
<213> ORGANISM: homo sapiens
<220> FEATURE:
<223> OTHER INFORMATION: Light chain frame work from VKB-3

<400> SEQUENCE: 56

```
gacatcgtga tgacccagtc tccagactcc ctggctgtgt ctctgggcga gagggccacc      60
atcaactgca gtccagcca gagtgttttta tacagctcca acaataagaa ctacttagct     120
tggtaccagc agaaaccagg acagcctcct aagctgctca tttactgggc atctacccgg     180
gaatccgggg tccctgaccg attcagtggc agcgggtctg ggacagattt cactctcacc     240
atcagcagcc tgcaggctga agatgtggca gtttattact gtcagcaata ttatagtact     300
cctcc                                                                  305
```

<210> SEQ ID NO 57
<211> LENGTH: 22
<212> TYPE: DNA
<213> ORGANISM: Artificial Sequence
<220> FEATURE:
<223> OTHER INFORMATION: SJ15R primer

<400> SEQUENCE: 57

```
ggtcactgtc actggctcag gg                                               22
```

```
<210> SEQ ID NO 58
<211> LENGTH: 28
<212> TYPE: DNA
<213> ORGANISM: Artificial Sequence
<220> FEATURE:
<223> OTHER INFORMATION: SJ16R primer

<400> SEQUENCE: 58
aggcggatcc aggggccagt ggatagac                                          28

<210> SEQ ID NO 59
<211> LENGTH: 26
<212> TYPE: DNA
<213> ORGANISM: Artificial Sequence
<220> FEATURE:
<223> OTHER INFORMATION: SJ17R primer

<400> SEQUENCE: 59
gcacacgact gaggcacctc cagatg                                            26

<210> SEQ ID NO 60
<211> LENGTH: 34
<212> TYPE: DNA
<213> ORGANISM: Artificial Sequence
<220> FEATURE:
<223> OTHER INFORMATION: SJ18R primer

<400> SEQUENCE: 60
cggcggatcc gatggataca gttgtgtcag catc                                   34
```